US012630839B2

(12) United States Patent
Huston

(10) Patent No.: US 12,630,839 B2
(45) Date of Patent: May 19, 2026

(54) COMPOSITIONS FOR THE TREATMENT OF FABRY DISEASE

(71) Applicant: Sangamo Therapeutics, Inc., Richmond, CA (US)

(72) Inventor: Marshall W. Huston, Richmond, CA (US)

(73) Assignee: Sangamo Therapeutics, Inc., Richmond, CA (US)

( * ) Notice: Subject to any disclaimer, the term of this patent is extended or adjusted under 35 U.S.C. 154(b) by 1261 days.

(21) Appl. No.: 16/734,271

(22) Filed: Jan. 3, 2020

(65) Prior Publication Data

US 2020/0239911 A1 Jul. 30, 2020

Related U.S. Application Data

(60) Provisional application No. 62/788,439, filed on Jan. 4, 2019.

(51) Int. Cl.
| | |
|---|---|
| *C12N 15/86* | (2006.01) |
| *A61K 38/47* | (2006.01) |
| *A61K 48/00* | (2006.01) |
| *A61P 3/00* | (2006.01) |

(Continued)

(52) U.S. Cl.
CPC .............. *C12N 15/86* (2013.01); *A61K 38/47* (2013.01); *A61K 48/0058* (2013.01); *A61P 3/00* (2018.01); *C12N 9/2465* (2013.01); *C12N 15/67* (2013.01); *C12N 2750/14143* (2013.01); *C12N 2800/22* (2013.01); *C12N 2830/008* (2013.01); *C12N 2830/42* (2013.01); *C12N 2830/48* (2013.01);

(Continued)

(58) Field of Classification Search
CPC ...... C12N 15/86; C12N 9/2465; C12N 15/67; C12N 2750/14143; C12N 2800/22; C12N 2830/008; C12N 2830/42; C12N 2830/48; C12N 2830/50; A61K 38/47; A61K 48/0058; A61K 31/573; A61P 3/00; C12Y 302/01022
See application file for complete search history.

(56) References Cited

U.S. PATENT DOCUMENTS

| | | | |
|---|---|---|---|
| 4,186,183 A | 1/1980 | Steck et al. | |
| 4,217,344 A | 8/1980 | Vanlerberghe et al. | |
| 4,235,871 A | 11/1980 | Papahadjopoulos et al. | |

(Continued)

FOREIGN PATENT DOCUMENTS

| | | |
|---|---|---|
| AU | 2016206297 A1 | 8/2016 |
| CN | 105950664 A | 9/2016 |

(Continued)

OTHER PUBLICATIONS

Sigma-Aldrich product sheet, Pluronic F-68, P1300, accessed Sep. 6, 2023, (Year: 2023).*

(Continued)

*Primary Examiner* — Jennifer Dunston
*Assistant Examiner* — Keyur A Vyas
(74) *Attorney, Agent, or Firm* — Sterne, Kessler, Goldstein & Fox P.L.L.C.

(57) ABSTRACT

The present disclosure provides expression constructs comprising a GLA transgene encoding the at least one α-Gal A protein for use in expressing α-Gal A proteins and preventing, inhibiting or treating Fabry disease or one or more symptoms associated with Fabry disease.

20 Claims, 14 Drawing Sheets

Specification includes a Sequence Listing.

| enhancer | promoter | intron | signal peptide | GLA coding region | 3' UTR | polyA | name |
|---|---|---|---|---|---|---|---|
| APOE | hAAT | HBB-IGG | GLA | GLAco | | bGH | Variant #4 (Fabry 1.0) |

| enhancer | promoter | intron | signal peptide | GLA coding region | 3' UTR | polyA | name |
|---|---|---|---|---|---|---|---|
| APOE | hAAT | HBB-IGG | GLA | GLAco | WPREmut6 v1 | bGH | Variant #21 (Fabry 2.0) |

(51) Int. Cl.
    *C12N 9/40*         (2006.01)
    *C12N 15/67*       (2006.01)

(52) U.S. Cl.
    CPC ..................... *C12N 2830/50* (2013.01); *C12Y*
                          *302/01022* (2013.01)

(56)           References Cited

U.S. PATENT DOCUMENTS

| | | | |
|---|---|---|---|
| 4,261,975 A | 4/1981 | Fullerton et al. | |
| 4,485,054 A | 11/1984 | Mezei et al. | |
| 4,501,728 A | 2/1985 | Geho et al. | |
| 4,774,085 A | 9/1988 | Fidler | |
| 4,797,368 A | 1/1989 | Carter et al. | |
| 4,837,028 A | 6/1989 | Allen | |
| 4,897,355 A | 1/1990 | Eppstein et al. | |
| 4,946,787 A | 8/1990 | Eppstein et al. | |
| 5,049,386 A | 9/1991 | Eppstein et al. | |
| 5,173,414 A | 12/1992 | Lebkowski et al. | |
| 5,176,996 A | 1/1993 | Hogan et al. | |
| 5,356,802 A | 10/1994 | Chandrasegaran | |
| 5,420,032 A | 5/1995 | Marshall et al. | |
| 5,422,251 A | 6/1995 | Fresco | |
| 5,436,150 A | 7/1995 | Chandrasegaran | |
| 5,487,994 A | 1/1996 | Chandrasegaran | |
| 5,585,245 A | 12/1996 | Johnsson et al. | |
| 5,789,538 A | 8/1998 | Rebar et al. | |
| 5,925,523 A | 7/1999 | Dove et al. | |
| 6,007,988 A | 12/1999 | Choo et al. | |
| 6,008,336 A | 12/1999 | Hanson et al. | |
| 6,013,453 A | 1/2000 | Choo et al. | |
| 6,140,081 A | 10/2000 | Barbas | |
| 6,140,466 A | 10/2000 | Barbas, III et al. | |
| 6,200,759 B1 | 3/2001 | Dove et al. | |
| 6,242,568 B1 | 6/2001 | Barbas, III et al. | |
| 6,410,248 B1 | 6/2002 | Greisman et al. | |
| 6,453,242 B1 | 9/2002 | Eisenberg et al. | |
| 6,479,626 B1 | 11/2002 | Kim et al. | |
| 6,503,717 B2 | 1/2003 | Case et al. | |
| 6,534,261 B1 | 3/2003 | Cox, III et al. | |
| 6,599,692 B1 | 7/2003 | Case et al. | |
| 6,607,882 B1 | 8/2003 | Cox, III et al. | |
| 6,689,558 B2 | 2/2004 | Case | |
| 6,794,136 B1 | 9/2004 | Eisenberg et al. | |
| 6,824,978 B1 | 11/2004 | Cox, III et al. | |
| 6,833,252 B1 | 12/2004 | Dujon et al. | |
| 6,852,510 B2 | 2/2005 | Bremel et al. | |
| 6,903,185 B2 | 6/2005 | Kim et al. | |
| 6,933,113 B2 | 8/2005 | Case et al. | |
| 6,979,539 B2 | 12/2005 | Cox, III et al. | |
| 7,013,219 B2 | 3/2006 | Case et al. | |
| 7,030,215 B2 | 4/2006 | Liu et al. | |
| 7,067,317 B2 | 6/2006 | Rebar et al. | |
| 7,070,934 B2 | 7/2006 | Cox, III et al. | |
| 7,074,596 B2 | 7/2006 | Darzynkiewicz et al. | |
| 7,153,949 B2 | 12/2006 | Kim et al. | |
| 7,163,824 B2 | 1/2007 | Cox, III et al. | |
| 7,253,273 B2 | 8/2007 | Collingwood | |
| 7,262,054 B2 | 8/2007 | Jamieson et al. | |
| 7,361,635 B2 | 4/2008 | Miller et al. | |
| 7,419,829 B2 | 9/2008 | Mitrophanous et al. | |
| 7,888,121 B2 | 2/2011 | Urnov et al. | |
| 7,914,796 B2 | 3/2011 | Miller et al. | |
| 7,951,925 B2 | 5/2011 | Ando et al. | |
| 7,972,854 B2 | 7/2011 | Miller et al. | |
| 8,021,867 B2 | 9/2011 | Smith et al. | |
| 8,034,598 B2 | 10/2011 | Miller | |
| 8,106,255 B2 | 1/2012 | Carroll et al. | |
| 8,110,379 B2 | 2/2012 | DeKelver et al. | |
| 8,153,773 B2 | 4/2012 | Jemielity et al. | |
| 8,409,861 B2 | 4/2013 | Guschin et al. | |
| 8,409,891 B2 | 4/2013 | Kuriyagawa et al. | |
| 8,563,314 B2 | 10/2013 | Gregory et al. | |
| 8,568,526 B2 | 10/2013 | Rueger et al. | |
| 8,586,526 B2 | 11/2013 | Gregory et al. | |
| 8,623,618 B2 | 1/2014 | Doyon et al. | |
| 8,697,359 B1 | 4/2014 | Zhang | |
| 8,703,489 B2 | 4/2014 | Wang | |
| 8,771,985 B2 | 7/2014 | Cui et al. | |
| 8,772,453 B2 | 7/2014 | Paschon et al. | |
| 8,823,618 B2 | 9/2014 | Lee et al. | |
| 8,895,264 B2 | 11/2014 | Cost et al. | |
| 8,932,814 B2 | 1/2015 | Cong et al. | |
| 8,945,868 B2 | 2/2015 | Collingwood et al. | |
| 8,956,828 B2 | 2/2015 | Bonini et al. | |
| 9,005,973 B2 | 4/2015 | Cost et al. | |
| 9,045,763 B2 | 6/2015 | DeKEL et al. | |
| 9,150,847 B2 | 10/2015 | Rebar | |
| 9,200,266 B2 | 12/2015 | Wang | |
| 9,206,404 B2 | 12/2015 | Cui et al. | |
| 9,222,105 B2 | 12/2015 | Cost et al. | |
| 9,255,250 B2 | 2/2016 | Gregory et al. | |
| 9,255,259 B2 | 2/2016 | Cost et al. | |
| 9,394,545 B2 | 7/2016 | Rebar | |
| 9,447,434 B2 | 9/2016 | Baltimore et al. | |
| 9,458,205 B2 | 10/2016 | Gregory et al. | |
| 9,567,573 B2 | 2/2017 | Gregory et al. | |
| 9,567,609 B2 | 2/2017 | Paschon et al. | |
| 9,597,357 B2 | 3/2017 | Gregory et al. | |
| 9,616,090 B2 | 4/2017 | Conway et al. | |
| 9,816,074 B2 | 11/2017 | Conway et al. | |
| 9,873,894 B2 | 1/2018 | Conway et al. | |
| 9,877,988 B2 | 1/2018 | Rebar | |
| 9,956,247 B2 | 5/2018 | Rebar | |
| 10,081,661 B2 | 9/2018 | Miller et al. | |
| 10,143,760 B2 | 12/2018 | Riley et al. | |
| 10,166,298 B2 | 1/2019 | Ansell et al. | |
| 10,179,918 B2 | 1/2019 | Cost | |
| 10,363,269 B2 | 7/2019 | Tareen | |
| 11,219,695 B2 | 1/2022 | Huston | |
| 2002/0055158 A1 | 5/2002 | Green et al. | |
| 2002/0106729 A1* | 8/2002 | Bleck ................. C07K 16/3061 | |
| | | | 435/456 |
| 2003/0073652 A1 | 4/2003 | Pollard et al. | |
| 2003/0077806 A1 | 4/2003 | Selden et al. | |
| 2003/0232410 A1 | 12/2003 | Liljedahl et al. | |
| 2004/0219132 A1 | 11/2004 | Fan et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2005/0267061 A1 | 12/2005 | Martin | |
| 2006/0063231 A1 | 3/2006 | Li et al. | |
| 2006/0188987 A1 | 8/2006 | Guschin et al. | |
| 2006/0189561 A1 | 8/2006 | Roelvink et al. | |
| 2007/0117128 A1 | 5/2007 | Smith et al. | |
| 2007/0218528 A1 | 9/2007 | Miller | |
| 2008/0159996 A1 | 7/2008 | Ando et al. | |
| 2009/0054985 A1 | 2/2009 | Anderson | |
| 2009/0068164 A1 | 3/2009 | Segal et al. | |
| 2009/0111106 A1 | 4/2009 | Mitrophanous et al. | |
| 2010/0041151 A1 | 2/2010 | Yew et al. | |
| 2010/0218264 A1 | 8/2010 | Cui et al. | |
| 2010/0226912 A1* | 9/2010 | Mehtali ................. A61P 19/02 | |
| | | | 435/69.6 |
| 2011/0265198 A1 | 10/2011 | Gregory et al. | |
| 2011/0301073 A1 | 12/2011 | Gregory et al. | |
| 2012/0017290 A1 | 1/2012 | Cui et al. | |
| 2012/0195936 A1 | 8/2012 | Rudolph et al. | |
| 2013/0122591 A1 | 5/2013 | Cost et al. | |
| 2013/0137104 A1 | 5/2013 | Cost et al. | |
| 2013/0177960 A1 | 7/2013 | Rebar | |
| 2013/0177983 A1 | 7/2013 | Rebar | |
| 2013/0196373 A1 | 8/2013 | Gregory et al. | |
| 2014/0001721 A1 | 1/2014 | Benko | |
| 2014/0017212 A1 | 1/2014 | Rebar | |
| 2014/0112896 A1 | 4/2014 | Rebar | |
| 2014/0120622 A1 | 5/2014 | Gregory et al. | |
| 2014/0179002 A1* | 6/2014 | Akada ................. C12N 15/113 | |
| | | | 435/320.1 |
| 2014/0335063 A1 | 11/2014 | Cannon et al. | |
| 2015/0056705 A1 | 2/2015 | Conway et al. | |
| 2015/0151007 A1 | 6/2015 | Dodge et al. | |
| 2015/0335708 A1 | 11/2015 | Froelich et al. | |
| 2016/0024474 A1 | 1/2016 | Conway et al. | |
| 2016/0030477 A1 | 2/2016 | Conway et al. | |

(56)                    References Cited

U.S. PATENT DOCUMENTS

| | | | |
|---|---|---|---|
| 2016/0060656 A1 | 3/2016 | Rebar | |
| 2016/0208284 A1 | 7/2016 | Huelsmann et al. | |
| 2016/0264953 A1 | 9/2016 | Lee et al. | |
| 2016/0326548 A1 | 11/2016 | Cost | |
| 2016/0375110 A1* | 12/2016 | High | A61K 38/4846 |
| | | | 514/44 R |
| 2017/0119904 A1 | 5/2017 | Ansell et al. | |
| 2017/0119906 A1 | 5/2017 | Riley | |
| 2017/0218349 A1 | 8/2017 | Miller et al. | |
| 2018/0087072 A1 | 3/2018 | Miller et al. | |
| 2018/0117181 A1 | 5/2018 | Huston | |
| 2018/0185516 A1 | 7/2018 | Ansell et al. | |
| 2018/0311290 A1* | 11/2018 | Sena-Esteves | C12N 9/2471 |
| 2019/0241877 A1 | 8/2019 | DeKelver et al. | |
| 2019/0358302 A1 | 11/2019 | Gotschall | |
| 2020/0147241 A1 | 5/2020 | Do et al. | |
| 2020/0239911 A1 | 7/2020 | Huston | |
| 2020/0283818 A1 | 9/2020 | Goel | |
| 2020/0299721 A1 | 9/2020 | Kim et al. | |
| 2022/0273819 A1 | 9/2022 | Huston | |

FOREIGN PATENT DOCUMENTS

| | | | |
|---|---|---|---|
| CN | 115667535 A | 1/2023 | |
| EP | 1961816 A1 | 8/2008 | |
| EP | 1325138 B1 | 7/2013 | |
| GB | 2338237 A | 12/1999 | |
| GB | 2338237 B | 2/2001 | |
| JP | 2002522509 A | 7/2002 | |
| JP | 2015527881 A | 9/2015 | |
| RU | 2535365 C2 | 12/2014 | |
| WO | WO-9116024 A1 | 10/1991 | |
| WO | WO-9117424 A1 | 11/1991 | |
| WO | WO-9324641 A2 | 12/1993 | |
| WO | WO-9519431 A1 | 7/1995 | |
| WO | WO-9606166 A1 | 2/1996 | |
| WO | WO-9837186 A1 | 8/1998 | |
| WO | WO-9844350 A1 | 10/1998 | |
| WO | WO-9853057 A1 | 11/1998 | |
| WO | WO-9853058 A1 | 11/1998 | |
| WO | WO-9853059 A1 | 11/1998 | |
| WO | WO-9853060 A1 | 11/1998 | |
| WO | WO-9854311 A1 | 12/1998 | |
| WO | WO-0009153 A1 | 2/2000 | |
| WO | WO-0027878 A1 | 5/2000 | |
| WO | WO-0160970 A2 | 8/2001 | |
| WO | WO-0188197 A2 | 11/2001 | |
| WO | WO-0207752 A2 | 1/2002 | |
| WO | WO-0216536 A1 | 2/2002 | |
| WO | WO-02077227 A2 | 10/2002 | |
| WO | WO-02099084 A2 | 12/2002 | |
| WO | WO-03016496 A2 | 2/2003 | |
| WO | WO-2007014275 A2 | 2/2007 | |
| WO | WO-2010079430 A1 | 7/2010 | |
| WO | WO-2012115980 A1 | 8/2012 | |
| WO | WO-2014011237 A1 | 1/2014 | |
| WO | WO-2015092440 A1 | 6/2015 | |
| WO | WO-2016181122 A1 | 11/2016 | |
| WO | WO-2017201328 A1 * | 11/2017 | A61K 38/47 |
| WO | WO-2018075736 A1 | 4/2018 | |
| WO | WO-2018160585 A2 | 9/2018 | |
| WO | WO-2020142752 A1 | 7/2020 | |

OTHER PUBLICATIONS

Wright et al., Identification of Factors that Contribute to Recombinant AAV2 Particle Aggregation and Methods to Prevent Its occurrence during vector purification and formulation, 2006, Mol Ther., 12(1):171-8. doi: 10.1016/j.ymthe. (Year: 2006).*

Huston et al., Liver-based expression of the human alpha-galactosidase A gene (GLA) in a murine Fabry model results in continuous supra-physiological enzyme activity and effective substrate reduction2017, Molecular Genetics and Metabolism, 117, pp. S69. (Year: 2017).*

Ahmad, I., et al., "Antibody-Mediated Specific Binding and Cytotoxicity of Liposome-Entrapped Doxorubicin to Lung Cancer Cells in Vitro," Cancer Research 52(17):4817-4820, American Association for Cancer Research, United States (1992).

Alvarez R. D., et al., "A phase I Study of Recombinant Adenovirus Vector-Mediated Intraperitoneal Delivery of Herpes Simplex Virus Thymidine Kinase (HSV-TK) Gene and Intravenous Ganciclovir for Previously Treated Ovarian and Extraovarian Cancer Patients," Human Gene Therapy 8(5):597-613, Mary Ann Liebert Inc., United States (1997).

Anderson, W. F., "Human Gene Therapy," Science 256(5058):808-813, American Association for the Advancement of Science, United States (May 1992).

Arends, M., et al., "Characterization of Classical and Nonclassical Fabry Disease: A Multicenter Study," Journal of the American Society of Nephrology 28(5):1631-1641, American Society of Nephrology, United States (published online Dec. 2016, published in print May 2017).

Argast, G. M., et al., "I-PpoI and I-CreI Homing Site Sequence Degeneracy Determined by Random Mutagenesis and Sequential in Vitro Enrichment," Journal of Molecular Biology 280(3):345-353, Elsevier, Netherlands (1998).

Ashworth, J., et al., "Computational Redesign of Endonuclease DNA Binding and Cleavage Specificity," Nature 441(7093):656-659, Nature Publishing Group, United Kingdom (2006).

Bangari D.S., et al., "α-Galactosidase A knockout mice: Progressive Organ Pathology Resembles the Type 2 Later-Onset Phenotype of Fabry Disease," The American Journal of Pathology, 185(3):651-665, Elsevier, United States (2015).

Beerli, R., et al., "Engineering Polydactyl Zinc-Finger Transcription Factors," Nature biotechnology 20(2):135-141, Nature America Publishing, United States (2002).

Behr, J. P., et al., "Gene Transfer With Synthetic Cationic Amphiphiles: Prospects for Gene Therapy," Bioconjugate Chemistry 5(5):382-389, American Chemical Society, United States (1994).

Belfort, J., et al., "Homing Endonucleases: Keeping the House in Order," Nucleic Acids Research 25(17):3379-3388, Oxford University Press, United Kingdom (1997).

Benjamin E.R., et al., "Co-Administration with the Pharmacological Chaperone AT1001 Increases Recombinant Human α-Galactosidase A Tissue Uptake and Improves Substrate Reduction in Fabry Mice," Molecular Therapy, 20(4):717-726, Cell Press, United Kingdom (2012).

Benjamin E.R., et al., "The Validation of Pharmacogenetics for the Identification of Fabry Patients to be Treated with Migalastat," Genetics in Medicine, 19(4):430-438, Nature Publishing Group, United States (2017).

Bennett, J., et al., "Safety and durability of effect of contralateral-eye administration of AAV2 gene therapy in patients with childhood-onset blindness caused by RPE65 mutations: a follow-on phase 1 trial," Lancet 388(10045):661-672, Elsevier Ltd., United Kingdom (published online Jun. 2016, published in print Aug. 2016).

Bitinaite, J., et al., "FokI Dimerization is Required for DNA Cleavage," Proceedings of the National Academy of Sciences of the United States of America 95(18):10570-10575, National Academy of Sciences, United States (1998).

Blaese, M., et al., "Vectors in Cancer Therapy: How Will They Deliver?," Cancer Gene Therapy 2(4):291-297, Nature Publishing Group, United Kingdom (1995).

Blaese, R. M., et al., "T Lymphocyte-Directed Gene Therapy for ADA-SCID: Initial Trial Results After 4 Years," Science 270(5235):475-480, American Association for the Advancement of Science, United States (1995).

Boch J., et al., "Breaking the Code of DNA Binding Specificity of TAL-Type III Effectors," Science, 326(5959):1509-1512, American Association for the Advancement of Science, United States (2009).

Bonas U., et al., "Genetic and Structural Characterization of the Avirulence Gene AvrBs3 from Xanthomonas Campestris Pv. Vesicatoria," Molecular & General Genetics, 218(1):127-136, Springer-Verlag, Germany (1989).

(56) References Cited

OTHER PUBLICATIONS

Buchschacher, G. L., et al., "Human Immunodeficiency Virus Vectors for Inducible Expression of Foreign Genes," Journal of Virology 66(5):2731-2739, American Society For Microbiology, United States (1992).

Chang, X. B., et al., "Modification of DNA Ends Can Decrease End Joining Relative to Homologous Recombination in Mammalian Cells," Proceedings of the National Academy of Sciences of the United States of America 84(14):4959-4963, National Academy of Sciences, United States (1987).

Chevalier, B. S., et al., "Design, Activity, and Structure of a Highly Specific Artificial Endonuclease," Molecular Cell 10(4):895-905, Cell Press, United States (2002).

Choi, J.-O., et al., "Characterization of Fabry mice treated with recombinant adeno-associated virus 2/8-mediated gene transfer," Journal of Biomedical Science 17:26, 10 pages, BioMed Central Ltd., on behalf of the National Science Council, United Kingdom (Apr. 2010).

Choo, Y. and Isalan, M., "Advances in Zinc Finger Engineering," Current Opinion in Structural Biology 10(4):411-416, Elsevier Science, United Kingdom (Aug. 2000).

Christian M., et al., "Targeting DNA Double-Strand Breaks with TAL Effector Nucleases," Genetics, 186(2):757-761, Oxford University Press, Oxford. (2010).

Clarke, J. T. R., et al., "The pharmacology of multiple regimens of agalsidase alfa enzyme replacement therapy for Fabry disease," Genetics in Medicine 9(8):504-509, Lippincott Williams and Wilkins Ltd., United States (2007).

Cong L., et al., "Multiplex Genome Engineering Using CRISPR/ Cas Systems," Science, 339(6121):819-823, American Association for the Advancement of Science, United States (2013).

Crystal, R. G., et al., "Transfer of Genes to Humans: Early Lessons and Obstacles to Success," Science 270(5235):404-410, American Association for the Advancement of Science, United States (1995).

Deegan, P. B., "Fabry disease, enzyme replacement therapy and the significance of antibody responses," Journal of Inherited Metabolic Disease 35(2):227-243, Springer, Netherlands (Oct. 2011).

Dillon, N., "Regulating Gene Expression in Gene Therapy," Trends in Biotechnology 11(5):167-173, Elsevier Science Publishers, United Kingdom (1993).

Dranoff, G., et al., "A Phase I Study of Vaccination with Autologous, Irradiated Melanoma Cells Engineered to Secrete Human Granulocyte-Macrophage Colony Stimulating Factor," Human Gene Therapy 8(1):111-123, Mary Ann Liebert Inc., United States (1997).

Dujon, B., et al., "Mobile Introns: Definition of Terms and Recommended Nomenclature," Gene 82(1):115-118, Elsevier, Netherlands (1989).

Dull, T., et al., "A Third-Generation Lentivirus Vector with a Conditional Packaging System," Journal of Virology 72(11):8463-8471, American Society For Microbiology, United States (1998).

Dunbar, C. E., et al., "Retrovirally Marked CD34-Enriched Peripheral Blood and Bone Marrow Cells Contribute to Long-Term Engraftment After Autologous Transplantation," Blood 85(11):3048-3057, American Society of Hematology, United States (1995).

Ellem, K. A., et al., "A Case Report: Immune Responses and Clinical Course of the First Human Use of Granulocyte/Macrophage-Colony-Stimulating-Factor-Transduced Autologous Melanoma Cells for Immunotherapy," Cancer Immunology, Immunotherapy, 44(1):10-20, Springer Verlag, Germany (1997).

El-Serag, H. B., and Davila, J. A., "Surveillance for hepatocellular carcinoma: in whom and how?," Therapeutic Advances in Gastroenterology 4(1):5-10, SAGE Publications Ltd., United States (Jan. 2011).

Epinat, J. C., et al., "A Novel Engineered Meganuclease Induces Homologous Recombination in Yeast and Mammalian Cells," Nucleic Acids Research 31(11):2952-2962, Oxford University Press, United Kingdom (2003).

Fagerlund R.D., et al., "The Cpf1 CRISPR-Cas Protein Expands Genome-Editing Tools," Genome Biology, 16:251, BioMed Central Ltd, United Kingdom (2015).

Fields, S., and Song, O., "A Novel Genetic System to Detect Protein-protein Interactions," Nature 340(6230):245-246, Nature Publishing Group, United Kingdom (Jul. 1989).

Follenzi, A., et al., "Gene Transfer by Lentiviral Vectors is Limited by Nuclear Translocation and Rescued by HIV-1 Pol Sequences," Nature Genetics 25(2):217-222, Nature Publishing Group, United Kingdom (2000).

Gabathuler, R., "Approaches to transport therapeutic drugs across the blood-brain barrier to treat brain diseases," Neurobiology of Disease 37(1):48-57, Elsevier, Netherlands (2010).

Gao, X., et al., "Cationic Liposome-Mediated Gene Transfer," Gene Therapy 2(10):710-722, Nature Publishing Group, United Kingdom (1995).

Garman, S. C., et al., "The Molecular Defect Leading to Fabry Disease: Structure of Human Alpha-Galactosidase," Journal of Molecular Biology 337(2):319-335, Elsevier, Netherlands (2004).

Gimble, F. S., et al., "Substrate Recognition and Induced DNA Distortion by the PI-Scel Endonuclease, an Enzyme Generated by Protein Splicing," Journal of Molecular Biology 263(2):163-180, Elsevier, Netherlands (1996).

Guo J., et al., "Directed Evolution of an Enhanced and Highly Efficient FokI Cleavage Domain for Zinc Finger Nucleases," Journal of Molecular Biology, 400(1):96-107, Elsevier, Netherlands (2010).

Haddada, H., et al., "Gene Therapy Using Adenovirus Vectors" in Molecular Repertoire of Adenoviruses III, pp. 297-306, Doerfler, W., et al., eds., part of the Current Topics in Microbiology and Immunology book series, Springer-Verlag, Germany (1995).

Haft, D.H., et al., "A Guild of 45 CRISPR-Associated (Cas) Protein Families and Multiple Crispr/Cas Subtypes Exist in Prokaryotic Genomes," PLoS Computational Biology 1(6):e60, Public Library of Science, United States (2005).

Han, X., et al., "Ligand-Directed Retroviral Targeting of Human Breast Cancer Cells," Proceedings of the National Academy of Sciences of the United States of America 92(21):9747- 9751, National Academy of Sciences, United States (1995).

Hartl F.U., et al., "Molecular Chaperones in Protein Folding and Proteostasis," Nature, 475(7356):324-332, Nature Publishing Group, Basingstoke. (2011).

Hermonat, P. L., et al., "Use of Adeno-Associated Virus as a Mammalian DNA Cloning Vector: Transduction of Neomycin Resistance into Mammalian Tissue Culture Cells," Proceedings of the National Academy of Sciences of the United States of America 81(20):6466-6470, National Academy of Sciences, United States (1984).

Heuer H., et al., "Repeat Domain Diversity of AvrBs3-Like Genes in Ralstonia Solanacearum Strains and Association with Host Preferences in the Field," Applied and Environmental Microbiology, 73(13):4379-4384, American Society for Microbiology, United States (2007).

International Search Report and Written Opinion for International Application No. PCT/US2017/057328, ISA/US, Commissioner for Patents, Alexandria, Virginia, mailed on Mar. 13, 2018, 14 pages.

International Search Report and Written Opinion for Application No. PCT/US2020/012274, mailed on Apr. 21, 2020, 12 pages.

Isalan, M., et al., "A Rapid, Generally Applicable Method to Engineer Zinc Fingers Illustrated by Targeting the HIV-1 Promoter," Nature Biotechnology 19:656-660, Nature America Publishing, United States (Jul. 2001).

Jansen R., et al., "Identification of Genes that are Associated with DNA Repeats in Prokaryotes," Molecular Microbiology, 43(6):1565-1575, Blackwell Scientific Publications, Oxford. (2002).

Jasin, M., et al., "Genetic Manipulation of Genomes with Rare-Cutting Endonucleases," Trends in Genetics 12(6):224-228, Elsevier Trends Journals, United States (1996).

Johann, S. V., et al., "GLVR1, a Receptor for Gibbon Ape Leukemia Virus, is Homologous to a Phosphate Permease of Neurospora Crassa and is Expressed at High Levels in the Brain and Thymus," Journal of Virology 66(3):1635-1640, American Society For Microbiology, United States (1992).

Jung S.C., et al., "Adeno-Associated Viral Vector-Mediated Gene Transfer Results in Long-Term Enzymatic and Functional Correction in Multiple Organs of Fabry Mice," Proceedings of the National

(56)          References Cited

OTHER PUBLICATIONS

Academy of Sciences of the United States of America, 98(5):2676-2681, National Academy of Sciences, United States (2001).

Kay S., et al., "A Bacterial Effector Acts as a Plant Transcription Factor and Induces a Cell Size Regulator," Science, 318(5850):648-651, American Association for the Advancement of Science, United States (2007).

Kearns, W. G., et al., "Recombinant Adeno-Associated Virus (AAV-CFTR) Vectors Do Not Integrate in a Site-Specific Fashion in an Immortalized Epithelial Cell Line," Gene Therapy 3(9):748-755, Nature Publishing Group, United Kingdom (1996).

Khanna R., et al., "The Pharmacological Chaperone AT2220 Increases the Specific Activity and Lysosomal Delivery of Mutant Acid Alpha-Glucosidase, and Promotes Glycogen Reduction in a Transgenic Mouse Model of Pompe Disease," Plos One, 9(7):e102092, Public Library of Science, San Francisco. (2014).

Kim, Y. G., et al., "Chimeric Restriction Endonuclease," Proceedings of the National Academy of Sciences of the United States of America 91(3):883-887, National Academy of Sciences, United States (1994).

Kim, Y. G., et al., "Hybrid Restriction Enzymes: Zinc Finger Fusions to Fok I Cleavage Domain," Proceedings of the National Academy of Sciences of the United States of America 93(3):1156-1160, National Academy of Sciences, United States (1996).

Kim, Y. G., et al., "Insertion and Deletion Mutants of FokI Restriction Endonuclease," The Journal of Biological Chemistry 269(50):31978-31982, Elsevier Inc., Netherlands (1994).

Kohn, D. B., et al., "Engraftment of Gene-Modified Umbilical Cord Blood Cells in Neonates with Adenosine Deaminase Deficiency," Nature Medicine 1(10):1017-1023, Nature Publishing Company, United States (1995).

Kormann, M.S., et al., "Expression of therapeutic proteins after delivery of chemically modified mRNA in mice," Nature Biotechnology 29(2):154-157, Nature America Publishing, United States (2011).

Kotin, R. M., "Prospects for The Use of Adeno-Associated Virus as a Vector for Human Gene Therapy," Human Gene Therapy 5(7):793-801, Mary Ann Liebert Inc., United States (1994).

Kozak, M., et al., "An Analysis of 5'-Noncoding Sequences from 699 Vertebrate Messenger RNAs," Nucleic Acids Research 15(20):8125-8148, Oxford University Press, United Kingdom (1987).

Kremer, E. J., et al., "Adenovirus and Adeno-Associated Virus Mediated Gene Transfer," British Medical Bulletin 51(1):31-44, Oxford University Press, United Kingdom (1995).

Lee, H. Y., et al., "Nanoparticle-Based Targeted Gene Therapy for Lung Cancer," American Journal of Cancer Research 6(5):1118-1134, e-Century Pub. Corp., United States (May 2016).

Lheriteau, E., et al., "Haemophilia Gene Therapy: Progress and Challenges," Blood Reviews 29(5):321-328, Elsevier, United Kingdom (Sep. 2015).

Li, L., et al., "Functional Domains in Fok I Restriction Endonuclease, " Proceedings of the National Academy of Sciences of the United States of America 89(10):4275-4279, National Academy of Sciences, United States (1992).

Li, L., et al., "Alteration of the Cleavage Distance of Fok I Restriction Endonuclease by Insertion Mutagenesis," Proceedings of the National Academy of Sciences of the United States of America, 90(7):2764-2768, National Academy of Sciences, United States (1993).

Linthorst, G. E., et al., "Enzyme therapy for Fabry disease: neutralizing antibodies toward agalsidase alpha and beta," Kidney Int 66(4):1589-1595, Elsevier, Netherlands (2004).

Luke, G. A., et al., "Occurrence, Function and Evolutionary Origins of '2A-like' Sequences in Virus Genomes, " The Journal of General Virology 89(4):1036-1042, Microbiology Society, United Kingdom (2008).

Macdiarmid, J. A., et al., "Sequential Treatment of Drug-Resistant Tumors With Targeted Minicells Containing SiRNA or a Cytotoxic Drug," Nature Biotechnology 27(7):643-651, Nature America Publishing, United States (2009).

Makarova K.S., et al., "A DNA Repair System Specific for Thermophilic Archaea and Bacteria Predicted by Genomic Context Analysis," Nucleic Acids Research, 30(2):482-496, Oxford University Press ,Oxford. (2002).

Makarova K.S., et al., "A Putative RNA-Interference-Based Immune System in Prokaryotes: Computational Analysis of the Predicted Enzymatic Machinery, Functional Analogies with Eukaryotic RNAi, and Hypothetical Mechanisms of Action," Biology Direct, 1:7, BioMed Central, United Kingdom (2006).

Malech, H. L., et al., "Prolonged Production of NADPH Oxidase-Corrected Granulocytes After Gene Therapy of Chronic Granulomatous Disease," Proceedings of the National Academy of Sciences of the United States of America 94(22):12133-12138, National Academy of Sciences, United States (1997).

Manno, C. S., et al., "Successful transduction of liver in hemophilia by AAV-Factor IX and limitations imposed by the host immune response," Nature Medicine 12(3):342-347, Nature Publishing Group, United Kingdom (published online Feb. 2006, published in print Mar. 2006).

Matsukado, K., et al., "Enhanced Tumor Uptake of Carboplatin and Survival in Glioma-Bearing Rats by Intracarotid Infusion of Bradykinin Analog, RMP-7," Neurosurgery 39(1):125-133, Oxford University Press, United Kingdom (1996).

Meghdari M., et al., "Carboxyl-Terminal Truncations Alter the Activity of the Human α-Galactosidase A," PloS one, 10(2):e0118341, Public Library of Science, San francisco. (2015).

Miao, C. H., et al., "Inclusion of the Hepatic Locus Control Region, an Intron, and Untranslated Region Increases and Stabilizes Hepatic Factor IX Gene Expression in Vivo But Not in Vitro," Molecular Therapy 1(6):522-532, Cell Press, United States (2000).

Miller, A. D., et al., "Construction and Properties of Retrovirus Packaging Cells Based on Gibbon Ape Leukemia Virus," Journal of Virology 65(5):2220-2224, American Society For Microbiology, United States (1991).

Miller, A. D., et al., "Human Gene Therapy Comes of Age," Nature 357(6378):455-460, Nature Publishing Group, United Kingdom (1992).

Mitani, K., et al., "Delivering Therapeutic Genes—Matching Approach and Application," Trends in Biotechnology 11(5):162-166, Elsevier Science Publishers, United Kingdom (1993).

Moise A., et al., "Substrate and Substrate-Mimetic Chaperone Binding Sites in Human α-Galactosidase A Revealed by Affinity-Mass Spectrometry," Journal of the American Society for Mass Spectrometry, 27(6):1071-1078, ACS Publications, United States (2016).

Moscou J.M., et al., "A Simple Cipher Governs DNA Recognition by TAL Effectors," Science, 326(5959):1501, American Association for the Advancement of Science, United States (2009).

Muzyczka, N., "Adeno-Associated Virus (AAV) Vectors: Will They Work?," The Journal of Clinical Investigation 94(4):1351, American Society for Clinical Investigation, Ann Arbor. (1994).

Nabel, G. J., and Felgner, P. L., "Direct Gene Transfer for Immunotherapy and Immunization, " Trends in Biotechnology 11(5):211-215, Elsevier Science Publishers, Netherlands (May 1993).

Nakai, H., et al., "Extrachromosomal recombinant adeno-associated virus vector genomes are primarily responsible for stable liver transduction in vivo," Journal of Virology 75(15):6969- 6976, American Society for Microbiology, United States (Aug. 2001).

Naldini, L., et al., "Efficient Transfer, Integration, and Sustained Long-Term Expression of the Transgene in Adult Rat Brains Injected with a Lentiviral Vector," Proceedings of the National Academy of Sciences of the United States of America 93(21):11382-11388, National Academy of Sciences, United States (1996).

Nathwani, A. C., et al., "Long-term safety and efficacy of factor IX gene therapy in hemophilia B," New England Journal of Medicine 371(21):1994-2004, Massachusetts Medical Society, United States (Nov. 2014).

Nehls, M., et al., "Two Genetically Separable Steps in the Differentiation of Thymic Epithelium," Science 272(5263):886-889, American Association for the Advancement of Science, United States (1996).

Okuyama, T., et al., "Liver-Directed Gene Therapy: A Retroviral Vector with a Complete LTR and the ApoE Enhancer-Alpha

(56) References Cited

OTHER PUBLICATIONS

1-Antitrypsin Promoter Dramatically Increases Expression of Human Alpha 1-Antitrypsin in Vivo," Human Gene Therapy 7(5):637-645, Mary Ann Liebert Inc., United States (1996).

Olovnikov I., et al., "Bacterial Argonaute Samples the Transcriptome to Identify Foreign DNA," Molecular cell, 51(5):594-605, Cell Press, United Kingdom (2013).

Ong, J. M., et al., "The WPRE Improves Genetic Engineering With Site-Specific Nucleases," BioRxiv, Cold Spring Harbor Laboratory, United States (Apr. 2017).

Pabo, C.O., et al., "Design and Selection of Novel Cys2His2 Zinc Finger Proteins," Annual Review of Biochemistry 70:313-340, Annual Reviews, United States (2001).

Paques, F., et al., "Meganucleases and DNA Double-Strand Break-Induced Recombination: Perspectives for Gene Therapy," Current Gene Therapy 7(1):49-66, Bentham Science Publishers, United Arab Emirates (2007).

Passineau M.J., et al., "α-Galactosidase A Expressed in the Salivary Glands Partially Corrects Organ Biochemical Deficits in the Fabry Mouse Through Endocrine Trafficking," Human Gene Therapy, 22(3):293-301, Liebert, United States (2011).

Penaud-Budloo, M., et al., "Pharmacology of Recombinant Adeno-associated Virus Production," Molecular Therapy. Methods & Clinical Development 8:166-180, Cell Press, United States (Jan. 2018).

Perler, F. B., et al., "Protein Splicing Elements: Inteins and Exteins—a Definition of Terms and Recommended Nomenclature," Nucleic Acids Research 22(7):1125-1127, Oxford University Press, United Kingdom (1994).

Ponder K.P., "Immune Response Hinders Therapy for Lysosomal Storage Diseases," The Journal of Clinical Investigation, 118(8):2686-2689, American Society for Clinical Investigation, United States (2008).

Remy, J. S., et al., "Gene Transfer With a Series of Lipophilic DNA-Binding Molecules, " Bioconjugate Chemistry 5(6):647-654, American Chemical Society, United States (1994).

Roberts, R. J., et al., "REBASE: Restriction Enzymes and Methyltransferases," Nucleic Acids Research 31(1):418-420, Oxford University Press, United Kingdom (2003).

Rosenecker, J., et al., "Adenovirus Infection in Cystic Fibrosis Patients: Implications for the Use of Adenoviral Vectors for Gene Transfer," Infection 24(1):5-8, Springer, Germany (1996).

Samulski, R. J., et al., "Helper-Free Stocks of Recombinant Adeno-Associated Viruses: Normal Integration Does Not Require Viral Gene Expression," Journal of Virology 63(9):3822-3828, American Society For Microbiology, United States (1989).

Schornack S., et al., "Gene-for-Gene-Mediated Recognition of Nuclear-Targeted AvrBs3-like Bacterial Effector Proteins," Journal of Plant Physiology, 163(3):256-257, Urban & Fischer, Germany. (2006).

Segal, D.J. and Barbas 3rd, C.F., "Custom DNA-Binding Proteins Come of Age: Polydactyl Zinc-Finger Proteins," Current Opinion in Biotechnology 12(6):632-637, Elsevier, United Kingdom (Dec. 2001).

Sharma, R., et al., "In vivo genome editing of the albumin locus as a platform for protein replacement therapy," Blood 126(15):1777-1784, American Society of Hematology, United States (2015).

Sheng, G., et al., "Structure-based cleavage mechanism of Thermus thermophilus Argonaute DNA guide strand-mediated DNA target cleavage," Proc Natl Acad Sci USA 111(2):652-657, National Academy of Science, United States (published online Dec. 2013, published in print Jan. 2014).

Sommerfelt, M. A., et al., "Receptor Interference Groups of 20 Retroviruses Plating on Human Cells," Virology 176(1):58-69, Academic Press, United States (1990).

Sterman, D. H., et al., "Adenovirus-Mediated Herpes Simplex Virus Thymidine Kinase/Ganciclovir Gene Therapy in Patients with Localized Malignancy: Results of a Phase I Clinical trial in Malignant Mesothelioma," Human Gene Therapy 9(7):1083-1092, Mary Ann Liebert Inc., United States (1998).

Swarts, D. C., et al., "DNA-guided DNA interference by a prokaryotic Argonaute," Nature 507(7491):258-261, Nature Publishing Group, United Kingdom (2014).

Tebas P., et al., "Gene Editing of CCR5 in Autologous CD4 T Cells of Persons Infected with HIV," The New England Journal of Medicine, 370(10):901-910, Massachusetts Medical Society, Boston. (2014).

Third Party Observation dated Oct. 18, 2021, mailed on Oct. 21, 2021, submitted in European Application No. EP 17861799.9, filed Oct. 19, 2017, 5 pages.

Topf, N., et al., "Regional 'Pro-Drug' Gene Therapy: Intravenous Administration of an Adenoviral Vector Expressing the E. coli Cytosine Deaminase Gene and Systemic Administration of 5-Fluorocytosine Suppresses Growth of Hepatic Metastasis of Colon Carcinoma," Gene Therapy 5(4):507-513, Nature Publishing Group, United Kingdom (1998).

Tratschin, J. D., et al., "A Human Parvovirus, Adeno-Associated Virus, as a Eucaryotic Vector: Transient Expression and Encapsidation of the Procaryotic Gene for Chloramphenicol Acetyltransferase," Molecular and Cellular Biology 4(10):2072-2081, American Society for Microbiology, United States (1984).

Tratschin, J. D., et al., "Adeno-Associated Virus Vector for High-Frequency Integration, Expression, and Rescue of Genes in Mammalian Cells," Molecular and Cellular Biology 5(11):3251-3260, American Society for Microbiology, United States (1985).

Van Brunt, J., et al., "Molecular Farming: Transgenic Animals as Bioreactors," Biotechnology 6(10):1149-1154, Nature Publishing Co., United States (1988).

Vigne, E., et al., "Third-Generation Adenovectors for Gene Therapy," Restorative Neurology and Neuroscience 8(1):35-36, IOS Press, Netherlands (1995).

Vogel J., "Biochemistry. A Bacterial Seek-and-Destroy System for Foreign DNA," Science, 344(6187):972-973, American Association for the Advancement of Science, United States (2014).

Wagner, J. A., et al., "Efficient and Persistent Gene Transfer of AAV-CFTR in Maxillary Sinus," Lancet 351(9117):1702-1703, Elsevier, United Kingdom (1998).

Welsh, M. J., et al., "Adenovirus-Mediated Gene Transfer for Cystic Fibrosis: Part A. Safety of Dose and Repeat Administration in the Nasal Epithelium. Part B. Clinical Efficacy in the Maxillary Sinus," Human Gene Therapy 6(2):205-218, Mary Ann Liebert Inc., United States (1995).

West, M. H., et al., "Gene Expression in Adeno-Associated Virus Vectors: The Effects of Chimeric MRNA Structure, Helper Virus, and Adenovirus VA1 RNA," Virology 160(1):38-47, Academic Press, United States (1987).

Wilson, C., et al., "Formation of Infectious Hybrid Virions With Gibbon Ape Leukemia Virus and Human T-Cell Leukemia Virus Retroviral Envelope Glycoproteins and the Gag and Pol Proteins of Moloney Murine Leukemia Virus," Journal of Virology 63(5):2374-2378, American Society For Microbiology, United States (1989).

Winchester, B., and Young, E., "18. Biochemical and genetic diagnosis of Fabry disease," in Fabry Disease: Perspectives from 5 Years of FOS, MEHTA, A., et al., eds., Oxford PharmaGenesis, United Kingdom (2006).

Yu, M., et al., "Progress Towards Gene Therapy for HIV Infection," Gene Therapy 1(1):13-26, Nature Publishing Group, United Kingdom (1994).

Yuan Y.R., et al., "Crystal Structure of A. Aeolicus Argonaute, a Site-Specific DNA-Guided Endoribonuclease, Provides Insights Into RISC-Mediated MRNA Ceavage," Molecular Cell, 19(3):405-419, Cell Press, United Kingdom (2005).

Zanta-Boussif, M. A., et al., "Validation of a Mutated PRE Sequence Allowing High and Sustained Transgene Expression While Abrogating WHV-X Protein Synthesis: Application to the Gene Therapy of WAS," Gene Therapy 16(5):605-619, Nature Publishing Group, United Kingdom (2009).

Zetsche, B., et al., "Cpf1 is a Single RNA-Guided Endonuclease of a Class 2 CRISPR-Cas System," Cell 163(3):759-771, Cell Press, United States (Oct. 2015).

Zuffery, R., et al., "Self-Inactivating Lentivirus Vector for Safe and Efficient in Vivo Gene Delivery," Journal of Virology 72(12):9873-9880, American Society For Microbiology, United States (1998).

(56)         References Cited

OTHER PUBLICATIONS

Zufferey, R., et al., "Woodchuck hepatitis virus posttranscriptional regulatory element enhances expression of transgenes delivered by retroviral vectors," Journal of Virology 73(4):2886-2892, American Society for Microbiology, United States (Apr. 1999).

Co-pending U.S. Appl. No. 17/572,189, inventor Huston; M. W., filed Jan. 10, 2022 (Not yet Published).

De Leeuw, C.N., et al., "rAAV-compatible MiniPromoters for restricted expression in the brain and eye," Molecular brain 9(1):52, BioMed Central, United Kingdom (May 2016).

Hickmott, J.W., et al., "PAX6 MiniPromoters drive restricted expression from rAAV in the adult mouse retina," Molecular therapy Methods & clinical development 3:16051, Cell Press, United States (Aug. 2016).

Logan, G.J., et al., "Identification of liver-specific enhancer-promoter activity in the 3' untranslated region of the wild-type AAV2 genome," Nature Genetics 49:1267-1273, Nature Portfolio, Germany (Jun. 2017).

Park, J., et al., "Long-term Correction of Globotriaosylceramide Storage in Fabry Mice by Recombinant Adeno-Associated Virus-mediated Gene Transfer," Proceedings of the National Academy of Sciences of the United States of America 100(6):3450-3454, National Academy of Sciences, United States (Mar. 2003).

Tsuji, S., et al., "Signal sequence and DNA-mediated expression of human lysosomal a-galactosidase A". Eur. J. Biochem. 165:275-280, Wiley, United States (Jul. 1987).

Song, L., et al. "Optimizing the transduction efficiency of capsid-modified AAV6 serotype vectors in primary human hematopoietic stem cells in vitro and in a xenograft mouse model in vivo". Cytotherapy, 15(8):986-998, Elsevier, Netherlands (Aug. 2013).

Lee, K., et al. "A biochemical and pharmacological comparison of enzyme replacement therapies for the glycolipid storage disorder Fabry disease". Glycobiology, 13(4):305-313, Oxford University Press, United Kingdom (Apr. 2003).

Sofronview, M. et al. "Astrocytes: biology and pathology" Acta Neuropathol (2010) 119:7-35, Published Dec. 10, 2009, 29 pages.

Yasuda, M. et al. "AAV2/6 Gene Therapy in a Murine Model of Fabry Disease Results in Supraphysiological Enzyme Activity and Effective Substrate Reduction" Molecular Therapy, Methods and Clinical Development vol. 18. (Sep. 2020), New York, 13 Pages.

* cited by examiner

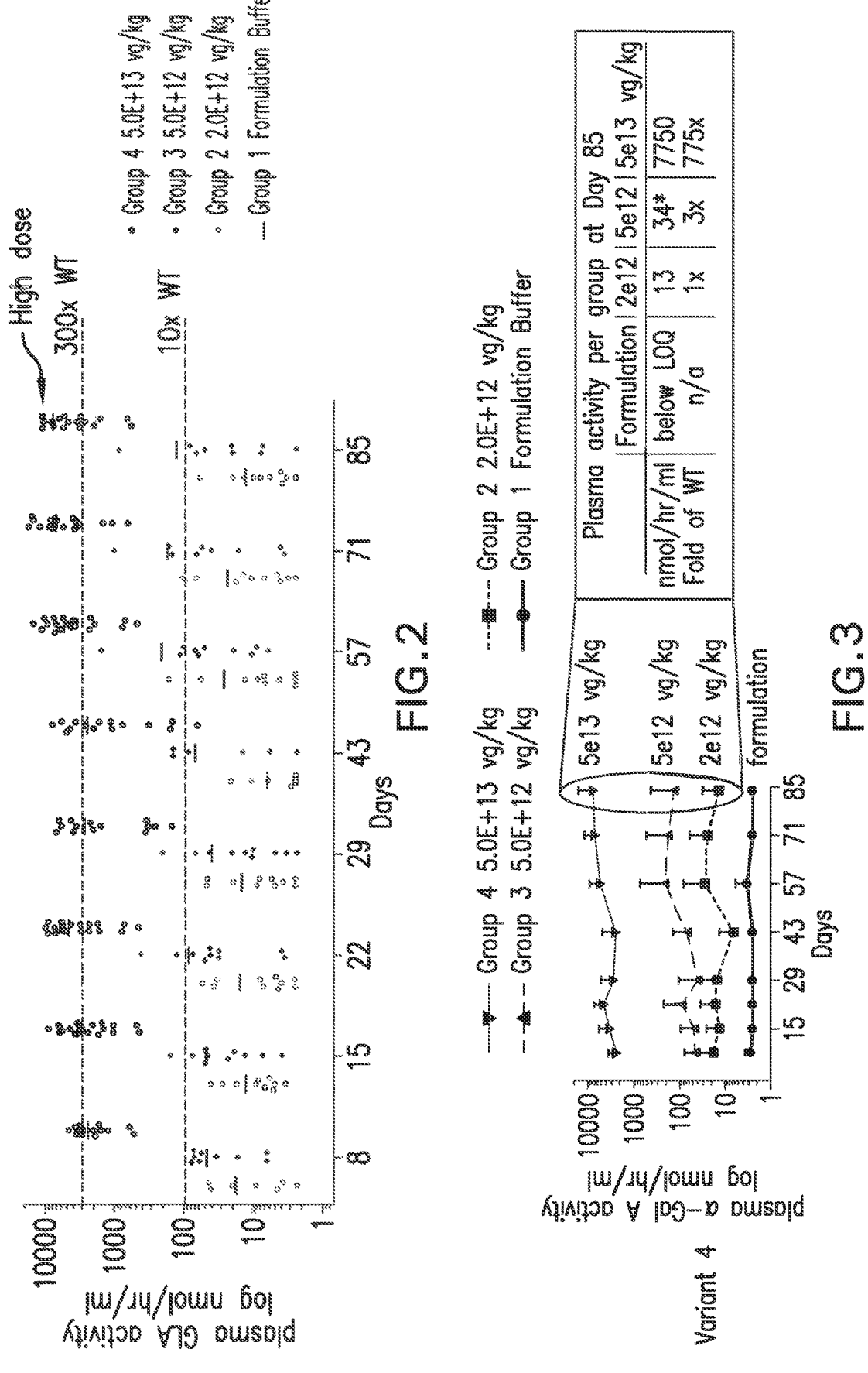

Variant 4

Variant 4

Variant 4

SEQUENCE LISTING

```
<160> NUMBER OF SEQ ID NOS: 10

<210> SEQ ID NO 1
<211> LENGTH: 130
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct                                                             130

<210> SEQ ID NO 2
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
aggctcagag gcacacagga gtttctgggc tcaccctgcc cccttccaac ccctcagttc      60
ccatcctcca gcagctgttt gtgtgctgcc tctgaagtcc acactgaaca aacttcagcc     120
tactcatgtc cctaaaatgg gcaaacattg caagcagcaa acagcaaaca cacagccctc     180
cctgcctgct gaccttggag ctggggcaga ggtcagagac ctctctgggc ccatgccacc     240
tccaacatcc actcgacccc ttggaatttc ggtggagagg agcagaggtt gtcctggcgt     300
ggtttaggta gtgtgagagg g                                                321

<210> SEQ ID NO 3
<211> LENGTH: 393
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
gatcttgcta ccagtggaac agccactaag gattctgcag tgagagcaga gggccagcta      60
agtggtactc tcccagagac tgtctgactc acgccacccc ctccaccttg gacacaggac     120
```

-continued

```
gctgtggttt ctgagccagg tacaatgact cctttcggta agtgcagtgg aagctgtaca      180
ctgcccaggc aaagcgtccg ggcagcgtag gcgggcgact cagatcccag ccagtggact      240
tagcccctgt ttgctcctcc gataactggg gtgaccttgg ttaatattca ccagcagcct      300
cccccgttgc ccctctggat ccactgctta aatacggacg aggacagggc cctgtctcct      360
cagcttcagg caccaccact gacctgggac agt                                    393

<210> SEQ ID NO 4
<211> LENGTH: 133
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
gtaagtatca aggttacaag acaggtttaa ggagaccaat agaaactggg cttgtcgaga       60
cagagaagac tcttgcgttt ctgataggca cctattggtc ttactgacat ccactttgcc      120
tttctctcca cag                                                          133

<210> SEQ ID NO 5
<211> LENGTH: 1290
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgcaactta ggaaccccga acttcatctt ggctgcgccc tggccctccg cttcctcgct       60
ctcgtttctt gggacatccc tggcgctagg cactcgaca acggcctcgc gcggactcct       120
acgatgggat ggttgcactg ggaaaggttt atgtgcaatc tggattgcca ggaggagccg      180
gactcatgca tctcggagaa gctgttcatg gagatggcgg aacttatggt atcggaggga      240
tggaaggatg ccgggtatga gtatctctgt atcgacgatt gttggatggc tccccagaga      300
gactccgagg gacgactcca agcggacccc cagcgctttc cacatggcat tcgacagctc      360
gccaattacg tgcactcgaa ggggttgaag ttgggaatct acgcagatgt gggcaacaaa      420
acgtgtgcgg ggttcccggg gtcgtttgga tactacgata ttgatgcgca gacgtttgct      480
gactggggtg tcgatctttt gaaatttgat ggctgttact gtgattcgtt ggaaaacctg      540
gcggatggat acaagcatat gtcactcgcc ttgaaccgga caggtcgctc aatcgtatac      600
agctgcgaat ggcccctcta tatgtggccc ttccaaaagc ccaattacac agagattcgg      660
cagtattgca atcactggag gaactttgcc gatattgacg acagctggaa atccatcaag      720
tccattctcg attggacgag cttcaaccag gagcgcatcg tggacgtggc aggacccgga      780
ggttggaacg atccggacat gctcgtaatt gggaatttcg gcttagctg gaatcagcaa       840 gtcacccaaa tggcgctgtg ggccatcatg gcagctcctc tctttatgtc gaatgatctg      900
cggcatatct cgccccaggc aaaggctctt ttgcaagaca aggacgtcat cgcaatcaat      960
caggacccat tggggaaaca gggatatcaa cttcgccagg gtgacaattt cgaagtatgg     1020
gagaggccgc ttagcgggct ggcgtgggcg gtcgcgatga ttaaccggca ggaaatcgga     1080
gggcctcgct cgtataccat cgcagtggcc tcactgggca aaggagtggc gtgcaatccg     1140
```

```
gcctgcttca tcacccagtt gttgcccgtc aaaagaaagc tgggtttcta cgagtggaca      1200
tccagactta gatcacacat taaccctact ggtacggtgt tgctccagct cgaaaacaca      1260
atgcagatgt cgttgaaaga cctgctgtaa                                       1290
```

```
<210> SEQ ID NO 6
<211> LENGTH: 592
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
```

```
aatcaacctc tggattacaa aatttgtgaa agattgactg gtattcttaa ctatgttgct       60 cctttacgc tatgtggata cgctgcttta atgcctttgt atcatgctat tgcttcccgt        120
atggctttca ttttctcctc cttgtataaa tcctggttgc tgtctcttta tgaggagttg      180
tggcccgttg tcaggcaacg tggcgtggtg tgcactgtgt ttgctgacgc aaccccccact      240 ggttggggca ttgccaccac ctgtcagctc ctttccggga cttttcgcttt cccctccct      300 attgccacgg cggaactcat cgccgcctgc cttgcccgct gctggacagg ggctcggctg      360
ttgggcactg acaattccgt ggtgttgtcg gggaaatcat cgtcctttcc ttggctgctc      420
gcctgtgttg ccacctggat tctgcgcggg acgtccttct gctacgtccc ttcggccctc      480
aatccagcgg accttccttc ccgcggcctg ctgccggctc tgcggcctct tccgcgtctt      540
cgccttcgcc ctcagacgag tcggatctcc ctttgggccg cctccccgcc tg              592
```

```
<210> SEQ ID NO 7
<211> LENGTH: 225
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
```

```
ctgtgccttc tagttgccag ccatctgttg tttgcccctc ccccgtgcct tccttgaccc       60
tggaaggtgc cactcccact gtcctttcct aataaaatga ggaaattgca tcgcattgtc      120
tgagtaggtg tcattctatt ctgggggggtg gggtggggca ggacagcaag ggggaggatt     180
gggaagacaa tagcaggcat gctggggatg cggtgggctc tatgg                      225
```

```
<210> SEQ ID NO 8
<211> LENGTH: 108
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
```

```
aggaacccct agtgatggag ttggccactc cctctctgcg cgctcgctcg ctcactgagg       60
ccgcccgggc tttgcccggg cggcctcagt gagcgagcga gcgcgcag                    108
```

```
<210> SEQ ID NO 9
<211> LENGTH: 3321
<212> TYPE: DNA
```

-continued

```
<213> ORGANISM: Artificial Sequence
<220> FEATURE:
<223> OTHER INFORMATION: Description of Artificial Sequence: Synthetic
      polynucleotide

<400> SEQUENCE: 9
ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120
aggggttcct gcggcctagt aggctcagag gcacacagga gtttctgggc tcaccctgcc     180
cccttccaac ccctcagttc ccatcctcca gcagctgttt gtgtgctgcc tctgaagtcc     240
acactgaaca aacttcagcc tactcatgtc cctaaaatgg gcaaacattg caagcagcaa     300
acagcaaaca cacagccctc cctgcctgct gaccttggag ctggggcaga ggtcagagac     360
ctctctgggc ccatgccacc tccaacatcc actcgacccc ttggaatttc ggtggagagg     420
agcagaggtt gtcctggcgt ggtttaggta gtgtgagagg ggtacccggg gatcttgcta     480
ccagtggaac agccactaag gattctgcag tgagagcaga gggccagcta agtggtactc     540
tcccagagac tgtctgactc acgccacccc ctccaccttg gacacaggac gctgtggttt     600
ctgagccagg tacaatgact cctttcggta agtgcagtgg aagctgtaca ctgcccaggc     660
aaagcgtccg ggcagcgtag gcgggcgact cagatcccag ccagtggact tagcccctgt     720
ttgctcctcc gataactggg gtgaccttgg ttaatattca ccagcagcct ccccgttgc     780 ccctctggat ccactgctta aatacggacg aggacagggc cctgtctcct cagcttcagg     840
caccaccact gacctgggac agtcaggtaa gtatcaaggt tacaagacag gtttaaggag     900
accaatagaa actgggcttg tcgagacaga gaagactctt gcgtttctga taggcaccta     960
ttggtcttac tgacatccac tttgcctttc tctccacagg caattgatcc ccctgatctg    1020
cggcctcgac ggtatcgata agcttgccac catgcaactt aggaaccccg aacttcatct    1080
tggctgcgcc ctggccctcc gcttcctcgc tctcgtttct tgggacatcc ctggcgctag    1140
ggcactcgac aacggcctcg cgcggactcc tacgatggga tggttgcact gggaaaggtt    1200
tatgtgcaat ctggattgcc aggaggagcc ggactcatgc atctcggaga agctgttcat    1260
ggagatggcg gaacttatgg tatcggaggg atggaaggat gccgggtatg agtatctctg    1320
tatcgacgat tgttggatgg ctccccagag agactccgag ggacgactcc aagcggaccc    1380
ccagcgcttt ccacatggca ttcgacagct cgccaattac gtgcactcga aggggttgaa    1440
gttgggaatc tacgcagatg tgggcaacaa aacgtgtgcg gggttcccgg ggtcgtttgg    1500
atactacgat attgatgcgc agacgtttgc tgactggggt gtcgatcttt tgaaatttga    1560
tggctgttac tgtgattcgt tggaaaacct ggcggatgga tacaagcata tgtcactcgc    1620
cttgaaccgg acaggtcgct caatcgtata cagctgcgaa tggcccctct atatgtggcc    1680
cttccaaaag cccaattaca cagagattcg gcagtattgc aatcactgga ggaactttgc    1740
cgatattgac gacagctgga aatccatcaa gtccattctc gattggacga gcttcaacca    1800
ggagcgcatc gtggacgtgg caggacccgg aggttggaac gatccggaca tgctcgtaat    1860
tgggaatttc gggcttagct ggaatcagca agtcacccaa atggcgctgt gggccatcat    1920
ggcagctcct ctctttatgt cgaatgatct gcggcatatc tcgccccagg caaaggctct    1980
tttgcaagac aaggacgtca tcgcaatcaa tcaggaccca ttggggaaac agggatatca    2040
acttcgccag ggtgacaatt cgaagtatgg gagaggccg cttagcgggc tggcgtgggc    2100
ggtcgcgatg attaaccggc aggaaatcgg agggcctcgc tcgtatacca tcgcagtggc    2160
```

-continued

```
ctcactgggc aaaggagtgg cgtgcaatcc ggcctgcttc atcacccagt tgttgcccgt   2220
caaaagaaag ctgggtttct acgagtggac atccagactt agatcacaca ttaaccctac   2280
tggtacggtg ttgctccagc tcgaaaacac aatgcagatg tcgttgaaag acctgctgta   2340
atctagagga tctcgagaga tctaatcaac ctctggatta caaaatttgt gaaagattga   2400
ctggtattct taactatgtt gctcctttta cgctatgtgg atacgctgct ttaatgcctt   2460
tgtatcatgc tattgcttcc cgtatggctt tcattttctc ctccttgtat aaatcctggt   2520
tgctgtctct ttatgaggag ttgtggcccg ttgtcaggca acgtggcgtg gtgtgcactg   2580
tgtttgctga cgcaaccccc actggttggg gcattgccac cacctgtcag ctcctttccg   2640
ggactttcgc tttccccctc cctattgcca cggcggaact catcgccgcc tgccttgccc   2700
gctgctggac aggggctcgg ctgttgggca ctgacaattc cgtggtgttg tcggggaaat   2760
catcgtcctt tccttggctg ctcgcctgtg ttgccacctg gattctgcgc gggacgtcct   2820
tctgctacgt cccttcggcc ctcaatccag cggaccttcc ttcccgcggc ctgctgccgg   2880
ctctgcggcc tcttccgcgt cttcgccttc gccctcagac gagtcggatc tccctttggg   2940
ccgcctcccc gcctgggatc tctgtgcctt ctagttgcca gccatctgtt gtttgcccct   3000
cccccgtgcc ttccttgacc ctggaaggtg ccactcccac tgtcctttcc taataaaatg   3060
aggaaattgc atcgcattgt ctgagtaggt gtcattctat tctggggggt ggggtggggc   3120
aggacagcaa gggggaggat tgggaagaca atagcaggca tgctggggat gcggtgggct   3180
ctatggaccg gtctcgagat ccactagggc cgcaggaacc cctagtgatg gagttggcca   3240
ctccctctct gcgcgctcgc tcgctcactg aggccgcccg ggctttgccc gggcggcctc   3300
agtgagcgag cgagcgcgca g                                             3321
```

```
<210> SEQ ID NO 10
<211> LENGTH: 9
<212> TYPE: PRT
<213> ORGANISM: Unknown
<220> FEATURE:
<223> OTHER INFORMATION: Description of Unknown:
      'LAGLIDADG' family peptide motif sequence

<400> SEQUENCE: 10

Leu Ala Gly Leu Ile Asp Ala Asp Gly
1               5
```

COMPOSITIONS FOR THE TREATMENT OF FABRY DISEASE

CROSS-REFERENCE TO RELATED APPLICATIONS

The present application claims the benefit of U.S. Provisional Application No. 62/788,439, filed Jan. 4, 2019, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 9, 2023, is named 4341_0190002_Seqlisting_ST25 and is 10,751 bytes in size.

TECHNICAL FIELD

The present disclosure is in the field of the prevention and/or treatment of Fabry Disease with gene therapy.

BACKGROUND

The α-galactosidase A (GLA) gene encodes the lysosomal hydrolase enzyme, α-galactosidase A (α-Gal A). α-Galactosidase is an enzyme that catalyzes hydrolysis of the terminal α-galactosyl moieties of oligosaccharides and polysaccharides.

Fabry disease is a X-linked lysosomal storage disease caused by mutations in the GLA gene. Lack of α-Gal A activity results in the progressive, systematic accumulation of its primary substrate, globotriaosylceramide (Gb3) and its deacetylated soluble form, globotriaosylsphingosine (lyso-Gb3). Long term accumulation of these substrates leads to renal disease, skin disorders, cardiac disease, corneal dystrophy (e.g. corneal and lenticular opacities), and/or cerebrovascular disease, with reduced life expectancy. Depending on the mutation and residual α-Gal A enzyme level, the disease presents as classical early-onset Fabry disease in childhood/adolescence or as an attenuated (adult) form later in life. Classical Fabr disease occurs when residual enzyme activity is <5% (Arends et al. 2017) and typically occurs in males. Early symptoms may include periodic acroparesthesia, angiokeratomas, corneal and lenticular opacities, progressive renal insufficiency, cardiac disease, and cerebrovascular events. The attenuated or adult form of Fabry disease commonly involves only one organ system, usually cardiac or renal.

In both classical and adult forms, the current standard of care is enzyme replacement therapy (ERT) using recombinant α-Gal A, FABRAZYME® (agalsidase beta or equivalent), or chaperone therapy, which is available only for patients whose mutations are amenable to it. Infusion of recombinant α-Gal A into the bloodstream allows transfer to secondary tissues via mannose-6-phosphate receptor-mediated uptake (cross-correction). However, the short half-life of the recombinant α-Gal A used in ERT (approximately 1 hour in plasma) (Clarke et al. 2007) necessitates a lifetime of infusions, with associated risk of infusion-related reactions in a significant proportion of patients (Clarke et al. 2007), some of which are severe. In addition, a significant percentage of patients eventually generate antibodies to the recombinant enzyme, which may impact the activity of the ERT enzyme, which consequently may not clear all substrate from organs such as the kidneys (Linthorst et al. 2004).

Recombinant α-Gal A products with longer half-lives are being developed which may be administered less frequently. However, it is anticipated that these will still require long-term administration with associated risk of infusion-related reactions and/or inactivity because of neutralizing antibodies, and that α-Gal A levels will still fluctuate significantly over time.

Thus, there is a need for alternative therapies that address the unmet needs in Fabry disease.

SUMMARY

Disclosed herein is a method of expressing at least one α galactosidase A (α-Gal A) protein in a cell. In some embodiments the method comprises administering an expression construct comprising a mutated WPRE sequence, optionally a mut6 mutated WRPE sequence, and a GLA transgene encoding at least one α-Gal A protein to the cell such that the α-Gal A protein is expressed in the cell.

In some embodiments, the expression construct comprises a wild-type GLA sequence or a codon optimized GLA sequence.

In some embodiments, the expression construct includes one or more of the following: an enhancer, a promoter, an intron, a sequence encoding a signal peptide and/or a polyadenylation signal, wherein the mutated WPRE sequence, optionally the mut6 mutated WRPE sequence, and the GLA transgene encoding at least one α-Gal A protein is located between the signal peptide and the sequence encoding the polyadenylation signal.

In some embodiments, the expression construct comprises the sequence of SEQ ID No: 9.

In some embodiments, the cell is in a subject with Fabry's disease.

In some embodiments, the cell is in a male subject.

In some embodiments, the expression construct is administered in a pharmaceutically acceptable carrier.

In some embodiments, the pharmaceutically acceptable carrier includes phosphate buffered saline containing CaCl2, MgCl2, NaCl, sucrose and Kolliphor® P 188 (Poloxamer 188).

In some embodiments, the expression construct sequence includes the sequence as shown in Table 1 and wherein the expression construct is delivered to the cell by an AAV viral vector.

In some embodiments, the AAV viral vector serotype is AAV2/6.

In some embodiments, the expression construct is administered to the subject at a dose of between about 5.0E+12 and 1.0E+14 vector genomes per kilogram (vg/kg).

In some embodiments, the expression construct is administered to the liver of the subject. In other embodiments, the expression vector is administered to the subject by intravenous infusion. In yet other embodiments, only one dose of the expression construct is administered to a subject.

In some embodiments, the subject is administered an immunosuppressant prior to and/or during administration of the expression construct. In some embodiments the immunosuppressant comprises prednisone.

In some embodiments, expression of at least one α galactosidase A (α-Gal A) protein is sustained for at least 3 months, at least 9 months, or at least 12 months.

In some embodiments, the α-Gal A protein expressed from the transgene decreases the amount of glycospingolipids in the subject by between at least about 2-fold to about 9-fold as compared to untreated subjects.

In some embodiments, the α-Gal A protein expressed from the transgene decreases the amount of glycospingolipids in the subject by at least about 80% compared to untreated subjects.

In some embodiments, the α-Gal A protein expressed from the transgene decreases the amount of glycospingolipids in one or more of the subject's plasma, liver, heart, kidney, or spleen.

In some embodiments, the expression construct manufactured in a HEK293 cell system provides GLA levels in the subject at about 21-fold higher as compared to GLA levels in subjects administered the expression construct manufactured in a Sf9 cell system.

In some embodiments, α-Gal A protein activity in a subject is between about 100-fold higher to 1,500-fold higher than physiological normal/wild type.

In some embodiments, the α-Gal A protein expressed from the transgene is active in kidneys, liver and heart of the subject.

In some embodiments, the GLA transgene is maintained extra-chromosomally and not integrated into a genome of the cell.

In some embodiments, one or more nucleases that cleave an endogenous albumin gene in a liver cell in a subject are administered such that the transgene is integrated into and expressed from the albumin gene.

Genetically modified cells comprising an exogenous GLA transgene, made by the methods described herein are presented. In some embodiments, the cell is a stem cell or a precursor cell. In some embodiments, the cell is a liver or muscle cell. In some embodiments, the GLA transgene is maintained extra-chromosomally and not integrated into the genome of the cell. In some embodiments, the GLA transgene is integrated into the genome of the cell.

A method of preventing, inhibiting or treating Fabry disease or one or more symptoms associated with Fabry disease, is also presented. The method may include administering an expression construct to a subject in need thereof, the expression construct comprising a mutated WPRE sequence, optionally a mut6 mutated WRPE sequence, and a GLA transgene encoding at least one α-Gal A protein.

In some embodiments, the symptoms comprise one or more of Gb3 levels above normal or baseline, lyso-Gb3 levels above normal or baseline, renal disease, cardiac disease, acroparesthesia, angiokeratomas, GI tract pain, corneal and lenticular opacities, or cerebrovascular disease. As described herein, baseline can mean any starting measurement, i.e., a measurement taken before a particular treatment is administered. In some embodiments, the subject is male and has α-Gal A enzyme activity of less than about 5%. In some embodiments, the expression construct comprises a wild-type GLA sequence or a codon optimized GLA sequence. In some embodiments, the expression construct further comprises one or more of the following: an enhancer, a promoter, an intron, a sequence encoding a signal peptide and/or a polyadenylation signal, wherein the mutated WPRE sequence, optionally the mut6 mutated WRPE sequence, and the GLA transgene encoding at least one α-Gal A protein is located between the signal peptide and the sequence encoding the polyadenylation signal. In some embodiments, the expression B construct is administered in a pharmaceutically acceptable carrier.

In some embodiments, the pharmaceutically acceptable carrier comprises phosphate buffered saline containing CaCl2), MgCl2, NaCl, sucrose and Kolliphor® P 188 (Poloxamer 188).

In other embodiments, the expression construct sequence comprises the sequence as shown in Table 1 and wherein the expression construct is delivered to cells of the subject by an AAV viral vector. In some embodiments, the AAV viral vector serotype is AAV2/6.

In some embodiments, the expression construct is administered to the subject at a dose of between about 5.0E+12 and 1.0E+14 vector genomes per kilogram (vg/kg). In some embodiments, the expression construct is administered to the liver of the subject. In some embodiments, the expression vector is administered to the subject by intravenous infusion. In some embodiments, only one dose of the expression construct is administered to the subject.

In some embodiments, subjects are administered an immunosuppressant prior to and/or during administration of the expression construct. In some embodiments, the immunosuppressant includes prednisone. In some embodiments, expression of the at least one α galactosidase A (α-Gal A) protein is sustained for at least 3 months, at least 9 months, or at least 12 months.

In other embodiments, the α-Gal A protein expressed from the transgene decreases the amount of glycospingolipids in the subject by between at least about 3-fold to about 9-fold as compared to untreated subjects.

In some embodiments, the α-Gal A protein expressed from the transgene decreases the amount of glycospingolipids in the subject by at least about 80% compared to untreated subjects.

In some embodiments, the α-Gal A protein expressed from the transgene decreases the amount of glycospingolipids in one or more of the subject's plasma, liver, heart, kidney, or spleen.

In some embodiments, the expression construct is manufactured in a HEK293 cell system and wherein the GLA levels in the subject are 21-fold higher as compared to GLA levels in subjects administered the expression construct manufactured in a Sf9 cell system.

In some embodiments, α-Gal A protein activity in a subject is between about 100-fold higher to 1,500-fold higher than normal/wild type.

In some embodiments, the α-Gal A protein expressed from the transgene is active in kidneys, liver and heart of the subject.

In some embodiments, the GLA transgene is maintained extra-chromosomally and not integrated into a genome of the subject's cell.

In some embodiments, the methods include administering one or more nucleases that cleave an endogenous albumin gene in a liver cell in a subject such that the transgene is integrated into and expressed from the albumin gene.

Described herein are compositions comprising an expression construct, the expression construct comprising a mutated WPRE sequence, optionally a mut6 mutated WRPE sequence, and a GLA transgene encoding the at least one α-Gal A protein for the treatment of Fabry's disease.

In some embodiments, the composition includes a pharmaceutically acceptable carrier wherein the pharmaceutically acceptable carrier comprises CaCl2), MgCl2, NaCl, sucrose and Kolliphor® P 188 (Poloxamer 188).

In some embodiments, the composition includes a wild-type GLA sequence or a codon optimized GLA sequence.

In some embodiments, the composition includes one or more of the following: an enhancer, a promoter, an intron, a sequence encoding a signal peptide and/or a polyadenylation signal, wherein the mutated WPRE sequence, optionally the mut6 mutated WRPE sequence, and the GLA transgene encoding at least one α-Gal A protein is located between the signal peptide and the sequence encoding the polyadenylation signal.

In some embodiments, the composition includes the sequence as shown in Table 1 and wherein the expression construct is delivered to a cell by an AAV viral vector. In some embodiments, the composition includes the AAV viral vector serotype, AAV2/6.

In some embodiments, the composition includes an expression construct that comprises between about 5.0E+12 and 1.0E+14 vector genomes per subject kilogram (vg/kg).

In some embodiments, the composition includes an expression construct that comprises the sequence of SEQ ID No: 9.

A method of producing an α-Gal A protein for the treatment of Fabry disease, the method comprising expressing the α-Gal A protein in an isolated cell according to the method of any one of claims 1-4, and isolating the α-Gal A protein produced by the cell is also presented.

A delivery vector is presented comprising a mutated WRPE sequence, optionally a mut6 WPRE sequence and a GLA transgene for use in the methods described herein.

In some embodiments, the delivery vector is a viral vector or a lipid nanoparticle (LNP). In some embodiments, the viral vector comprises an AAV2/6 and wherein the viral vector delivers the expression construct to at least 50%, at least 60%, at least 70%, or at least 80% of cells.

Use of an expression construct, an AAV vector and/or genetically modified cell of any of the preceding claims for the treatment of Fabry's disease is also presented herein. In some embodiments, the enhancer comprises SEQ ID No: 2, the promotor comprises SEQ ID No: 3, the intron comprises SEQ ID No: 4, the GLA transgene comprises SEQ ID No: 5, the mutated WPRE sequence comprises SEQ ID No: 6, and the polyadenylation signal comprises SEQ ID No. 7.

In some embodiments, the composition includes the enhancer of SEQ ID No: 2, the promotor of SEQ ID No: 3, the intron of SEQ ID No: 4, the GLA transgene of SEQ ID No: 5, the mutated WPRE sequence of SEQ ID No: 6, and the polyadenylation signal of SEQ ID No. 7.

BRIEF DESCRIPTION OF THE DRAWINGS

FIG. 2 shows a graph indicating the plasma GLA activity in individual GLA knock-out (GLAKO) mice in the indicated Groups 2 through 4 treated with variant #4 construct or control animals as shown over 85 days. Group 1 was treated with formulation buffer ("Formulation"). Group 2 was treated with constructs at a dose of 2.0E+12 vg/kg, Group 3 was treated with constructs at a dose 5.0E+12 vg/kg, and Group 4 was treated with constructs at a dose 5.0E+13 vg/kg.

FIG. 3 is a graph indicating the plasma GLA activity in GLAKO mice in the indicated Groups 2 through 4 treated with expression constructs (variant #4 expression construct) or control animals over 85 days. Group 1 was administered formulation buffer ("Formulation"). Group 2 was treated with constructs at a dose of 2.0E+12 vg/kg, Group 3 was treated with constructs at a dose of 5.0E+12 vg/kg, and Group 4 was treated with constructs at a dose of 5.0E+13 vg/kg.

DETAILED DESCRIPTION

Figures 1A, 1B:
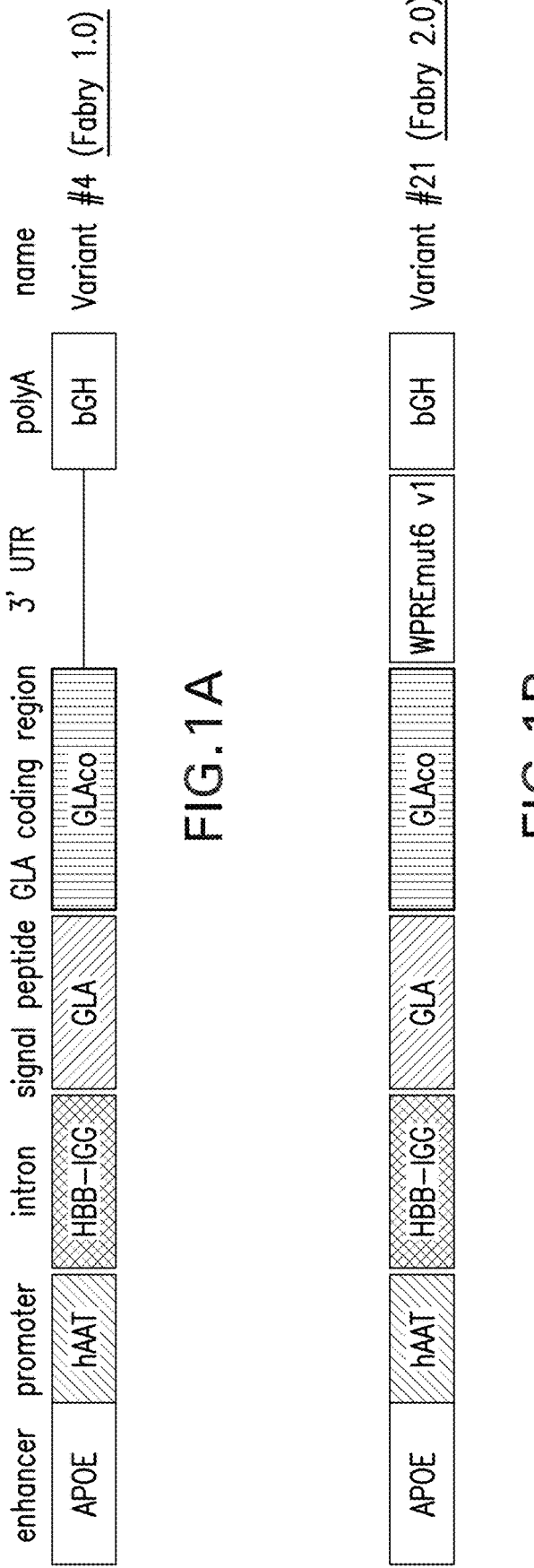
FIG. 1A shows a schematic depicting a construct encoding a GLA gene, designated variant #4. The variant #4 construct includes an enhancer (e.g., APOE); a promoter (e.g., hAAT); an intron sequence (e.g., HBB-IGG); a signal peptide (e.g., GLA); a GLA coding sequence (e.g., "GLAco"); and a polyadenylation signal (e.g., bGH).
FIG. 1B shows a schematic depicting a construct encoding a GLA gene, designated variant #21, which includes a mutated woodchuck hepatitis virus posttranscriptional regulatory element (WPRE) (also known as "mut 6" or "WPREmut6 v1"). The variant #21 construct also includes an enhancer (e.g., APOE); a promoter (e.g., hAAT); an intron sequence (e.g., HBB-IGG); a signal peptide (e.g., GLA); a GLA coding sequence (e.g., "GLAco"); and a polyadenylation signal (e.g., bGH).

Disclosed herein are methods and compositions for treating or preventing Fabry disease. The description provides methods and compositions for introduction of a GLA transgene encoding a protein that is lacking or insufficiently expressed in the subject with Fabry disease such that the gene is expressed in the liver and the therapeutic (replacement) protein is expressed. The description also describes the alteration of a cell (e.g., precursor or mature RBC, iPSC or liver cell) such that it produces high levels of the therapeutic and the introduction of a population of these altered cells into a patient will supply that needed protein. The transgene can encode a desired protein or structural RNA that is beneficial therapeutically in a patient in need thereof.

Gene therapy with adeno-associated viral (AAV) vectors has shown great promise in both preclinical and clinical trials to efficiently deliver therapeutic transgenes to the liver, with reports of stable levels of transgene expression out to six years for hemophilia B (Lheriteau E, Davidoff E, Nathwani A C. Haemophilia gene therapy: Progress and challenges. Blood Rev. 2015 September; 29(5):321-8).

One area that is especially promising is the ability to add a transgene to a cell to cause that cell to express a product that previously was not being produced in that cell or was being produced suboptimally. Examples of uses of this technology include the insertion of a gene encoding a therapeutic protein, insertion of a coding sequence encoding a protein that is somehow lacking in the cell or in the individual and insertion of a sequence that encodes a structural nucleic acid such as a microRNA.

Transgenes may be introduced and maintained in cells in a variety of ways. Following a "cDNA" approach, a transgene is introduced into a cell such that the transgene is maintained extra-chromosomally rather than via integration into the chromatin of the cell. The transgene may be maintained on a circular vector (e.g. a plasmid, or a non-integrating viral vector such as AAV or Lentivirus), where the vector can include transcriptional regulatory sequences such as promoters, enhancers, polyA signal sequences, introns, and splicing signals (U.S. Pat. No. 10,143,760).

Transgenes can be delivered to a cell by a variety of ways, such that the transgene becomes integrated into the cell's own genome and is maintained there. In recent years, a strategy for transgene integration has been developed that uses cleavage with site-specific nucleases for targeted insertion into a chosen genomic locus (see, e.g., co-owned U.S. Pat. No. 7,888,121). Nucleases, such as zinc finger nucleases (ZFNs), transcription activator-like effector nucleases (TAL-ENs), or nuclease systems such as the RNA guided CRISPR/Cas system (utilizing an engineered guide RNA), are specific for targeted genes and can be utilized such that the transgene construct is inserted by either homology directed repair (HDR) or by end capture during non-homologous end joining (NHEJ) driven processes. See, e.g., U.S. Pat. Nos. 9,877,988; 9,816,074; 9,616,090; 9,873,894; 9,597,357; 9,567,573; 9,458,205; 9,447,434; 9,394,545; 9,255,250; 9,222,105; 9,206,404; 9,200,266; 9,045,763; 9,005,973; 9,150,847; 8,956,828; 8,945,868; 8,895,264; 8,771,985; 8,703,489; 8,586,526; 8,106,255; 6,534,261; 6,599,692; 6,503,717; 6,689,558; 7,067,317; 7,262,054; 7,888,121; 7,972,854; 7,914,796; 7,951,925; 8,110,379; 8,409,861; U.S. Patent Publications 20030232410 and 20050064474, the disclosures of which are incorporated by reference in their entireties.

Transgenes can be integrated into a highly expressed safe harbor location such as the albumin gene (see U.S. Pat. No. 9,394,545). This approach has been termed the In Vivo Protein Replacement Platform or IVPRP. Following this approach, the transgene is inserted into the safe harbor (e.g., Albumin) gene via nuclease-mediated targeted insertion where expression of the transgene is driven by the Albumin promoter. The transgene is engineered to comprise a signal sequence to aid in secretion/excretion of the protein encoded by the transgene.

"Safe harbor" loci include loci such as the AAVS1, HPRT, Albumin and CCR5 genes in human cells, and Rosa26 in murine cells. See, e.g., U.S. Pat. Nos. 9,877,988; 9,567,573; 9,447,434; 9,394,545; 9,222,105; 9,206,404; 9,150,847; 8,895,264; 8,771,985; 8,106,255; 7,888,121; 7,972,854; 7,914,796; 7,951,925; 8,110,379; 8,409,861; and 8,586,526; U.S. Patent Publications 20030232410 and 20060063231. Nuclease-mediated integration offers the prospect of improved transgene expression, increased safety and expressional durability, as compared to classic integration approaches that rely on random integration of the transgene, since it allows exact transgene positioning for a minimal risk of gene silencing or activation of nearby oncogenes. Nuclease-mediated transgene insertion of genes encoding therapeutic Fabry proteins is described in U.S. Publication No. 20180117181.

While delivery of the transgene to the target cell is one hurdle that must be overcome to fully enact this technology, another issue that must be conquered is ensuring that after the transgene is inserted into the cell and is expressed, the gene product so encoded must reach the necessary location with the organism, and be made in sufficient local concentrations to be efficacious. For diseases characterized by the lack of a protein or by the presence of an aberrant non-functional protein, delivery of a transgene encoded wild type protein can be extremely helpful.

Lysosomal storage diseases (LSDs) are a group of rare metabolic monogenic diseases characterized by the lack of functional individual lysosomal proteins normally involved in the breakdown of waste lipids, glycoproteins and muco-polysaccharides. These diseases are characterized by a buildup of these compounds in the cell since it is unable to process them for recycling due to the mis-functioning of a specific enzyme. The most common examples are Gaucher's (glucocerebrosidase deficiency—gene name: GBA), Fabry's (a galactosidase A deficiency—GLA), Hunter's (iduronate-2-sulfatase deficiency-IDS), Hurler's (alpha-L iduronidase deficiency—IDUA), Pompe's (alpha-glucosidase (GAA)) and Niemann-Pick's (sphingomyelin phosphodiesterase 1 deficiency—SMPD1) diseases. When grouped all together, LSDs have an incidence in the population of about 1 in 7000 births. See, also, U.S. Pat. Nos. 9,877,988 and 9,956,247 and U.S. Publication No 20160060656.

For instance, Fabry disease is an X-linked disorder of glycosphingolipid metabolism caused by a deficiency of the $\alpha$-galactosidase A enzyme ($\alpha$-GalA). It is associated with the progressive deposition of glycospingolipids including globotriaosylceramide (also known as GL-3 and Gb3) and globotriaosylsphingosine (lyso-Gb3), galabioasylceramide, and group B substance. Symptoms of the disease are varied and can include burning, tingling pain (acroparesthesia) or episodes of intense pain which are called 'Fabry crises' which can last from minutes to days. Other symptoms include impaired sweating, low tolerance for exercise, reddish-purplish rash called angiokeratoma, eye abnormalities, gastrointestinal problems, heart problems such as enlarged heart and heart attack, kidney problems that can lead to renal failure and CNS problems and in general. Life expectancy for Fabry patients is shortened substantially.

Current treatment for Fabry disease can involve enzyme replacement therapy (ERT) with two different preparations of human $\alpha$-GalA, agalsidase beta or agalsidase alfa, which requires costly and time-consuming infusions (typically between about 0.2-1 mg/kg) for the patient every two weeks. Such treatment is only to treat the symptoms and is not curative. Accordingly, the patient must be given repeated dosing of these proteins for the rest of their lives, and potentially may develop neutralizing antibodies to the injected protein.

Furthermore, adverse reactions are associated with ERT, including immune reactions such as the development of anti-$\alpha$-GalA antibodies in subjects treated with the $\alpha$-GalA preparations. In fact, 50% of males treated with agalsidase alfa and 88% of males treated with agalsidase beta developed $\alpha$-GalA antibodies. Importantly, a significant proportion of those antibodies are neutralizing antibodies and, consequently, reduce the therapeutic impact of the treatment (Meghdari et al (2015) *PLoS One* 10(2):e0118341. Doi: 10.1371/journal.pone.0118341). In addition, ERT does not halt disease progression in all patients.

Thus, the methods and compositions can be used to express, from a transgene, one or more therapeutically beneficial $\alpha$-GalA proteins from a cDNA construct delivered, for example, by a viral vector, or inserted into any locus (e.g., highly expressed albumin locus) to replace the enzyme that is defective and/or lacking in Fabry disease. Additionally, the description provides methods and compositions for treatment (including the alleviation of one or more symptoms) of Fabry disease by insertion of the transgene sequences into highly expressed loci in cells such as liver cells. Included in the disclosure are methods and compositions for delivery of the $\alpha$-GalA encoding transgene via a viral vector to the liver of a subject in need thereof where the virus may be introduced via injection into the peripheral venus system or via direct injection into a liver-directed blood vessel (e.g. portal vein). The methods and compositions can be used to induce insertion of the transgene into a safe harbor locus (e.g. albumin) or can be used to cause extrachromosomal maintenance of a viral cDNA construct in a liver cell. In either case, the transgene is highly expressed and provides therapeutic benefit to the Fabry patient in need.

In addition, the transgene can be introduced into patient derived cells, e.g. patient derived induced pluripotent stem cells (iPSCs) or other types of stems cells (embryonic or hematopoietic) for use in eventual implantation. Particularly useful is the insertion of the therapeutic transgene into a hematopoietic stem cell for implantation into a patient in need thereof. As the stem cells differentiate into mature cells, they will contain high levels of the therapeutic protein for delivery to the tissues.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding domain" is a molecule that is able to bind non-covalently to another molecule. A binding molecule can bind to, for example, a DNA molecule (a DNA-binding protein such as a zinc finger protein or TAL-effector domain protein or a single guide RNA), an RNA molecule (an RNA-binding protein) and/or a protein molecule (a protein-binding protein). In the case of a protein-binding molecule, it can bind to itself (to form homodimers, homotrimers, etc.) and/or it can bind to one or more molecules of a different protein or proteins. A binding molecule can have more than one type of binding activity. For example, zinc finger proteins have DNA-binding, RNA-binding and protein-binding activity. Thus, DNA-binding molecules, including DNA-binding components of artificial nucleases and transcription factors include but are not limited to, ZFPs, TALEs and sgRNAs.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Artificial nucleases and transcription factors can include a ZFP DNA-binding domain and a functional domain (nuclease domain for a ZFN or transcriptional regulatory domain for ZFP-TF). The term "zinc finger nuclease" includes one ZFN as well as a pair of ZFNs that dimerize to cleave the target gene.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526. Artificial nucleases and transcription factors can include a TALE DNA-binding domain and a functional domain (nuclease domain for a TALEN or transcriptional regulatory domain for TALEN-TF). The term "TALEN" includes one TALEN as well as a pair of TALENs that dimerize to cleave the target gene.

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 8,568,526; 6,140,081; 6,453,242; and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. Nos. 8,586,526; 5,789, 538; 5,925,523; 6,007,988; 6,013,453; 6,200,759; WO 95/19431; WO 96/06166; WO 98/53057; WO 98/54311; WO 00/27878; WO 01/60970; WO 01/88197; WO 02/099084.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALEN proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer there between) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miR-NAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and – cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, U.S. Pat. Nos. 7,888,121; 7,914,796; 8,034,598 and 8,823,618, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "disease associated gene" is one that is defective in some manner in a monogenic disease. Non-limiting examples of monogenic diseases include severe combined immunodeficiency, cystic fibrosis, hemophilias, lysosomal storage diseases (e.g. Gaucher's, Hurler's, Hunter's, Fabry's, Neimann-Pick, Tay-Sach's etc.), sickle cell anemia, and thalassemia.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"GLA gene" encodes for α-galactosidase, an enzyme that breaks down globotriaosylceramide. Genetic mutation in the GLA gene results in defective enzyme function of α-galactosidase. The GLA gene is located at Xq22.1, which is the long (q) arm of the X chromosome at position 22.1. The GLA gene may also be referred to as AGAL_HUMAN, Agalsidase alpha, Alpha-D-galactosidase A, alpha-D-galactosidase galactohydrolase, Alpha-galactosidase, alpha-Galactosidase A, ceramidetrihexosidase, GALA, galactosidase, alpha, or Melibiase.

"Modulation" of gene expression refers to a change in the activity of a gene. Modulation of expression can include, but is not limited to, gene activation, gene optimization and gene repression. Genome editing (e.g., cleavage, alteration, inactivation, random mutation) can be used to modulate expression. Gene inactivation refers to any reduction in gene expression as compared to a cell that does not include a ZFP, TALE or CRISPR/Cas system as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., liver cells, muscle cells, RBCs, T-cells, etc.), including stem cells (pluripotent and multipotent).

"Red Blood Cells" (RBCs) or erythrocytes are terminally differentiated cells derived from hematopoietic stem cells. They lack a nuclease and most cellular organelles. RBCs contain hemoglobin to carry oxygen from the lungs to the peripheral tissues. In fact, 33% of an individual RBC is hemoglobin. They also carry $CO_2$ produced by cells during metabolism out of the tissues and back to the lungs for release during exhale. RBCs are produced in the bone marrow in response to blood hypoxia which is mediated by release of erythropoietin (EPO) by the kidney. EPO causes an increase in the number of proerythroblasts and shortens the time required for full RBC maturation. After approximately 120 days, since the RBC do not contain a nucleus or any other regenerative capabilities, the cells are removed from circulation by either the phagocytic activities of macrophages in the liver, spleen and lymph nodes (~90%) or by hemolysis in the plasma (~10%). Following macrophage engulfment, chemical components of the RBC are broken down within vacuoles of the macrophages due to the action of lysosomal enzymes. RBCs, in vitro or in vivo, can be descended from genetically modified stem or RBC precursor cells as described herein.

"Secretory tissues" are those tissues in an animal that secrete products out of the individual cell into a lumen of some type which are typically derived from epithelium.

Examples of secretory tissues that are localized to the gastrointestinal tract include the cells that line the gut, the pancreas, and the gallbladder. Other secretory tissues include the liver, tissues associated with the eye and mucous membranes such as salivary glands, mammary glands, the prostate gland, the pituitary gland and other members of the endocrine system. Additionally, secretory tissues include individual cells of a tissue type which are capable of secretion.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or Cas DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to up-regulate gene expression. When a fusion polypeptide in which a ZFP or TALE DNA-binding domain is fused to a cleavage domain, the ZFP or TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) Nature 340:245-246; U.S. Pat. No. 5,585,245 and International Patent Publication No. WO 98/44350.

A "vector" is capable of transferring gene sequences to target cells. Typically, "vector construct," "expression vector," "gene transfer vector," and "expression construct" mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the altered cells described herein and/or proteins produced by the altered cells described herein can be administered. Subjects of the present disclosure include those having an LSD.

Disclosed herein are methods and compositions for treating and/or preventing Fabry disease. The disclosure describes methods for insertion of a transgene sequence into a suitable target cell (e.g., a cell from a subject with Fabry disease) wherein the transgene encodes at least one protein (e.g., at least one α-GalA protein) that treats the disease. The methods may be in vivo (delivery of the transgene sequence to a cell in a living subject) or ex vivo (delivery of modified cells to a living subject). The disclosure also describes methods for the transfection and/or transduction of a suitable target cell with an expression system such that an α-GalA encoding transgene expresses a protein that treats (e.g., alleviates one or more of the symptoms associated with) the disease. The α-GalA protein may be excreted (secreted) from the target cell such that it is able to affect or be taken up by other cells that do not harbor the transgene (cross correction). The disclosure also provides for methods for the production of a cell (e.g., a mature or undifferentiated cell) that produces high levels of α-GalA where the introduction of a population of these altered cells into a patient will supply that needed protein to treat a disease or condition. In addition, provided are methods for the production of a cell (e.g. a mature or undifferentiated cell) that produces a highly active form (therapeutic) of α-GalA where the introduction of, or creation of, a population of these altered cells in a patient will supply that needed protein activity to treat (e.g., reduce or eliminate one or more symptoms) Fabry's disease. The highly active form of α-GalA produced as described herein can also be isolated from cells as described herein and administered to a patient in need thereof using standard enzyme replacement procedures known to the skilled artisan.

Described herein are methods and compositions for expressing at least one α galactosidase A (α-Gal A) protein.

The compositions and methods can be for use in vitro, in vivo or ex vivo, and comprise administering a GLA transgene (e.g., cDNA with wild-type or codon optimized GLA sequences) encoding at least one α-Gal A protein to the cell such that the α-Gal A protein is expressed in the cell. In certain embodiments, the cell is in a subject with Fabry's disease. In any of the methods described herein, the transgene can be administered to the liver of the subject. Optionally, the methods further comprise administering one or more nucleases that cleave an endogenous albumin gene in a liver cell in a subject such that the transgene is integrated into and expressed from the albumin gene. In any of the methods described herein, the α-Gal A protein expressed from the transgene can decrease the amount of glycospingolipids in the subject by at least about 2-fold as compared to untreated subjects or subjects treated with formulation buffer or other carrier. The GLA transgene may further comprise additional elements, including, for example, a signal peptide and/or one or more control elements. In certain embodiments, the GLA transgene (e.g., cDNA construct) further includes a wild-type or engineered WPRE sequence, for example a mutated WPRE sequence comprising the WPRE mut6 mutations described in Zanta-Boussif et al. (2009) *Gene Therapy* 16:605-619 and U.S. Pat. No. 10,179,918. In some embodiments, the mut6 mutations are made in the J04514 WPRE element, while in other embodiments, they are made in the J02442.1 WPRE (Ong et al. (2017) doi.org/10.1101/126904). In certain embodiments, the expression GLA construct comprises a construct as shown in FIG. 1B (variant #21). The WPRE-containing expression constructs as described herein result in improved transgene expression and activity as compared to expression constructs not including the WPRE sequences (e.g., 1-fold, 2-fold, 3-fold, 4-fold, 5-fold, 6-fold, 7-fold, 8-fold, 9-fold, 10-fold or more fold increased expression or activity). In certain embodiments, the expression construct is the one shown in Table 1.

In one aspect, the disclosure describes a method of expressing a transgene encoding one or more corrective GLA transgenes in a cell of the subject. The transgene may be inserted into the genome of a suitable target cell (e.g., blood cell, liver cell, brain cell, stem cell, precursor cell, etc.) such that the α-GalA product encoded by that corrective transgene is stably integrated into the genome of the cell (also referred to as a "IVPRP" approach) or, alternatively, the transgene may be maintained in the cell extra-chromosomally (also referred to as a "cDNA" approach). In one embodiment, the corrective GLA transgene is introduced (stably or extra-chromosomally) into cells of a cell line for the in vitro production of the replacement protein, which (optionally purified and/or isolated) protein can then be administered to a subject for treating a subject with Fabry disease (e.g., by reducing and/or eliminating one or more symptoms associated with Fabry disease). In certain embodiments, the α-GalA product encoded by that corrective transgene increases α-GalA activity in a tissue in a subject by any amount as compared to untreated subjects, for example, about 2- to about 2000-fold more (or any value therebetween) fold, including but not limited to 2 to 100 fold (or any value therebetween including 10-, 20-, 30-, 40-, 50-, 60-, 70-, 80-, 90-, 100-fold), 100- to 500-fold (or any value therebetween), 500- to 1000-fold (or any value therebetween), or 1000- to 2000-fold or more.

In another aspect, described herein are ex vivo or in vivo methods of treating a subject with Fabry disease (e.g., by reducing and/or eliminating one or more symptoms associated with Fabry disease), the methods comprising inserting an GLA transgene into a cell as described herein (cDNA and/or IVPRP approaches) such that the protein is produced in a subject with Fabry disease. In certain embodiments, the GLA transgene is part of a construct as shown in Table 1. In certain embodiments, isolated cells comprising the GLA transgene can be used to treat a patient in need thereof, for example, by administering the cells to a subject with Fabry disease. In other embodiments, the corrective GLA transgene is inserted into a target tissue in the body such that the replacement protein is produced in vivo. In some embodiments, the corrective transgene is inserted into the genome of cells in the target tissue, while in other preferred embodiments, the corrective transgene is inserted into the cells of the target tissue and is maintained in the cells extra-chromosomally. In any of the methods described herein, the expressed α-GalA protein may be excreted from the cell to act on or be taken up by secondary targets, including by other cells in other tissues (e.g. via exportation into the blood) that lack the GLA transgene (cross correction). In some instances, the primary and/or secondary target tissue is the liver. In other instances, the primary and/or secondary target tissue is the brain. In other instances, the primary and/or secondary target is blood (e.g., vasculature). In other instances, the primary and/or secondary target is skeletal muscle.

In certain embodiments, the methods and compositions described herein are used to decrease the amount of glycospingolipids including globotriaosylceramide (also known as GL-3 and Gb3) and globotriaosylsphingosine (lyso-Gb3), galabioasylceramide deposited in tissues of a subject suffering Fabry disease. In certain embodiments, the α-GalA product encoded by that corrective transgene decreases glycospingolipids in a tissue of a subject by any amount as compared to untreated subjects, for example, about 2-fold to about 100-fold more (or any value therebetween) fold, including but not limited to 2- to 100-fold (or any value therebetween including 10-, 20-, 30-, 40-, 50-, 60-, 70-, 80-, 90-, 100-fold). In certain embodiments, the α-GalA product encoded by that corrective transgene decreases glycospingolipids in a tissue of a subject by any amount as compared to untreated subjects, for example, at least about 10%, 20%, 30%, 40%, 50%, 60%, 70%, 80%, 90%, or about 100%.

In any of the methods described herein, the corrective GLA transgene comprises the wild type sequence of the functioning GLA gene, while in other embodiments, the sequence of the corrective GLA transgene is altered in some manner to give enhanced biological activity (e.g., optimized codons to increase biological activity and/or alteration of transcriptional and translational regulatory sequences to improve gene expression). In some embodiments, the GLA gene is modified to improve expression characteristics. Such modifications can include, but are not limited to, insertion of a translation start site (e.g. methionine), addition of an optimized Kozak sequence, insertion of a signal peptide, and/or codon optimization. In some embodiments, the signal peptide can be chosen from an albumin signal peptide, a F.IX signal peptide, an IDS signal peptide and/or an α-GalA signal peptide.

In certain aspects, the donors are cDNA donors. The cDNA donors typically include an enhancer sequence, a promoter sequence, an intron sequence, a signal peptide, the GLA coding sequence, a polyadenylation signal, and, optionally, a wild-type or mutated WPRE sequence. Non-limiting exemplary cDNA donors are shown schematically in FIG. 1A and FIG. 1B.

Any promoter, enhancer, intron, signal peptide, GLA-coding or polyA sequence and optional WPRE sequence can be sequence can be used in the cDNA constructs. In some embodiments, the enhancer and/or promoter are liver-specific, for example, comprised of a human ApoE enhancer and a human al-anti-trypsin (hAAT) promoter (Miao C H et al. (2000) *Mol. Ther.* 1(6): 522-532 (200)). In some embodiments, the liver specific promoter comprises one or more ApoE enhancer sequences (e.g., 1, 2, 3 and/or 4; see Okuyama et al (1996) Hum Gen Ther 7(5):637-45). In some embodiments, the promoter is linked to an intron. In some embodiments, the intron is an HBB-IGG chimeric intron comprising the 5' donor site from the first intron of the human β-globin gene and the branch and 3' acceptor site from the intron of an immunoglobulin gene heavy chain variable region. In some embodiments, the ApoE/hAAT promoter is specifically and highly active in hepatocytes, the intended target tissue, but is inactive in non-liver cell and tissue types; which reduces or prevents expression and activity in non-target tissues. In certain embodiments, the signal peptide comprises a GLA signal peptide and the polyadenylation signal comprises a SPA51 or bGH polyA sequence. The optional WPRE sequence can be any wild-type or mutated WPRE sequence. See, e.g., U.S. Pat. No. 10,179,918. In certain embodiments, the WPRE sequence comprises a mutated WPRE such as the mut6 WPRE sequence.

The cDNA expression vectors described herein can be delivered via any suitable vector, including on viral vectors such as AAV of any serotype (e.g., AAV2, AAV6 or AAV2/6).

In certain embodiments, the expression sequence (i.e., expression vector or expression construct) comprises the elements and sequence of variant #21, depicted in FIG. 1B, and as shown below in Table 1.

TABLE 1

| | | | Variant #21 cDNA elements and complete sequence |
|---|---|---|---|
| Element | Location | SEQ ID NO | Sequence |
| 5' ITR | 1-130 | 1 | CTGCGCGCTCGCTCGCTCACTGAGGCCGCCCGGGCAAAGCCCGGGCGTCG GGCGACCTTTGGTCGCCCGGCCTCAGTGAGCGAGCGAGCGCGCAGAGAGG GAGTGGCCAACTCCATCACTAGGGGTTCCT (SEQ ID NO: 1) |
| APOE Enhancer | 141-461 | 2 | AGGCTCAGAGGCACACAGGAGTTTCTGGGCTCACCCTGCCCCCTTCCAAC CCCTCAGTTCCCATCCTCCAGCAGCTGTTTGTGTGCTGCCTCTGAAGTCC ACACTGAACAAACTTCAGCCTACTCATGTCCCTAAAATGGGCAAACATTG CAAGCAGCAAACAGCAAACACACAGCCCTCCCTGCCTGCTGACCTTGGAG CTGGGGCAGAGGTCAGAGACCTCTCTGGGCCCATGCCACCTCCAACATCC |

TABLE 1-continued

| | | | |
|---|---|---|---|
| Element | Location | SEQ ID NO | Sequence |

Variant #21 cDNA elements and complete sequence

| Element | Location | SEQ ID NO | Sequence |
|---|---|---|---|
| | | | ACTCGACCCCTTGGAATTTCGGTGGAGAGGAGCAGAGGTTGTCCTGGCGT GGTTTAGGTAGTGTGAGAGGG (SEQ ID NO:2) |
| hAAT Promoter | 471-863 | 3 | GATCTTGCTACCAGTGGAACAGCCACTAAGGATTCTGCAGTGAGAGCAGA GGGCCAGCTAAGTGGTACTCTCCCAGAGACTGTCTGACTCACGCCACCCC CTCCACCTTGGACACAGGACGCTGTGGTTTCTGAGCCAGGTACAATGACT CCTTTCGGTAAGTGCAGTGGAAGCTGTACACTGCCCAGGCAAAGCGTCCG GGCAGCGTAGGCGGGCGACTCAGATCCCAGCCAGTGGACTTAGCCCCTGT TTGCTCCTCCGATAACTGGGGTGACCTTGGTTAATATTCACCAGCAGCCT CCCCCGTTGCCCCTCTGGATCCACTGCTTAAATACGGACGAGGACAGGGC CCTGTCTCCTCAGCTTCAGGCACCACCACTGACCTGGGACAGT (SEQ ID NO: 3) |
| HBB-IgG chimeric intron | 867-999 | 4 | GTAAGTATCAAGGTTACAAGACAGGTTTAAGGAGACCAATAGAAACTGGG CTTGTCGAGACAGAGAAGACTCTTGCGTTTCTGATAGGCACCTATTGGTC TTACTGACATCCACTTTGCCTTTCTCTCCACAG (SEQ ID NO: 4) |
| GLA cDNA | 1052-2341 | 5 | ATGCAACTTAGGAACCCCGAACTTCATCTTGGCTGCGCCCTGGCCCTCCG CTTCCTCGCTCTCGTTTCTTGGGACATCCCTGGCGCTAGGGCACTCGACA ACGGCCTCGCGCGGACTCCTACGATGGGATGGTTGCACTGGGAAAG GTTTATGTGCAATCTGGATTGCCAGGAGGAGCCGGACTCATGCATCTCGG AGAAGCTGTTCATGGAGATGGCGGAACTTATGGTATCGGAGGGATGGAAG GATGCCGGGTATGAGTATCTCTGTATCGACGATTGTTGGATGGCTCCCCA GAGAGACTCCGAGGGACGACTCCAAGCGGACCCCCAGCGCTTTCCACATG GCATTCGACAGCTCGCCAATTACGTGCACTCGAAGGGGTTGAAGTTGGGA ATCTACGCAGATGTGGGCAACAAAACGTGTGCGGGGTTCCCGGGGTCGTT TGGATACTACGATATTGATGCGCAGACGTTTGCTGACTGGGGTGTCGATC TTTTGAAATTTGATGGCTGTTACTGTGATTCGTTGGAAAACCTGGCGGAT GGATACAAGCATATGTCACTCGCCTTGAACCGGACAGGTCGCTCAATCGT ATACAGCTGCGAATGGCCCCTCTATATGTGGCCCTTCCAAAAGCCCAATT ACACAGAGATTCGGCAGTATTGCAATCACTGGAGGAACTTTGCCGATATT GACGACAGCTGGAAATCCATCAAGTCCATTCTCGATTGGACGAGCTTCAA CCAGGAGCGCATCGTGGACGTGGCAGGACCCGGAGGTTGGAACGATCCGG ACATGCTCGTAATTGGGAATTTCGGGCTTAGCTGGAATCAGCAAGTCACC CAAATGGCGCTGTGGGCCATCATGGCAGCTCCTCTCTTTATGTCGAATGA TCTGCGGCATATCTCGCCCCAGGCAAAGGCTCTTTTGCAAGACAAGGACG TCATCGCAATCAATCAGGACCCATTGGGGAAACAGGGATATCAACTTCGC CAGGGTGACAATTTCGAAGTATGGGAGAGGCCGCTTAGCGGGCTGGCGTG GGCGGTCGCGATGATTAACCGGCAGGAAATCGGAGGGCCTCGCTCGTATA CCATCGCAGTGGCCTCACTGGGCAAAGGAGTGGCGTGCAATCCGGCCTGC TTCATCACCCAGTTGTTGCCCGTCAAAAGAAAGCTGGGTTTCTACGAGTG GACATCCAGACTTAGATCACACATTAACCCTACTGGTACGGTGTTGCTCC AGCTCGAAAACACAATGCAGATGTCGTTGAAAGACCTGCTGTAA (SEQ ID NO: 5) |
| WPREmut6 J04514 | 2364-2955 | 6 | AATCAACCTCTGGATTACAAAATTTGTGAAAGATTGACTGGTATTCTTAA CTATGTTGCTCCTTTTACGCTATGTGGATACGCTGCTTTAATGCCTTTGT ATCATGCTATTGCTTCCCGTATGGCTTTCATTTTCTCCTCCTTGTGTATAAA TCCTGGTTGCTGTCTCTTTATGAGGAGTTGTGGCCCGTTGTCAGGCAACG TGGCGTGGTGTGCACTGTGTTTGCTGACGCAACCCCCACTGGTTGGGGCA TTGCCACCACCTGTCAGCTCCTTTCCGGGACTTTCGCTTTCCCCCTCCCT ATTGCCACGGCGGAACTCATCGCCGCCTGCCTTGCCCGCTGCTGGACAGG GGCTCGGCTGTTGGGCACTGACAATTCCGTGGTGTTGTCGGGGAAATCAT CGTCCTTTCCTTGGCTGCTCGCCTGTGTTGCCACCTGGATTCTGCGCGGG ACGTCCTTCTGCTACGTCCCTTCGGCCCTCAATCCAGCGGACCTTCCTTC CCGCGGCCTGCTGCCGGCTCTGCGGCCTCTTCCGCGTCTTCGCCTTCGCC CTCAGACGAGTCGGATCTCCCTTTGGGCCGCCTCCCCGCCTG (SEQ ID NO: 6) |
| bGH polyA | 2962-3186 | 7 | CTGTGCCTTCTAGTTGCCAGCCATCTGTTGTTTGCCCCTCCCCCGTGCCT TCCTTGACCCTGGAAGGTGCCACTCCCACTGTCCTTTCCTAATAAAATGA GGAAATTGCATCGCATTGTCTGAGTAGGTGTCATTCTATTCTGGGGGGTG GGGTGGGGCAGGACAGCAAGGGGGAGGATTGGGAAGACAATAGCAGGCAT GCTGGGGATGCGGTGGGCTCTATGG (SEQ ID NO: 7) |
| 3' ITR | 3214-3321 | 8 | AGGAACCCCTAGTGATGGAGTTGGCCACTCCCTCTCTGCGCGCTCGCTCG CTCACTGAGGCCGCCCGGGCTTTGCCCGGGCGGCCTCAGTGAGCGAGCGA GCGCGCAG (SEQ ID NO: 8) |

Complete transgene sequence:

(SEQ ID NO: 9)

ctgcgcgctc gctcgctcac tgaggccgcc cgggcaaagc ccgggcgtcg ggcgaccttt      60
ggtcgcccgg cctcagtgag cgagcgagcg cgcagagagg gagtggccaa ctccatcact     120

TABLE 1-continued

Variant #21 cDNA elements and complete sequence

|         |          | SEQ ID |          |
|---------|----------|--------|----------|
| Element | Location | NO     | Sequence | aggggttcct gcggcctagt aggctcagag gcacacagga gtttctgggc tcaccctgcc 180 cccttccaac ccctcagttc ccatcctcca gcagctgttt gtgtgctgcc tctgaagtcc 240 acactgaaca aacttcagcc tactcatgtc cctaaaatgg gcaaacattg caagcagcaa 300 acagcaaaca cacagccctc cctgcctgct gaccttggag ctggggcaga ggtcagagac 360 ctctctgggc ccatgccacc tccaacatcc actcgacccc ttggaatttc ggtggagagg 420 agcagaggtt gtcctggcgt ggtttaggta gtgtgagagg ggtacccggg gatcttgcta 480 ccagtggaac agccactaag gattctgcag tgagagcaga gggccagcta agtggtactc 540 tcccagagac tgtctgactc acgccacccc ctccaccttg gacacaggac gctgtggttt 600 ctgagccagg tacaatgact cctttcggta agtgcagtgg aagctgtaca ctgcccaggc 660 aaagcgtccg ggcagcgtag gcgggcgact cagatcccag ccagtggact tagcccctgt 720 ttgctcctcc gataactggg gtgaccttgg ttaatattca ccagcagcct cccccgttgc 780 ccctctggat ccactgctta aatacggacg aggacagggc cctgtctcct cagcttcagg 840 caccaccact gacctgggac agtcaggtaa gtatcaaggt tacaagacag gtttaaggag 900 accaatagaa actgggcttg tcgagacaga gaagactctt gcgtttctga taggcaccta 960 ttggtcttac tgacatccac tttgcctttc tctccacagg caattgatcc ccctgatctg 1020 cggcctcgac ggtatcgata agcttgccac catgcaactt aggaaccccg aacttcatct 1080 tggctgcgcc ctggccctcc gcttcctcgc tctcgtttct tgggacatcc ctggcgctag 1140 ggcactcgac aacggcctcg cgcggactcc tacgatggga tggttgcact gggaaaggtt 1200 tatgtgcaat ctggattgcc aggaggagcc ggactcatgc atctcggaga agctgttcat 1260 ggagatggcg gaacttatgg tatcggaggg atggaaggat gccgggtatg agtatctctg 1320 tatcgacgat tgttggatgg ctccccagag agactccgag ggacgactcc aagcggaccc 1380 ccagcgcttt ccacatggca ttcgacagct cgccaattac gtgcactcga aggggttgaa 1440 gttgggaatc tacgcagatg tgggcaacaa aacgtgtgcg gggttcccgg ggtcgtttgg 1500 atactacgat attgatgcgc agacgtttgc tgactggggt gtcgatcttt tgaaatttga 1560 tggctgttac tgtgattcgt tggaaaacct ggcggatgga tacaagcata tgtcactcgc 1620 cttgaaccgg acaggtcgct caatcgtata cagctgcgaa tggcccctct atatgtggcc 1680 cttccaaaag cccaattaca cagagattcg gcagtattgc aatcactgga ggaactttgc 1740 cgatattgac gacagctgga aatccatcaa gtccattctc gattggacga gcttcaacca 1800 ggagcgcatc gtggacgtgg caggacccgg aggttggaac gatccggaca tgctcgtaat 1860 tgggaatttc gggcttagct ggaatcagca agtcacccaa atggcgctgt gggccatcat 1920 ggcagctcct ctctttatgt cgaatgatct gcggcatatc tcgccccagg caaaggctct 1980 tttgcaagac aaggacgtca tcgcaatcaa tcaggaccca ttggggaaac agggatatca 2040 acttcgccag ggtgacaatt tcgaagtatg ggagaggccg cttagcgggc tggcgtgggc 2100 ggtcgcgatg attaaccggc aggaaatcgg agggcctcgc tcgtatacca tcgcagtggc 2160 ctcactgggc aaaggagtgg cgtgcaatcc ggcctgcttc atcacccagt gttgcccgt 2220 caaaagaaag ctgggtttct acgagtggac atccagactt agatcacaca ttaaccctac 2280 tggtacggtg ttgctccagc tcgaaaacac aatgcagatg tcgttgaaag acctgctgta 2340

TABLE 1-continued

Variant #21 cDNA elements and complete sequence

| Element | Location | SEQ ID NO | Sequence |
|---------|----------|-----------|----------|

```
atctagagga tctcgagaga tctaatcaac ctctggatta caaaatttgt gaaagattga 2400
ctggtattct taactatgtt gctcctttta cgctatgtgg atacgctgct ttaatgcctt 2460
tgtatcatgc tattgcttcc cgtatggctt tcattttctc ctccttgtat aaatcctggt 2520
tgctgtctct ttatgaggag ttgtggcccg ttgtcaggca acgtggcgtg gtgtgcactg 2580
tgtttgctga cgcaaccccc actggttggg gcattgccac cacctgtcag ctcctttccg 2640
ggactttcgc tttccccctc cctattgcca cggcggaact catcgccgcc tgccttgccc 2700
gctgctggac aggggctcgg ctgttgggca ctgacaattc cgtggtgttg tcggggaaat 2760
catcgtcctt tccttggctg ctcgcctgtg ttgccacctg gattctgcgc gggacgtcct 2820
tctgctacgt cccttcggcc ctcaatccag cggaccttcc ttcccgcggc ctgctgccgg 2880
ctctgcggcc tcttccgcgt cttcgccttc gccctcagac gagtcggatc tccctttggg 2940
ccgcctcccc gcctgggatc tctgtgcctt ctagttgcca gccatctgtt gtttgcccct 3000
cccccgtgcc ttccttgacc ctggaaggtg ccactcccac tgtcctttcc taataaaatg 3060
aggaaattgc atcgcattgt ctgagtaggt gtcattctat tctggggggt ggggtggggc 3120
aggacagcaa gggggaggat tgggaagaca atagcaggca tgctggggat gcggtgggct 3180
ctatggaccg gtctcgagat ccactagggc cgcaggaacc cctagtgatg gagttggcca 3240
ctccctctct gcgcgctcgc tcgctcactg aggccgcccg ggctttgccc gggcggcctc 3300
agtgagcgag cgagcgcgca g                                          3321
```

The expression construct of Table 1, which comprises a WPRE sequence, can be readily produced at clinical scale and has been shown to exhibit improved GLA activity, for example, at least about 3-fold, about 4-fold, about 5-fold, about 6-fold, about 7-fold about 8-fold, about 9-fold, about 10-fold, about 11-fold, about 12-fold, about 13-fold, about 14-fold, about 15-fold, about 16 fold, about 17-fold, about 18-fold, about 19-fold, about 20-fold as compared to expression constructs that do not include a WPRE sequence.

In another aspect, described herein is a nuclease (e.g., ZFN, ZFN pair, TALEN, TALEN pair and/or CRISPR/Cas system) expression vector comprising a polynucleotide, encoding one or more nucleases as described herein, operably linked to a promoter. In one embodiment, the expression vector is a viral vector. In a further aspect, described herein is a GLA expression vector comprising a polynucleotide encoding α-GalA as described herein, operably linked to a promoter. In one embodiment, the expression is a viral vector.

In another aspect, described herein is a host cell comprising one or more nucleases (e.g., ZFN, ZFN pair, TALEN, TALEN pair and/or CRISPR/Cas system) expression vectors and/or an α-GalA expression vector as described herein. The host cell may be stably transformed or transiently transfected or a combination thereof with one or more nuclease expression vectors. In some embodiments, the host cell is a liver cell.

In other embodiments, methods are provided for replacing a genomic sequence in any target gene with a therapeutic GLA transgene as described herein, for example using a nuclease (e.g., ZFN, ZFN pair, TALEN, TALEN pair and/or CRISPR/Cas system) (or one or more vectors encoding said nuclease) as described herein and a "donor" sequence or GLA transgene that is inserted into the gene following targeted cleavage with the nuclease. The GLA sequence may be present in the vector carrying the nuclease (or component thereof), present in a separate vector (e.g., Ad, AAV or LV vector or mRNA) or, alternatively, may be introduced into the cell using a different nucleic acid delivery mechanism. Such insertion of a donor nucleotide sequence into the target locus (e.g., highly expressed gene, disease associated gene, other safe-harbor gene, etc.) results in the expression of the GLA transgene under control of the target locus's (e.g., albumin, globin, etc.) endogenous genetic control elements. In some aspects, insertion of the GLA transgene, for example into a target gene (e.g., albumin), results in expression of an intact α-GalA protein sequence and lacks any amino acids encoded by the target (e.g., albumin). In other aspects, the expressed exogenous α-GalA protein is a fusion protein and comprises amino acids encoded by the GLA transgene and by the endogenous locus into which the GLA transgene is inserted (e.g., from the endogenous target locus or, alternatively from sequences on the transgene that encode sequences of the target locus). The target may be any gene, for example, a safe harbor gene such as an albumin gene, an AAVS1 gene, an HPRT gene; a CCR5 gene; or a highly-expressed gene such as a globin gene in an RBC precursor cell (e.g., beta globin or gamma globin). In some instances, the endogenous sequences will be present on the amino (N)-terminal portion of the exogenous α-GalA protein, while in others, the endogenous sequences will be present on the carboxy (C)-terminal portion of the exogenous α-GalA protein. In other instances, endogenous sequences will be present on both the N- and C-terminal portions of the α-GalA exogenous protein. In some embodiments, the endogenous sequences encode a secretion signal peptide that is removed during the process of secretion of the α-GalA protein from the cell. The endogenous sequences may include full-length wild-type or mutant endogenous sequences or, alternatively, may include partial endogenous amino acid sequences. In some embodiments, the endogenous gene-transgene fusion is located at the endogenous locus within the cell while in other embodiments, the endogenous sequence-transgene coding sequence is inserted into another locus within a genome (e.g., a GLA-transgene sequence inserted into an albumin, HPRT or CCR5 locus). In some embodiments, the GLA transgene is expressed such that a therapeutic α-GalA protein product is retained within the cell (e.g., precursor or mature cell). In other embodiments, the GLA transgene is fused to the extracellular domain of a membrane protein such that upon expression, a transgene α-GalA fusion will result in the surface localization of the therapeutic protein. In some aspects, the edited cells further comprise a trans-membrane protein to traffic the cells to a particular tissue type. In one aspect, the trans-membrane protein comprises an antibody, while in others, the trans-membrane protein comprises a receptor. In certain embodiments, the cell is a precursor (e.g., CD34+ or hematopoietic stem cell) or mature RBC (descended from a genetically modified GAL-producing cell as described herein). In some aspects, the therapeutic α-GalA protein product encoded on the transgene is exported out of the cell to affect or be taken up by cells lacking the transgene. In certain embodiments, the cell is a liver cell which releases the therapeutic α-GalA protein into the blood stream to act on distal tissues (e.g., kidney, spleen, heart, brain, skin, etc.).

In one embodiment, the GLA transgene is expressed from the albumin promoter following insertion into the albumin locus. The biologic encoded by the GLA transgene then may be released into the blood stream if the transgene is inserted into a hepatocyte in vivo. In some aspects, the GLA transgene is delivered to the liver in vivo in a viral vector through intravenous administration. In some embodiments, the donor GLA transgene comprises a Kozak consensus sequence prior to the α-GalA coding sequence (Kozak (1987) *Nucl Acid Res* 15(20):8125-48), such that the expressed product lacks the albumin signal peptide. In some embodiments, the donor α-GalA transgene contains an alternate signal peptide, such as that from the Albumin, IDS or F9 genes, in place of the native GLA signal sequence.

In a still further aspect, provided herein is a method for site specific integration of a nucleic acid sequence into an endogenous locus (e.g., disease-associated, highly expressed such as an albumin locus in a liver cell or globin locus in RBC precursor cells of a chromosome, for example into the chromosome of a non-human embryo. In certain embodiments, the method comprises: (a) injecting a non-human embryo with (i) at least one DNA vector, wherein the DNA vector comprises an upstream sequence and a downstream sequence flanking the α-GalA encoding nucleic acid sequence to be integrated, and (ii) at least one polynucleotide molecule encoding at least one nuclease (zinc finger, ZFN pair, TALE nuclease, TALEN pair or CRISPR/Cas system) that recognizes the site of integration in the target locus, and (b) culturing the embryo to allow expression of the nuclease (ZFN, TALEN, and/or CRISPR/Cas system, wherein a double stranded break introduced into the site of integration by the nuclease is repaired, via homologous recombination with the DNA vector, so as to integrate the nucleic acid sequence into the chromosome. In some embodiments, the polynucleotide encoding the nuclease is an RNA.

Nucleases

Any nuclease may be used in the practice of aspects of the methods described herein including but not limited to, at least one ZFNs, TALENs, homing endonucleases, and systems comprising CRISPR/Cas and/or Ttago guide RNAs, that are useful for in vivo cleavage of a donor molecule carrying a transgene and nucleases for cleavage of the genome of a cell such that the transgene is integrated into the genome in a targeted manner. Thus, described herein are compositions comprising one or more nucleases that cleave a selected gene, which cleavage results in genomic modification of the gene (e.g., insertions and/or deletions into the cleaved gene). In certain embodiments, one or more of the nucleases are naturally occurring. In other embodiments, one or more of the nucleases are non-naturally occurring, i.e., engineered in the DNA-binding molecule (also referred to as a DNA-binding domain) and/or cleavage domain. For example, the DNA-binding domain of a naturally occurring nuclease may be altered to bind to a selected target site (e.g., a ZFP, TALE and/or sgRNA of CRISPR/Cas that is engineered to bind to a selected target site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains). In other embodiments, the nuclease comprises a system such as the CRISPR/Cas of Ttago system.

DNA-Binding Domains

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG family ("LA-GLIDADG" disclosed as SEQ ID NO:10), the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Pat. No. 8,021,867. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et al (2007) *Science* 318:648-651). These proteins contain a DNA binding domain and a transcriptional activation domain. One of the most well characterized TAL-effectors is AvrBs3 from *Xanthomonas campestgris* pv. *vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 bp and the repeats are typically 91-100% homologous with each other (Bonas et al, ibid). Polymorphism of the repeats is usually located at positions 12 and 13 and there appears to be a one-to-one correspondence between the identity of the hypervariable diresidues (RVDs) at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). See, e.g., U.S. Pat. No. 8,586,526; Christian et al ((2010) *Genetics* epub 10.1534/genetics. 110.120717).

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature*

*Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; 7,888,121; 7,972,854; and U.S. Patent Publication No. 20050267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; and WO 01/88197. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 8,772,453; 6,479,626; 6,903,185; and 7,153,949 for exemplary linker sequences-. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970; WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding domain is part of a CRISPR/Cas nuclease system, including, for example a single guide RNA (sgRNA). See, e.g., U.S. Pat. Nos. 8,697,359 and 9,873,894. The CRISPR (clustered regularly interspaced short palindromic repeats) locus, which encodes RNA components of the system, and the Cas (CRISPR-associated) locus, which encodes proteins (Jansen et al., 2002. *Mol. Microbiol.* 43: 1565-1575; Makarova et al., 2002. *Nucleic Acids Res.* 30: 482-496; Makarova et al., 2006. *Biol. Direct* 1: 7; Haft et al., 2005. *PLoS Comput. Biol.* 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some cases, the cell does not naturally produce Cas protein and is genetically engineered to produce a Cas protein. Additional non-limiting examples of RNA guided nucleases that may be used in addition to and/or instead of Cas proteins include Class 2 CRISPR proteins such as Cpf1. See, e.g., Zetsche et al. (2015) *Cell* 163:1-13.

The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see Fagerlund et al, (2015) *Genom Bio* 16:251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "'Cas" includes both Cas9 and Cfp1 proteins. Thus, as used herein, a "CRISPR/Cas system" refers both CRISPR/Cas and/or CRISPR/Cfp1 systems, including both nuclease and/or transcription factor systems.

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov, et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). Ago from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37 degrees Celsius. TtAgo-RNA-mediated DNA cleavage could be used to affect a panoply of outcomes including gene knock-out, targeted gene addition, gene correction, targeted gene deletion using techniques standard in the art for exploitation of DNA breaks.

Thus, the nuclease comprises a DNA-binding domain in that specifically binds to a target site in any gene into which it is desired to insert a donor (transgene).

Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Natl Acad Sci USA* 93(3):1156-1160. The term "ZFN" includes a pair of ZFNs that dimerize to cleave the target gene. More recently, ZFNs have been used for genome modification in a variety of organisms. See, for example, U.S. Pat. Nos. 7,888,121; 8,409,861; 8,106, 255; and 9,447,434. Likewise, TALE DNA-binding domains have been fused to nuclease domains to create TALENs. See, e.g., U.S. Pat. No. 8,586,526. CRISPR/Cas nuclease systems comprising single guide RNAs (sgRNAs) that bind to DNA and associate with cleavage domains (e.g., Cas domains) to induce targeted cleavage have also been described. See, e.g., U.S. Pat. Nos. 8,697,359 and 8,932,814 and 9,873,894.

As noted above, the cleavage domain may be heterologous to the DNA-binding domain, for example a zinc finger DNA-binding domain and a cleavage domain from a nuclease or a TALEN DNA-binding domain and a cleavage domain from a nuclease; a sgRNA DNA-binding domain and a cleavage domain from a nuclease (CRISPR/Cas); and/or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, MA; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However, any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Pat. No. 7,888,121, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 8,772,453; 8,623,618; 8,409,861; 8,034,598; 7,914, 796; and 7,888,121, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" ("KK") and by mutating positions 486 (Q→E) and 499 (I→L) in another cleavage half-domain to produce an engineered cleavage half-domain designated "Q486E:I499L", ("EL"). The engineered cleavage half-domains described herein are obligate heterodimer mutants in which aberrant cleavage is minimized or abolished. U.S. Pat. Nos. 7,914,796 and 8,034,598, the disclosures of which are incorporated by reference in their entireties. In certain embodiments, the engineered cleavage half-domain comprises mutations at positions 486, 499 and 496 (numbered relative to wild-type FokI), for instance mutations that replace the wild type Gln (Q) residue at position 486 with a Glu(E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. No. 8,772,453. In other embodiments, the engineered cleavage half domain comprises the "Sharkey" mutations (see Guo et al, (2010) J. Mol. Biol. 400(1):96-107).

Engineered cleavage half-domains described herein can be prepared using any suitable method, for example, by site-directed mutagenesis of wild-type cleavage half-domains (Fok I) as described in U.S. Pat. Nos. 8,623,618; 8,409,861; 8,034,598; 7,914,796; and 7,888,121.

Methods and compositions are also used to increase the specificity of a nuclease pair for its intended target relative to other unintended cleavage sites, known as off-target sites (see U.S. Patent Publication No. 20170218349 and 20180087072). Thus, nucleases described herein can comprise mutations in one or more of their DNA binding domain backbone regions and/or one or more mutations in their nuclease cleavage domains. These nucleases can include mutations to amino acid within the ZFP DNA binding domain ('ZFP backbone') that can interact non-specifically with phosphates on the DNA backbone, but they do not comprise changes in the DNA recognition helices. Thus, the ZFP may include mutations of cationic amino acid residues in the ZFP backbone that are not required for nucleotide target specificity. In some embodiments, these mutations in the ZFP backbone comprise mutating a cationic amino acid residue to a neutral or anionic amino acid residue. In some embodiments, these mutations in the ZFP backbone comprise mutating a polar amino acid residue to a neutral or non-polar amino acid residue. In preferred embodiments, mutations at made at position (−5), (−9) and/or position (−14) relative to the DNA binding helix. In some embodiments, a zinc finger may comprise one or more mutations at (−5), (−9) and/or (−14). In further embodiments, one or more zinc finger in a multi-finger zinc finger protein may comprise mutations in (−5), (−9) and/or (−14). In some embodiments, the amino acids at (−5), (−9) and/or (−14) (e.g. an arginine (R) or lysine (K)) are mutated to an alanine (A), leucine (L), Ser (S), Asp (N), Glu (E), Tyr (Y) and/or glutamine (Q).

In certain embodiments, the engineered cleavage half domains are derived from the FokI nuclease domain and comprise a mutation in one or more of amino acid residues 416, 422, 447, 448, and/or 525, numbered relative to the wild-type full length FokI. In some embodiments, the mutations in amino acid residues 416, 422, 447, 448, and/or 525 are introduced into the FokI "ELD", "ELE", "KKK", "KKR", "KK", "EL", "KIK", "KIR" and/or Sharkey as described above.

Further, described herein are methods to increase specificity of cleavage activity through independent titration of the engineered cleavage half-domain partners of a nuclease complex. In some embodiments, the ratio of the two partners (half cleavage domains) is given at a 1:2, 1:3, 1:4, 1:5, 1:6, 1:8, 1:9, 1:10 or 1:20 ratio, or any value therebetween. In other embodiments, the ratio of the two partners is greater than 1:30. In other embodiments, the two partners are deployed at a ratio that is chosen to be different from 1:1. When used individually or in combination, the methods and compositions disclosed herein provide surprising and unexpected increases in targeting specificity via reductions in off-target cleavage activity. The nucleases used in these embodiments may comprise ZFNs, a pair of ZFNs, TALENs, a pair of TALENs, CRISPR/Cas, CRISPR/dCas and TtAgo, or any combination thereof.

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314. Expression of the nuclease may be under the control of a constitutive promoter or an inducible promoter, for example the galactokinase promoter which is activated (de-repressed) in the presence of raffinose and/or galactose and repressed in presence of glucose.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) Sciencexpress 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

Target Sites

As described in detail above, DNA domains can be engineered to bind to any sequence of choice in a locus, for example an albumin or other safe-harbor gene. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534, 261, incorporated by reference herein in their entireties. Rational design of TAL-effector domains can also be performed. See, e.g., U.S. Pat. No. 8,586,526.

Exemplary selection methods applicable to DNA-binding domains, including phage display and two-hybrid systems, are disclosed in U.S. Pat. Nos. 5,789,538; 5,925,523; 6,007, 988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Pat. Nos. 7,888,121 and 8,409, 891, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 9,567,609; 6,479,626; 6,903,185; and 7,153,949 for exemplary linker sequences 6 or more amino acids in length. The proteins described herein may include any combination of suitable linkers between the individual DNA-binding domains of the protein.

Donors

As noted above, methods and compositions for the introduction of an exogenous sequence (also called a "donor construct" or "donor sequence" or "donor") into a subject, for example to correct of a mutant gene or for increased expression of a gene encoding a protein lacking or deficient in Fabry disease (e.g., α-GalA), are provided.

It will be readily apparent that the donor sequence is typically not identical to the genomic sequence where it is placed. A donor sequence can contain a non-homologous sequence flanked by two regions of homology ("homology arms") to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

Described herein are methods of targeted insertion of a transgene encoding a α-GalA protein for insertion into a chosen location. The GLA transgene may encode a full-length α-GalA protein or may encode a truncated α-GalA protein. Polynucleotides for insertion can also be referred to as "exogenous" polynucleotides, "donor" polynucleotides or molecules or "transgenes." Non-limiting exemplary GLA donor constructs are shown in FIGS. 1A and 1B.

The donor polynucleotide can be DNA or RNA, single-stranded and/or double-stranded and can be introduced into a cell in linear or circular form. See, e.g., U.S. Pat. Nos. 8,703,489 and 9,255,259. The donor sequence(s) can also be contained within a DNA MC, which may be introduced into the cell in circular or linear form. See, e.g., U.S. Patent Publication No. 20140335063. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a viral or non-viral vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor may be inserted so that its expression is driven by the endogenous promoter at the integration site, namely the promoter that drives expression of the endogenous gene into which the donor is inserted (e.g., highly expressed, albumin, AAVS1, HPRT, etc.). However, it will be apparent that the donor may comprise a promoter and/or enhancer, for example a constitutive promoter or an inducible or tissue specific promoter. In some embodiments, the donor is maintained in the cell in an expression plasmid such that the gene is expressed extra-chromosomally.

The donor molecule may be inserted into an endogenous gene such that all, some or none of the endogenous gene is expressed. For example, a transgene as described herein may be inserted into an albumin or other locus such that some (N-terminal and/or C-terminal to the transgene encoding the lysosomal enzyme) or none of the endogenous albumin sequences are expressed, for example as a fusion with the transgene encoding the α-GalA protein(s). In other embodiments, the transgene (e.g., with or without additional coding sequences such as for albumin) is integrated into any endogenous locus, for example a safe-harbor locus.

When endogenous sequences (endogenous or part of the transgene) are expressed with the transgene, the endogenous sequences (e.g., albumin, etc.) may be full-length sequences (wild-type or mutant) or partial sequences. Preferably the endogenous sequences are functional. Non-limiting examples of the function of these full length or partial sequences (e.g., albumin) include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

Exogenous sequences linked to the transgene can also include signal peptides to assist in processing and/or secretion of the encoded protein. Non-limiting examples of these signal peptides include those from Albumin, IDS and Factor IX.

In certain embodiments, the exogenous sequence (donor) comprises a fusion of a protein of interest and, as its fusion partner, an extracellular domain of a membrane protein, causing the fusion protein to be located on the surface of the cell. This allows the protein encoded by the transgene to potentially act in the serum. In the case of Fabry disease, the α-GalA enzyme encoded by the transgene acts on the metabolic products that are accumulating in the serum from its location on the surface of the cell (e.g., RBC). In addition, if the RBC is engulfed by a splenic macrophage as is the normal course of degradation, the lysosome formed when the macrophage engulfs the cell would expose the membrane bound fusion protein to the high concentrations of metabolic products in the lysosome at the pH more naturally favorable to that enzyme. Non-limiting examples of potential fusion partners are shown below in Table 2.

TABLE 2

| Examples of potential fusion partners | |
| --- | --- |
| Name | Activity |
| Band 3 | Anion transporter, makes up to 25% of the RBC membrane surface protein |
| Aquaporin 1 | water transporter |
| Glut1 | glucose and L-dehydroascorbic acid transporter |
| Kidd antigen protein | urea transporter |
| RhAG | gas transporter |
| ATP1A1, ATP1B1 | Na+/K+ - ATPase |
| ATP2B1, ATP2B2, ATP2B3, ATP2B4 | Ca2+ - ATPase |
| NKCC1, NKCC2 | Na+ K+ 2Cl– - cotransporter |
| SLC12A3 | Na+—Cl– - cotransporter |
| SLC12A1, SLA12A2 | Na—K - cotransporter |
| KCC1 | K—Cl cotransporter |
| KCNN4 | Gardos Channel |

In some cases, the expression construct may comprise an endogenous GLA gene that has been modified. For instance, codon optimization may be performed on the endogenous gene. Furthermore, although antibody response to enzyme replacement therapy varies with respect to the specific therapeutic enzyme in question and with the individual patient, a significant immune response has been seen in many Fabry disease patients being treated with enzyme replacement with wild-type α-GalA. The transgene is considered to provide a therapeutic protein when it increases the amount of the protein (and/or its activity) as compared to subjects without the transgene. In addition, the relevance of these antibodies to the efficacy of treatment is also variable (see Katherine Ponder, (2008) *J Clin Invest* 118(8):2686). Thus, the methods and compositions described herein can comprise the generation of expression constructs with modified sequences as compared to wild-type GLA, including, but not limited to, modifications that produce functionally silent amino acid changes at sites known to be priming epitopes for endogenous immune responses, and/or truncations such that the polypeptide produced by such a sequence is less immunogenic.

Fabry disease patients often have neurological sequelae due the lack of the missing α-GalA enzyme in the brain. Unfortunately, it is often difficult to deliver therapeutics to the brain via the blood due to the impermeability of the blood brain barrier. Thus, the methods and compositions may be used in conjunction with methods to increase the delivery of the therapeutic into the brain, including but not limited to methods that cause a transient opening of the tight junctions between cells of the brain capillaries such as transient osmotic disruption through the use of an intracarotid administration of a hypertonic mannitol solution, the use of focused ultrasound and the administration of a bradykinin analogue (Matsukado et al (1996) *Neurosurgery* 39:125). Alternatively, therapeutics can be designed to utilize receptors or transport mechanisms for specific transport into the brain. Examples of specific receptors that may be used include the transferrin receptor, the insulin receptor or the low-density lipoprotein receptor related proteins 1 and 2 (LRP-1 and LRP-2). LRP is known to interact with a range of secreted proteins such as apoE, tPA, PAI-1 etc., and so fusing a recognition sequence from one of these proteins for LRP may facilitate transport of the enzyme into the brain, following expression in the liver of the therapeutic protein and secretion into the blood stream (see Gabathuler, (2010) ibid).

Cells

Genetically modified cells (e.g., stem cells, precursor cells, liver cells, muscle cells, etc.) comprising an exogenous GLA transgene (integrated or extrachromosomal) are also provided, including cells made by the methods described herein. These cells can be used to provide an α-Gal A protein to a subject with Fabry disease, for example by administering the cell(s) to a subject in need thereof or, alternatively, by isolating the α-Gal A protein produced by the cell and administering the protein to the subject in need thereof (enzyme replacement therapies). Alternatively, the cells may be generated in vivo in the subject by administration of the expression constructs as described herein. Thus, isolated and in vivo genetically modified cells are provided. Also provided are vectors (e.g., viral vectors such as AAV or Ad or lipid nanoparticles) comprising a GLA transgene for use in any of the methods described herein, including for use in treatment of Fabry disease.

In any of the methods described herein, the GLA transgene may be inserted into the genome of a target cell using a nuclease. Non-limiting examples of suitable nucleases include zinc-finger nucleases (ZFNs), TALENs (Transcription activator like protein nucleases) and/or CRISPR/Cas nuclease systems, which include a DNA-binding molecule that binds to a target site in a region of interest (e.g., a disease associated gene, a highly-expressed gene, an albumin gene or other safe harbor gene) in the genome of the cell and one or more nuclease domains (e.g., cleavage domain and/or cleavage half-domain). Cleavage domains and cleavage half domains can be obtained, for example, from various restriction endonucleases, Cas proteins and/or homing endonucleases. In certain embodiments, the zinc finger domain recognizes a target site in an albumin gene or a globin gene in red blood precursor cells (RBCs). See, e.g., U.S. Pat. No. 9,877,988, incorporated by reference in its entirety herein. In other embodiments, the nuclease (e.g., ZFN, TALEN, and/or CRISPR/Cas system) binds to and/or cleaves a safe-harbor gene, for example a CCR5 gene, a PPP1R12C (also known as AAVS1) gene, albumin, HPRT or a Rosa gene. See, e.g., U.S. Pat. Nos. 9,877,988; 9,567,573; 9,447,434; 9,394,545; 9,222,105; 9,206,404; 9,150,847; 8,895,264; 8,771,985; 8,106,255; 7,888,121; 7,972,854; 7,914,796; 7,951,925; 8,110,379; 8,409,861; and 8,586,526; U.S. Patent Publications 20030232410 and 20060063231. The nucleases (or components thereof) may be provided as a polynucleotide encoding one or more nucleases (e.g., ZFN, TALEN, and/or CRISPR/Cas system) described herein. The polynucleotide may be, for example, mRNA. In some aspects, the mRNA may be chemically modified (See e.g. Kormann et al, (2011) *Nature Biotechnology* 29(2):154-157). In other aspects, the mRNA may comprise an ARCA cap (see U.S. Pat. Nos. 7,074,596 and 8,153,773). In further embodiments, the mRNA may comprise a mixture of unmodified and modified nucleotides (see U.S. Patent Publication 20120195936). In still further embodiments, the mRNA may comprise a WPRE element (see U.S. Pat. No. 10,179,918).

In another aspect, genetically modified cells (e.g., stem cells, precursor cells, liver cells, muscle cells, etc.) with the desired GLA transgene (optionally integrated using a nuclease) are described. In some aspects, the edited stem or precursor cells are then expanded and may be induced to differentiate into a mature edited cells ex vivo, and then the cells are given to the patient. Thus, cells descended from the genetically edited (modified) GLA-producing stem or precursor cells as described herein may be used. In other aspects, the edited precursors (e.g., CD34+ stem cells) are given in a bone marrow transplant which, following successful implantation, proliferate producing edited cells that then differentiate and mature in vivo and contain the biologic expressed from the GLA transgene. In some embodiments, the edited CD34+ stem cells are given to a patient intravenously such that the edited cells migrate to the bone marrow, differentiate and mature, producing the α-Gal A protein. In other aspects, the edited stem cells are muscle stem cells which are then introduced into muscle tissue. In some aspects, the engineered nuclease is a Zinc Finger Nuclease (ZFN) (the term "ZFN" includes a pair of ZFNs) and in others, the nuclease is a TALE nuclease (TALEN) (the term "TALENs" include a pair of TALENs), and in other aspects, a CRISPR/Cas system is used. The nucleases may be engineered to have specificity for a safe harbor locus, a gene associated with a disease, or for a gene that is highly expressed in cells. By way of non-limiting example only, the safe harbor locus may be the AAVS1 site, the CCR5 gene, albumin or the HPRT gene while the disease associated gene may be the GLA gene encoding α-galactosidase A.

The GLA transgene may be full-length or modified and can be expressed extra-chromosomally or can be integrated in a targeted manner into the cell's genome using one or more nucleases. Unlike random integration, nuclease-mediated targeted integration ensures that the transgene is integrated into a specified gene. The transgene may be integrated anywhere in the target gene. In certain embodiments, the transgene is integrated at or near the nuclease binding and/or cleavage site, for example, within 1-300 (or any number of base pairs therebetween) base pairs upstream or downstream of the site of cleavage and/or binding site, more preferably within 1-100 base pairs (or any number of base pairs therebetween) of either side of the cleavage and/or binding site, even more preferably within 1 to 50 base pairs (or any number of base pairs therebetween) of either side of the cleavage and/or binding site. In certain embodiments, the integrated sequence does not include any vector sequences (e.g., viral vector sequences).

Any cell type can be genetically modified as described herein to comprise a transgene, including but not limited to cells or cell lines. Other non-limiting examples of genetically modified cells as described herein include T-cells (e.g., CD4+, CD3+, CD8+, etc.); dendritic cells; B-cells; autologous (e.g., patient-derived), muscle cells, brain cells and the like. In certain embodiments, the cells are liver cells and are modified in vivo. In certain embodiments, the cells are stem cells, including heterologous pluripotent, totipotent or multipotent stem cells (e.g., CD34+ cells, induced pluripotent stem cells (iPSCs), embryonic stem cells or the like). In certain embodiments, the cells as described herein are stem cells derived from patient.

The cells as described herein are useful in treating and/or preventing Fabry disease in a subject with the disorder, for example, by in vivo therapies. Ex vivo therapies are also provided, for example when the nuclease-modified cells can be expanded and then reintroduced into the patient using standard techniques. See, e.g., Tebas et al (2014) *New Eng J Med* 370(10):901. In the case of stem cells, after infusion into the subject, in vivo differentiation of these precursors into cells expressing the functional protein (from the inserted donor) also occurs.

Pharmaceutical compositions comprising the cells as described herein are also provided. In addition, the cells may be cryopreserved prior to administration to a patient.

Delivery

The cDNA expression constructs, nucleases, polynucleotides encoding these nucleases, donor polynucleotides and/or compositions (e.g., cells, proteins, polynucleotides, etc.) described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Expression constructs and/or nucleases as described herein may also be delivered using vectors containing sequences encoding one or more of the zinc finger, TALEN and/or Cas protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce cDNA expression constructs or nucleic acids encoding nucleases and/or expression constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, Nature 357:455-460 (1992); Van Brunt, *Biotechnology* 6(10):1149-1154 (1988); Vigne, *Restorative Neurology and Neuroscience* 8:35-36 (1995);

Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid: nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Maryland), BTX Molecular Delivery Systems (Holliston, MA) and Copernicus Therapeutics Inc, (see for example U.S. Pat. No. 6,008, 336). Lipofection is described in e.g., U.S. Pat. Nos. 5,049, 386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485, 054, 4,501,728, 4,774,085, 4,837,028, and 4,946,787).

The cDNAs and/or nuclease compositions described herein can also be delivered using nanoparticles, for example lipid nanoparticles (LNP). See, e.g., Lee et al (2016) *Am J Cancer Res* 6(5):1118-1134; U.S. Pat. No. 10,166,298; and U.S. Publication No. 20180185516.

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to subjects (in vivo) or they can be used to treat cells in vitro and the modified cells are administered to subjects (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991)).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including by non-limiting example, AAV1, AAV3, AAV4, AAV5, AAV6, AAV8, AAV 8.2, AAV9, and AAV rh10 and pseudotyped AAV such as AAV2/8, AAV2/5 and AAV2/6 can also be used.

AAV may be manufactured at a clinical scale by a number of different processes. Examples of systems that can be used include (1) plasmid DNA transfection in mammalian cells, (2) Ad infection of stable mammalian cell lines, (3) infection of mammalian cells with recombinant herpes simplex viruses (rHSVs), and (4) infection of insect cells (Sf9 cells) with recombinant baculoviruses (see Penaud-Budloo et al. (2018) *Mol Ther Methods Clin Dev.* 8: 166-180 for a review).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs (expression constructs) can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

It will be apparent that the nuclease-encoding sequences and donor constructs can be delivered using the same or different systems. For example, a donor polynucleotide can be carried by a plasmid, while the one or more nucleases can be carried by an AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The methods disclosed herein contemplate the treatment and/or prevention of Fabry disease (e.g. lysosomal storage disease). Treatment can comprise insertion of the corrective disease associated GLA transgene in safe harbor locus (e.g. albumin) in a cell for expression of the needed enzyme and release into the blood stream. The corrective α-GalA encoding transgene may encode a wild type or modified protein; and/or may comprise a codon optimized GLA transgene; and/or a transgene in which epitopes may be removed without functionally altering the protein. In some cases, the methods comprise insertion of an episome expressing the α-GalA encoding transgene into a cell for expression of the needed enzyme and release into the blood stream. Insertion into a secretory cell, such as a liver cell for release of the product into the blood stream, is particularly useful. The methods and compositions also can be used in any circumstance wherein it is desired to supply a GLA transgene encoding one or more therapeutics in a hematopoietic stem cell such that mature cells (e.g., RBCs) derived from (descended from) these cells contain the therapeutic α-GalA protein. These stem cells can be differentiated in vitro or in vivo and may be derived from a universal donor type of cell which can be used for all patients. Additionally, the cells may contain a transmembrane protein to traffic the cells in the body. Treatment can also comprise use of patient cells containing the therapeutic transgene where the cells are developed ex vivo and then introduced back into the patient. For example, HSC containing a suitable α-GalA encoding transgene may be inserted into a patient via a bone marrow transplant. Alternatively, stem cells such as muscle stem cells or iPSC which have been edited using with the α-GalA encoding transgene maybe also injected into muscle tissue.

Thus, this technology may be of use in a condition where a patient is deficient in some protein due to problems (e.g., problems in expression level or problems with the protein expressed as sub- or non-functioning). Particularly useful is the expression of transgenes to correct or restore functionality in subjects with Fabry disease.

By way of non-limiting examples, different methods of production of a functional α-Gal A protein to replace the defective or missing α-Gal A protein is accomplished and used to treat Fabry disease. Nucleic acid donors encoding the proteins may be inserted into a safe harbor locus (e.g. albumin or HPRT) and expressed either using an exogenous promoter or using the promoter present at the safe harbor. Especially useful is the insertion of a GLA transgene in an albumin locus in a liver cell, where the GLA transgene further comprises sequences encoding a signal peptide that mediates the secretion of the expressed α-Gal A protein from the liver cell into the blood stream. Alternatively, donors can be used to correct the defective gene in situ. The desired α-GalA encoding transgene may be inserted into a CD34+ stem cell and returned to a patient during a bone marrow transplant. Finally, the nucleic acid donor maybe be inserted into a CD34+ stem cell at a beta globin locus such that the mature red blood cell derived from this cell has a high concentration of the biologic encoded by the nucleic acid donor. The biologic-containing RBC can then be targeted to the correct tissue via transmembrane proteins (e.g. receptor or antibody). Additionally, the RBCs may be sensitized ex vivo via electrosensitization to make them more susceptible to disruption following exposure to an energy source (see WO2002007752).

In some applications, an endogenous gene may be knocked out by use of methods and compositions described herein. Examples of this aspect include knocking out an aberrant gene regulator or an aberrant disease associated gene. In some applications, an aberrant endogenous gene may be replaced, either functionally or in situ, with a wild type version of the gene. The inserted gene may also be altered to improve the expression of the therapeutic α-GalA protein or to reduce its immunogenicity. In some applications, the inserted α-GalA encoding transgene is a fusion protein to increase its transport into a selected tissue such as the brain.

It will be appreciated that suitable GLA donors are not limited to the ones exemplified below but include any GLA transgene.

The disclosure also supplies methods and compositions for the production of a cell (e.g., RBC) carrying an α-GalA therapeutic protein for treatment of Fabry disease that can be used universally for all patients as an allogenic product. This allows for the development of a single product for the treatment of patients with Fabry disease, for example. These carriers may comprise trans-membrane proteins to assist in the trafficking of the cell. In one aspect, the trans-membrane protein comprises an antibody, while in others, the trans-membrane protein comprises a receptor.

In some embodiments, the GLA transgene donor is transfected or transduced into a cell for episomal or extra-chromosomal maintenance of the transgene. In some aspects, the GLA transgene donor is maintained on a vector comprising regulatory domains to regulate expression of the transgene donor. In some instances, the regulatory domains to regulate transgene expression are the domains endogenous to the transgene being expressed while in other instances, the regulatory domains are heterologous to the transgene. In some embodiments, the GLA transgene is maintained on a viral vector, while in others, it is maintained on a plasmid or mini circle. In some embodiments, the viral vector is an AAV, Ad or LV. In further aspects, the vector comprising the transgene donor is delivered to a suitable target cell in vivo, such that the α-GalA therapeutic protein encoded by the transgene donor is released into the blood stream when the transgene donor vector is delivered to a hepatocyte.

In another embodiment, the disclosure describes precursor cells (muscle stem cells, progenitor cells or CD34+ hematopoietic stem cell (HSPC) cells) into which the GLA transgene has been inserted such that mature cells derived from these precursors contain high levels of the α-GalA product encoded by the transgene. In some embodiments, these precursors are induced pluripotent stem cells (iPSC).

In some embodiments, the methods may be used in vivo in transgenic animal systems. In some aspects, the transgenic animal may be used in model development where the transgene encodes a human α-GalA protein. In some instances, the transgenic animal may be knocked out at the corresponding endogenous locus, allowing the development of an in vivo system where the human protein may be studied in isolation. Such transgenic models may be used for screening purposes to identify small molecules, or large biomolecules or other entities which may interact with or modify the human protein of interest. In some aspects, the GLA transgene is integrated into the selected locus (e.g., highly expressed or safe-harbor) into a stem cell (e.g., an embryonic stem cell, an induced pluripotent stem cell, a hepatic stem cell, a neural stem cell etc.) or non-human animal embryo obtained by any of the methods described herein and those standard in the art, and then the embryo is implanted such that a live animal is born. The animal is then raised to sexual maturity and allowed to produce offspring wherein at least some of the offspring comprise the integrated GLA transgene.

In any of the previous embodiments, the methods and compounds may be combined with other therapeutic agents for the treatment of subjects with Fabry disease. In some embodiments, the methods and compositions include the use of a molecular chaperone (Hartl et al (2011) *Nature* 465: 324-332) to insure the correct folding of the Fabry protein. In some aspects, the chaperone can be chosen from well-known chaperone proteins such as AT1001 (Benjamin et al (2012) *Mol Ther* 20(4):717-726), AT2220 (Khanna et al (2014) *PLoS ONE* 9(7): e102092, doi:10.1371), and Migalastat (Benjamin et al (2016) *Genet Med* doi: 10.1038/gim.2016.122). In some aspects, the methods and compositions are used in combination with methods and compositions to allow passage across the blood brain barrier. In other aspects, the methods and compositions are used in combination with compounds known to suppress the immune response of the subject.

A kit, comprising a nuclease system and/or a GLA donor as described herein is also provided. The kit may comprise nucleic acids encoding the one or more nucleases (ZFNs, ZFN pairs, TALENs, TALEN pairs and/or CRISPR/Cas system), (e.g. RNA molecules or the ZFN, TALEN, and/or CRISPR/Cas system encoding genes contained in a suitable expression vector), donor molecules, expression vectors encoding the single-guide RNA suitable host cell lines, instructions for performing the methods disclosed herein, and the like.

These and other aspects will be readily apparent to the skilled artisan in light of the disclosure as a whole.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control. Generally, nomenclature used in connection with, and techniques of, cardiology, medicine, medicinal and pharmaceutical chemistry, and cell biology described herein are those well-known and commonly used in the art. Enzymatic reactions and purification techniques are performed according to manufacturer's specifications, as commonly accomplished in the art or as described herein. Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers. All publications and other references mentioned herein are incorporated by reference in their entirety. Although a number of documents are cited herein, this citation does not constitute an admission that any of these documents forms part of the common general knowledge in the art. As used herein, the term "approximately" or "about" as applied to one or more values of interest refers to a value that is similar to a stated reference value. In certain embodiments, the term refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context.

In order that this invention may be better understood, the following examples are set forth. These examples are for purposes of illustration only and are not to be construed as limiting the scope of the invention in any manner.

Example 1

High Plasma α-Gal a Activity in GLAKO Mice Treated with Variant #4 Expression Construct, Sustained for 3 Months Samples of variant #4 expression construct, as shown in FIG. 1A, were administered to male GLAKO mice to evaluate the pharmacodynamic activity and biodistribution following a single IV dose.

GLAKO male mice were 8-12 weeks old at study initiation. The animals (n=10-20 males/group) received formulation buffer comprising phosphate buffered saline (PBS) containing CaCl2, MgCl2, NaCl, Sucrose and Kolliphor® P 188 (Poloxamer 188) (control mice) or one of three dose levels of variant #4 expression vector (2.0E+12, 5.0E+12, or 5.0E+13 vg/kg, respectively; n=10/group) as a single 200 μl IV tail administration on Day 1. The mice were monitored for 3 months. The results of the pharmacokinetic evaluations (plasma α-Gal A activity) are presented in FIG. 2 for the individual mice and the group averages (mean+SD) are presented in FIG. 3. As shown, plasma α-Gal A activity scaled with AAV/construct dose. In addition, plasma α-Gal A activity reached over 300-fold that of the physiological normal or α-Gal A activity in a wild type (non-mutated) subject. (The * in FIG. 3 indicates that one outlier was removed due to overperformance).

One-time administration of increasing amounts of AAV hGLA cDNA lacking the WPRE (variant #4) was made using a clinical scale manufacturing process and resulted in supraphysiological expression of plasma α-GalA (over 300-fold of WT) by study day 15, was well tolerated, and was stable for 3 months post-injection. Dose-dependent increases in α-GalA activities were achieved in liver, heart and kidney with a corresponding reduction of Gb3/lyso-Gb3.

Figures 4A, 4B, 4C:
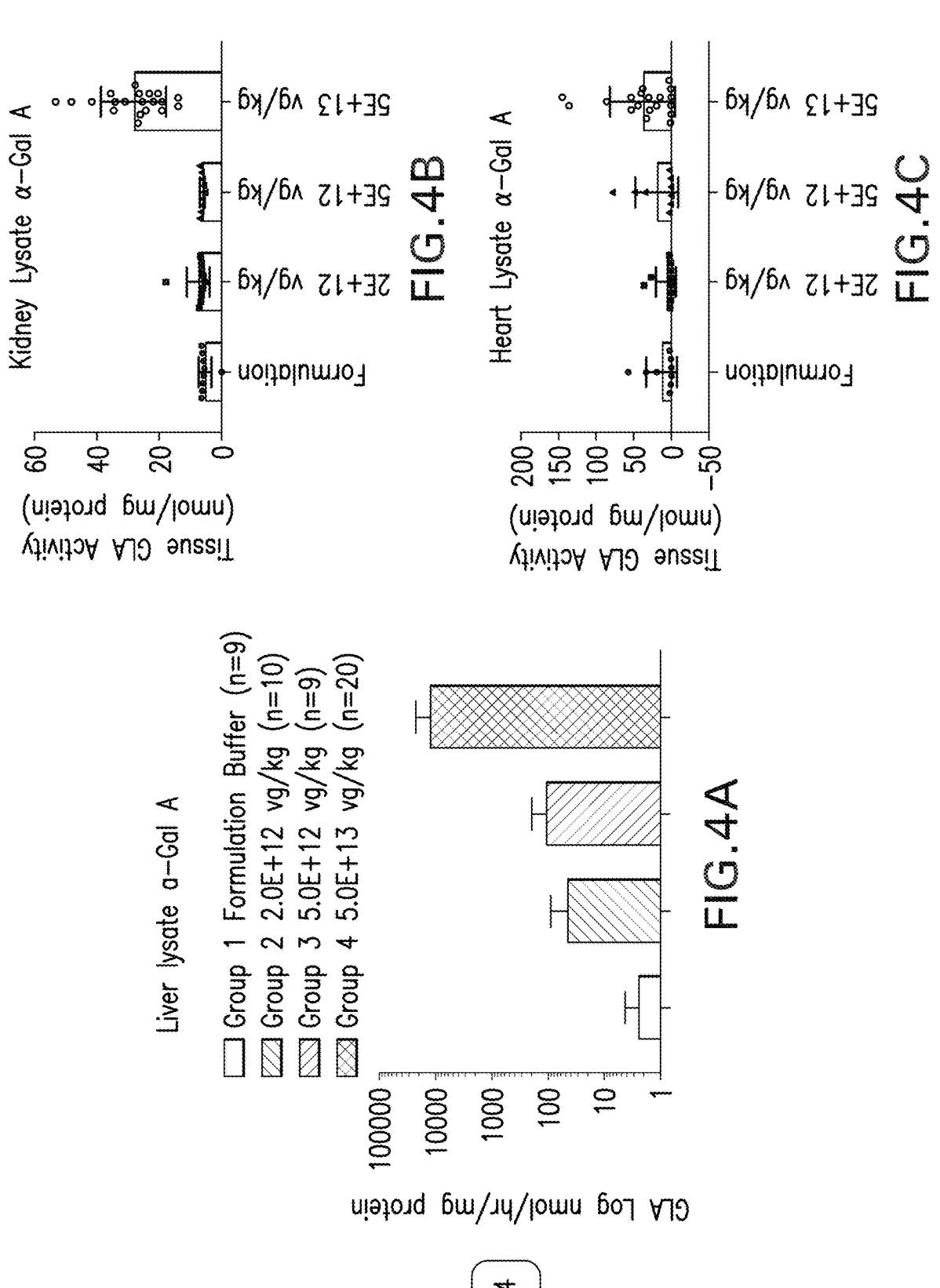
FIG. 4A is a graph showing α-Gal A activity in liver lysates of the indicated groups of animals treated with variant #4 expression constructs or control animals. Group 2 was administered 2.0E+12 vg/kg, Group 3 was administered 5.0E+12 vg/kg, and Group 4 was administered 5.0E+13 vg/kg.
FIG. 4B is a graph showing α-Gal A activity in kidney lysates of the indicated groups of animals treated with expression constructs (variant #4 expression construct) or control animals. Group 2 was treated with constructs at a dose of 2.0E+12 vg/kg, Group 3 was treated with constructs at a dose of 5.0E+12 vg/kg, and Group 4 was treated with constructs at a dose of 5.0E+13 vg/kg.
FIG. 4C is a graph showing α-Gal A activity in heart lysates of the indicated groups of animals treated with expression constructs (variant #4 expression construct) or control animals. Group 2 was administered 2.0E+12 vg/kg, Group 3 was administered 5.0E+12 vg/kg, and Group 4 was administered 5.0E+13 vg/kg.

Liver-produced α-Gal A was secreted into the bloodstream and taken up by secondary tissue. FIG. 4A shows tissue α-Gal A activity in liver lysates. FIG. 4B shows tissue α-Gal A activity in kidney lysates. FIG. 4C shows tissue α-Gal A activity in heart lysates.

Example 2

High Levels of α-Gal a Activity Results in a Corresponding Decrease of Fabry Substrates Variant #4 construct formulation was administered IV into GLAKO mice at doses of 0 vg/kg, 2.0E+12 vg/kg, 5.0E+12 vg/kg or 5.0E+13 vg/kg to evaluate the level of Fabry substrates in mouse plasma and tissue. Tissues were harvested at necropsy on Day 91 postdosing and assayed for levels of α-Gal A substrate Gb3 (isoforms C22:0 and C24:0) and its deacylated form lyso-Gb3 using LC-MS. Briefly, tissues were weighed and mechanically disrupted in tissue destruction fluid (5% MeOH, 95% water and 0.1% ascetic acid) at a ratio of 5 ml fluid per mg of tissue. 10 μl of plasma or tissue slurry were then added to 90 μl of precipitation solvent (MeOH with internal standard N-Tricosanoyl ceramide trihexoside (C23:0, Matreya) spiked into solution) in a siliconized tube, vortexed and placed on a shaking plate at room temp for 30 minutes. Samples were then centrifuged and 10 μl of sample added to 90 μl of single blank matrix (DMSO/MeOH 1:1+0.1% FA) in glass LC-MS vial. Samples were analyzed for Gb3 chain length 24:0, the predominant Gb3 species present in GLAKO mice and measured against a standard curve composed of ceramide trihexoside (Gb3, Matreya).

Globotriaosylsphingosine (lyso-Gb3) was measured in a similar manner using Glucosylsphingosine (Matreya) as the internal standard and Lyso-Ceramide trihexoside (lyso-Gb3, Matreya) to create the standard curve. Data represent mean+ SD of 9 to 20 animals/group as indicated in the legend. Fabry substrate globotriaosylceramide (Gb3) was measured in selected murine plasma and tissues via mass spectrometry.

Figures 5A, 5B:
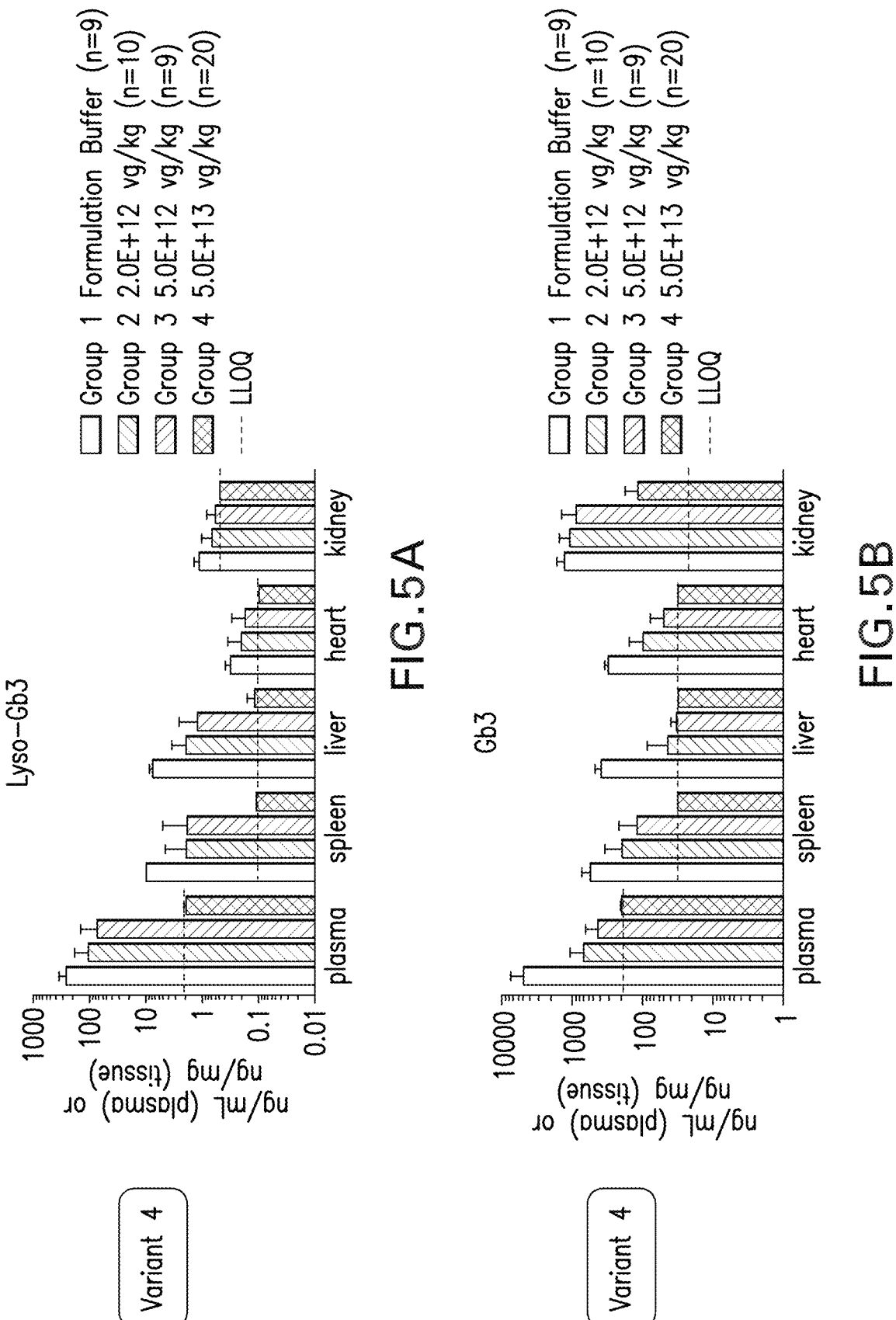
FIG. 5A is a graph showing Lyso-Gb3 substrate concentrations in plasma, spleen, liver, heart and kidney in the indicated groups of GLAKO mice treated with expression constructs (variant #4 expression construct) or control animals at day 91 following treatment. For each tissue, bars left to right show Group 1 animals which received Formulation Buffer, Group 2 which received constructs at a dose of 2.0E+12 vg/kg (10 animals); Group 3 which received constructs at a dose of 5.0E+12 vg/kg (9 animals); and Group 4 which received constructs at a dose of 5.0E+13 vg/kg (20 animals). As shown, Lyso-Gb3 substrate concentrations are lower in Groups 2 through 4 as compared to the control Group 1 in all of the tissues tested. Also shown by a dashed line is lower limit of quantification (LLOQ).
FIG. 5B is a graph showing Gb3 levels in plasma, spleen, liver, heart and kidney in the indicated Groups of animals treated with expression constructs (variant #4) or control animals. For each tissue, bars left to right show Group 1 animals which received Formulation Buffer, Group 2 which received constructs at a dose of 2.0E+12 vg/kg (10 animals); Group 3 which received constructs at a dose of 5.0E+12 vg/kg (9 animals); and Group 4 which received constructs at a dose of 5.0E+13 vg/kg (20 animals). As shown, Gb3 substrate concentrations are lower in Groups 2 through 4 as compared to the control Group 1 in all of the tissues tested. Also shown by a dashed line is lower limit of quantification (LLOQ).

The constant production of α-Gal A should enable reduction and potentially clearance of Fabry disease substrates, Gb3 and lyso-Gb3. A dose-related decrease in the levels of Fabry substrate Gb3 and lyso-Gb3 was found in plasma, liver, heart, kidney and spleen, as shown in FIG. 5A and FIG. 5B. Most samples of animals in the high dose group had tissue Gb3 levels reduced by 80% or more, compared to the samples of animals in the formulation control group, as shown in FIG. 5B.

Figures 6A, 6B:
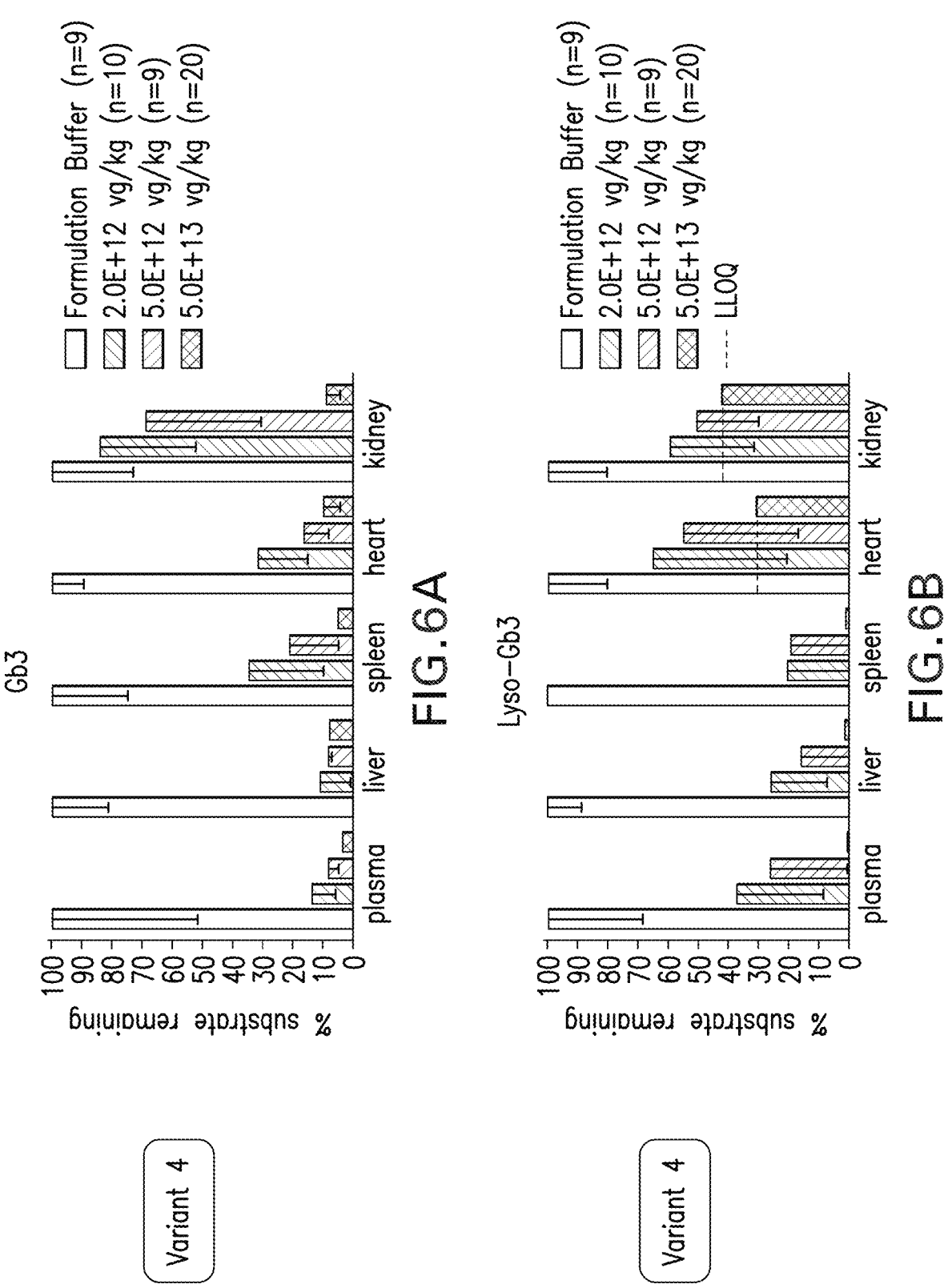
FIG. 6A is a graph showing the percent of Gb3 and Lyso-Gb3 substrate remaining in plasma, spleen, liver, heart and kidney in the indicated Group of animals treated with variant #4 expression construct or control animals.
FIG. 6B is a graph showing the percent of Gb3 and Lyso-Gb3 substrate remaining in plasma, spleen, liver, heart and kidney in the indicated Group of animals treated with variant #4 expression construct or control animals.

At the high dose level, Gb3 levels in the heart and kidney were reduced to about 10% of untreated animals, as shown in FIG. 6A. In the treated subjects, Gb3 levels were below the lower level of quantitation, as shown in FIG. 6B.

Example 3

Variant #21 Expression Vector Produces Plasma α-Gal a Activity In Vitro and In Vivo The levels and activity of secreted human α-Gal A were evaluated in various mouse, cynomolgus monkey and human primary cells and cell lines after transduction with variant #4 or variant #21 expression vectors. variant #4 or variant #21 expression vectors were produced in 1) HEK293 cells or 2) a Sf9 [0264], and [0 line.

HepG2 cells and iPSC-derived hepatocytes (iCell hepatocytes) were transduced using standard techniques and as described in U.S. Publication No. 20180117181. Briefly, cells were seeded at various densities per well and transduced with multiplicities of infection (MOI) ranging from 100,000 to 600,000 vg/cell of variant #21 expression construct or variant #4 expression construct. Supernatant samples were collected Day 3 to Day 7 and α-Gal A enzymatic activity was assessed by α-Gal A fluorometric activity assay and in cell pellets collected at the end of the study (Day 6 or 7).

The cDNA approach can include the use of an AAV delivered expression construct comprising an APOE enhancer linked to the hAAT promoter (Okuyama et al (1996) *Hum Gene Ther* 7(5):637-45), HBB-IGG intron (a chimeric intron composed of the 5'-donor site from the first intron of the human beta-globin gene and the branch and 3'-acceptor site from the intron of an immunoglobulin gene heavy chain variable region), a signal peptide, a coding sequence (wherein the coding sequence is optionally codon optimized) and a bovine growth hormone (e.g., bGH or SPA51) poly A signal sequence.

HepG2/C3A cells (also referred to as "HepG2" cells) (ATCC, CRL 10741) were maintained in Minimum Essential Medium (MEM) with Earle's Salts and L glutamine (Corning) with 10% Fetal Bovine Serum (FBS) (Life Technologies) and 1× Penicillin Streptomycin Glutamine (Life Technologies) and incubated at 37° C. and 5% CO2. Cells were passaged every 3 to 4 days.

For transduction, cells were rinsed and trypsinized with 0.25% Trypsin/2.21 mM EDTA (Corning) and re suspended in growth media. A small aliquot was mixed 1:1 with trypan blue solution 0.4% (w/v) in phosphate buffered saline (PBS;

Corning) and counted on the TC20 Automated Cell Counter (Bio Rad). The cells were re suspended at a density of 2e5 per mL in growth media and seeded into a 24 well plate (Corning) at 1e5 in 0.5 mL media per well. Recombinant AAV2/6 particles were mixed at the appropriate multiplicity of infection (MOI) with growth media and added to the cells. The MOI for the GLA cDNA constructs was either 3e4, 1e5, 3e5 or 1e6 vg/cell.

Following transduction, cells were left in culture for 6-10 days. Supernatant was collected on Days 3, 5, 7 and 10 (where applicable) and replaced with fresh media. After the final supernatant collection step, cells were trypsinized and resuspended as described above, then centrifuged to create a cell pellet, washed with PBS, and stored at −80 C.

α-GalA activity was assessed in a fluorometric assay using the synthetic substrate 4-methylumbelliferyl-α-D-galactopyranoside (4MU-α-Gal, Sigma).

Briefly, 10 microliters of HepG2 cell culture supernatant were mixed with 40 μL of 5 mM 4MU-α-Gal dissolved in phosphate buffer (0.1 M citrate/0.2 M phosphate buffer, pH 4.6, 1% Triton X-100). Reactions were incubated at 37° C. and terminated by addition of 100 μL of 0.5 M glycine buffer, pH 10.3. The release of 4 methylumbelliferone (4 MU) was determined by measurement of fluorescence (Ex365/Em450) using a SpectraMax Gemini XS fluorescent reader (Molecular Devices, Sunnyvale CA).

A standard curve was generated using serial 2 fold dilutions of 4 MU. The resulting data were fitted with a log log curve; concentration of 4 MU in test samples was calculated using this best fit curve. Enzymatic activity is expressed as nmol 4 MU released per hour of assay incubation time, per mL of cell culture supernatant (nmol/hr/mL).

Figures 7A, 7B, 8:
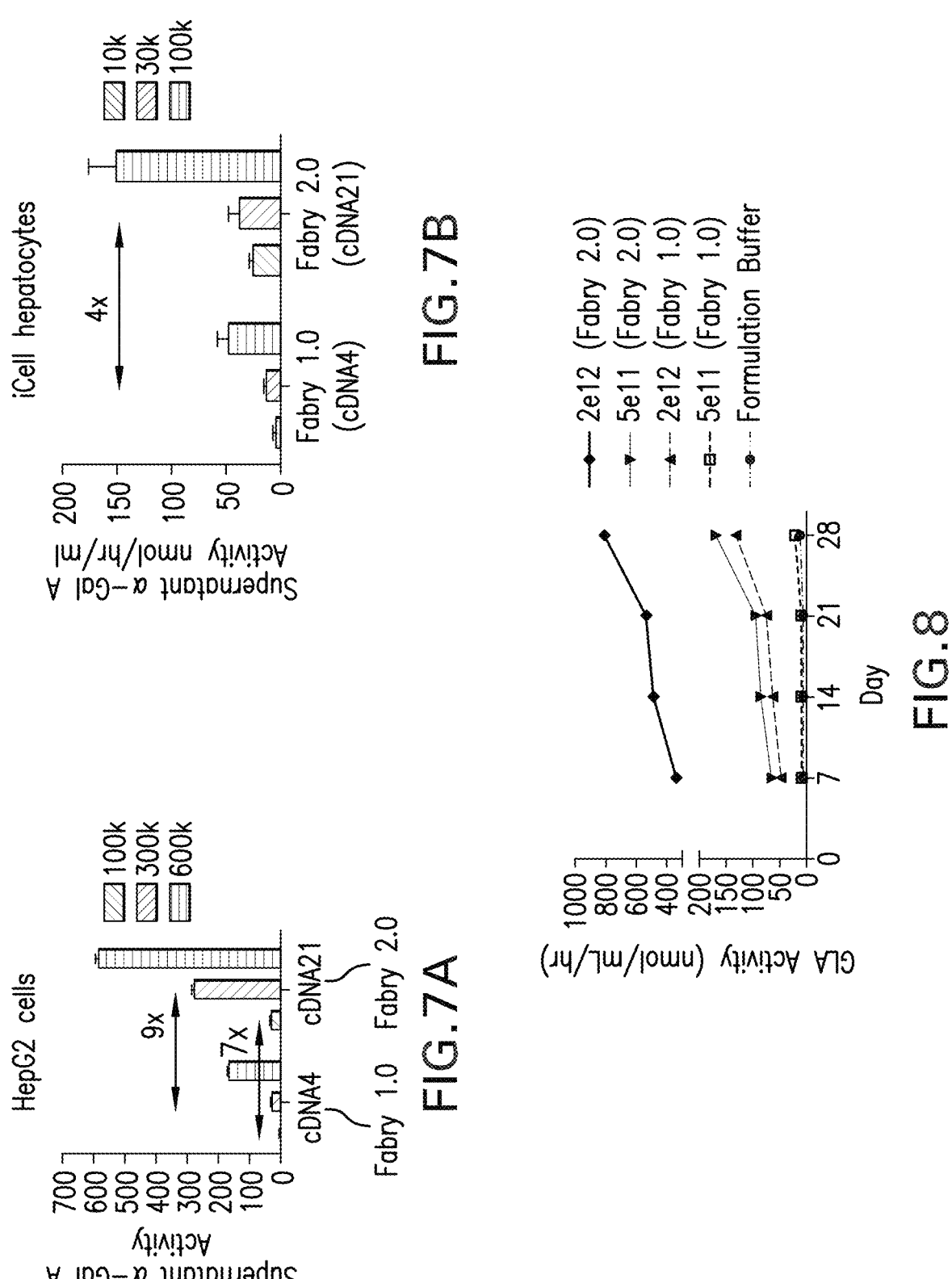
FIG. 7A is a graph showing in vitro α-Gal A activity in the supernatant of human HepG2 cells treated with either the cDNA variant #4 construct or the cDNA variant #21 construct (as shown in FIG. 1A and FIG. 1). Transgene activity was increased by at least about 9-fold in the cells treated with 300,000 AAV vg/cell using the expression construct comprising a WPRE sequence (construct variant #21 as depicted in FIG. 1B) as compared to activity when construct variant #4 was used as the expression construct. Transgene activity was increased by at least about 7-fold in the cells treated with 100,000 AAV vg/cell using the expression construct comprising a WPRE sequence (variant #21 as depicted in FIG. 1B) activity when construct variant #4 was used as the expression construct.
FIG. 7B is a graph showing in vitro α-Gal A activity in the supernatant of induced pluripotent hepatocyte cells ("iCell hepatocytes") treated with either the cDNA variant #4 construct or the cDNA variant #21 construct (as shown in FIG. 1A and FIG. 1i). Transgene activity was increased by at least about 4-fold in the cells treated with 30,000 AAV vg/cell using the expression construct comprising a WPRE sequence (variant #21 as depicted in FIG. 1B) as compared to activity when variant #4 was used as the expression construct. Transgene activity was increased by at least about 3-fold in the cells treated with 100,000 AAV vg/cell using the expression construct comprising a WPRE sequence (variant #21 as depicted in FIG. 1B) as compared to activity when variant #4 was used as the expression construct.
FIG. 8 is a graph showing increased GLA A activity with increase construct dose in the plasma of wild type mice treated with variant #21 constructs at a dose of 2.0E+12 vg/kg or 5E+11 vg/kg or variant #4 constructs at a dose of 2.0E+12 vg/kg or 5E+11 vg/kg or Formulation Buffer.

Turning to FIG. 7A and FIG. 7B, variant #21 expression construct has improved α-Gal A potency over AAV GLA variant #4 expression vector in vitro. In HepG2 cells, α-Gal A activity in supernatant was increased by between about 4-fold to about 9-fold, as presented in FIG. 7A. In iPSC-derived human hepatocytes, activity in supernatant was increased by between about 3-fold to about 5-fold, as presented in FIG. 7B.

Episomal AAV (serotype 2/6) vectors encoding human GLA cDNA (hGLA) driven by a liver-specific promoter lacking (variant #4) or including a mutated WPRE sequence (variant #21) were administered to the animals at varying doses. FIG. 8 shows an increase in GLA A activity with an increase in construct dose in the plasma of wild type mice treated with variant #21 constructs at a dose of 2.0E+12 vg/kg or 5E+11 vg/kg or variant #4 constructs at a dose of 2.0E+12 vg/kg or 5E+11 vg/kg or Formulation Buffer. The results indicate an improvement in plasma activity in wild type mice of between about 7-fold to about 9-fold over 28 days.

Expression construct variant #4 was compared to the cDNA construct including the WPRE sequence (variant #21) in a 1-month study using two different AAV doses (AAV carrying the cDNA donor) in wild type C57BL/6 mice. Table 1 above shows the complete sequence of the construct used. The construct comprising a cDNA with a WPRE sequence produced on average 7-fold higher levels of plasma α-GalA activity at study day 28 than mice administered the same dose of the initial (non-WPRE containing) cDNA.

A 4- to 9-fold increase in GLA activity in the supernatant of treated HepG2 cells was seen using the variant #21 (WPRE including construct) as compared to variant #4 (not including WPRE) and a 3- to 5-fold increase in GLA activity in the supernatant of hepatocytes derived from induced pluripotent cells (iCells) was seen using the variant #21

(WPRE including construct) as compared to variant #4 (not including WPRE). In addition, a 7- to 9-fold increase in plasma GLA activity was seen in mice treated with variant #21 (WRPE including construct) as compared to variant #4 (not including WRPE).

The high levels of α-GalA activity seen in these studies, along with the concomitant marked reduction in the accumulated Gb3/lyso-Gb3 in key tissues of the GLAKO mouse model, demonstrate that AAV-mediated targeting of hepatocytes results in therapeutic levels of human α-GalA in subjects, including via clinical scale manufacturing processes which allow for the rapid and efficient production of the therapeutic vectors.

Therapeutic levels of α-Gal A protein for treatment of Fabry are generated in vivo using a cDNA approach, including following clinical scale production of the expression vector.

The results presented in FIG. 9 and Table 3 below demonstrate that variant #21 expression construct produces plasma α-Gal A activity up to 1,500× of physiological normal (wt) in vivo. Variant #4 expression construct was administered by tail vein injection to C57BL/6 mice at 5.0E+12 and 5.0E+13 vg/kg. Variant #21 expression construct was administered by tail vein injection to C57BL/6 mice at 5.0E+12, 5.0E+13 and 5.0E+14 (not shown). Plasma samples were collected one week prior to dosing and on Days 8, 15, 22, and 29, and later evaluated for α-Gal A enzymatic activity by fluorometric assay. Data points represent mean response+/−SD per dose. The assay lower limit of quantitation (LLOQ) is 2.5 nmol/hr/mL.

TABLE 3

| Plasma α-Gal A activity at day 29 | | |
|---|---|---|
| Group (n = 4 or 8) | Plasma α-Gal A activity at day 29 (nmol/ml/hr) | Fold higher than normal |
| Variant #21 expression construct (5E+13 vg/kg) | 30,269 | 1,568× |
| Variant #4 expression construct (5E+13 vg/kg) | 4,297 | 223× |
| Untreated | 19.3 | 1× |

Figure 9:
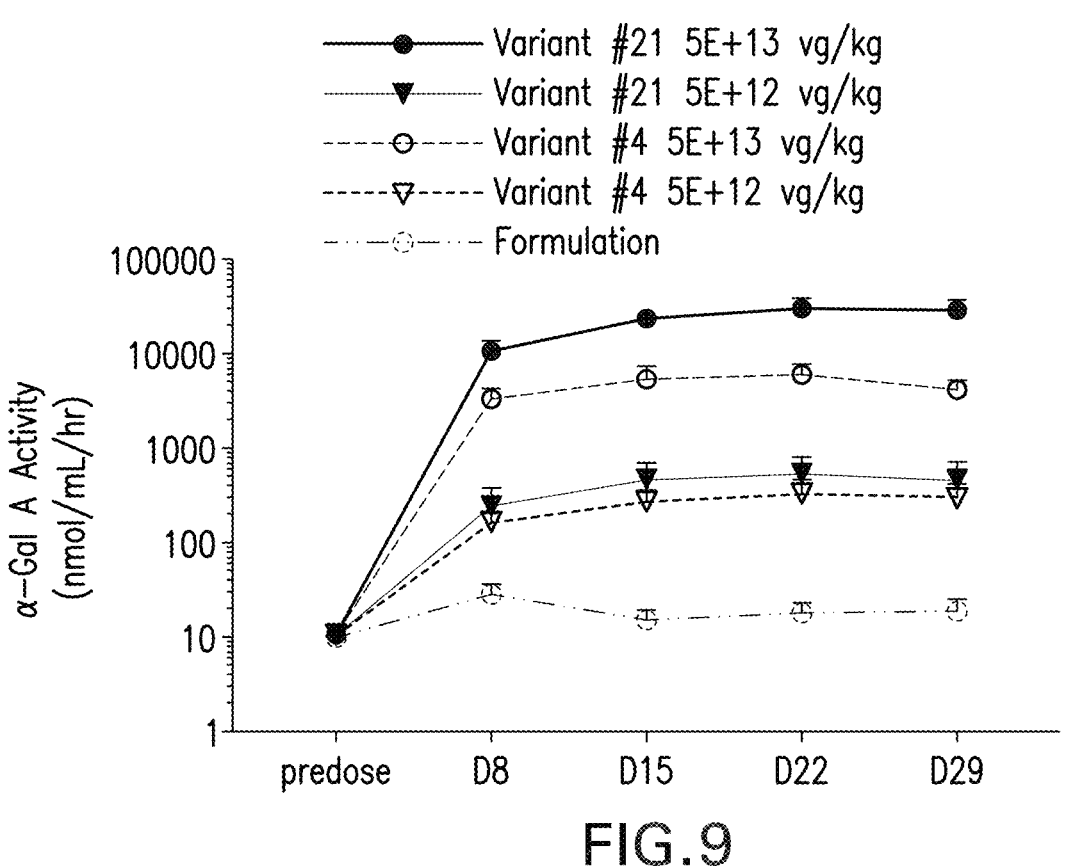
FIG. 9 is a graph depicting α-Gal A plasma activity in C57BL/6 mice over 29 days after being treated with either variant #21 constructs at a dose of 5.0E+13 vg/kg, variant #21 constructs at a dose of 5.0E+12 vg/kg, variant #4 constructs at a dose of 5.0E+13 vg/kg, variant #4 constructs at a dose of 5.0E+12 vg/kg, or Formulation Buffer. As shown, variant #21 constructs can produce over 1,500-fold the physiologically normal plasma α-Gal A activity levels in C57BL/6 mice.

FIG. 9 illustrates α-Gal A plasma activity in C57BL/6 mice over 29 days after being treated with either variant #21 constructs at a dose of 5.0E+13 vg/kg, variant #21 constructs at a dose of 5.0E+12 vg/kg, variant #4 constructs at a dose of 5.0E+13 vg/kg, variant #4 constructs at a dose of 5.0E+12 vg/kg, or Formulation Buffer.

Consistent with in vitro data, plasma and liver GLA levels were higher in animals administered variant #4 expression construct manufactured in HEK293 cell versus Sf9 cell system (up to 21-fold higher).

Example 4

Treatment with Variant #4 Expression Vector LED to High Levels of Hepatocyte Transduction in GLAKO Mice and Non-Human Primates To evaluate levels of expression construct copies in hepatocytes following IV administration of variant #4 expression construct, formalin-fixed paraffin-embedded (FFPE) liver samples from a subset of animals were evaluated by BASESCOPE™ in situ hybridization (ISH). Following ISH staining, quantitative image analysis was performed with HALO™ software. Non-coding sequences were targeted. A housekeeping gene probe, PPIB (Cyclophilin B) was used as a positive control marker for sample QC and to evaluate RNA quality in the tissue samples. The bacterial gene DapB was used as a negative control. Semi-quantitative scores (scale of 0-4) were obtained for all samples to assess sample quality and to determine QC pass/fail. PPIB (cyclophilin B; housekeeping gene control) scores were predominantly 3 for the samples indicating good quality RNA. DapB (bacterial gene control) scores were mostly 0, indicating no or negligible non-specific background. Specific DNA staining signal is identified as dark (red), punctate dots in the cell nucleus. Samples were counterstained with Gill's Hematoxylin, shown as light gray (blue color).

Figure 10:
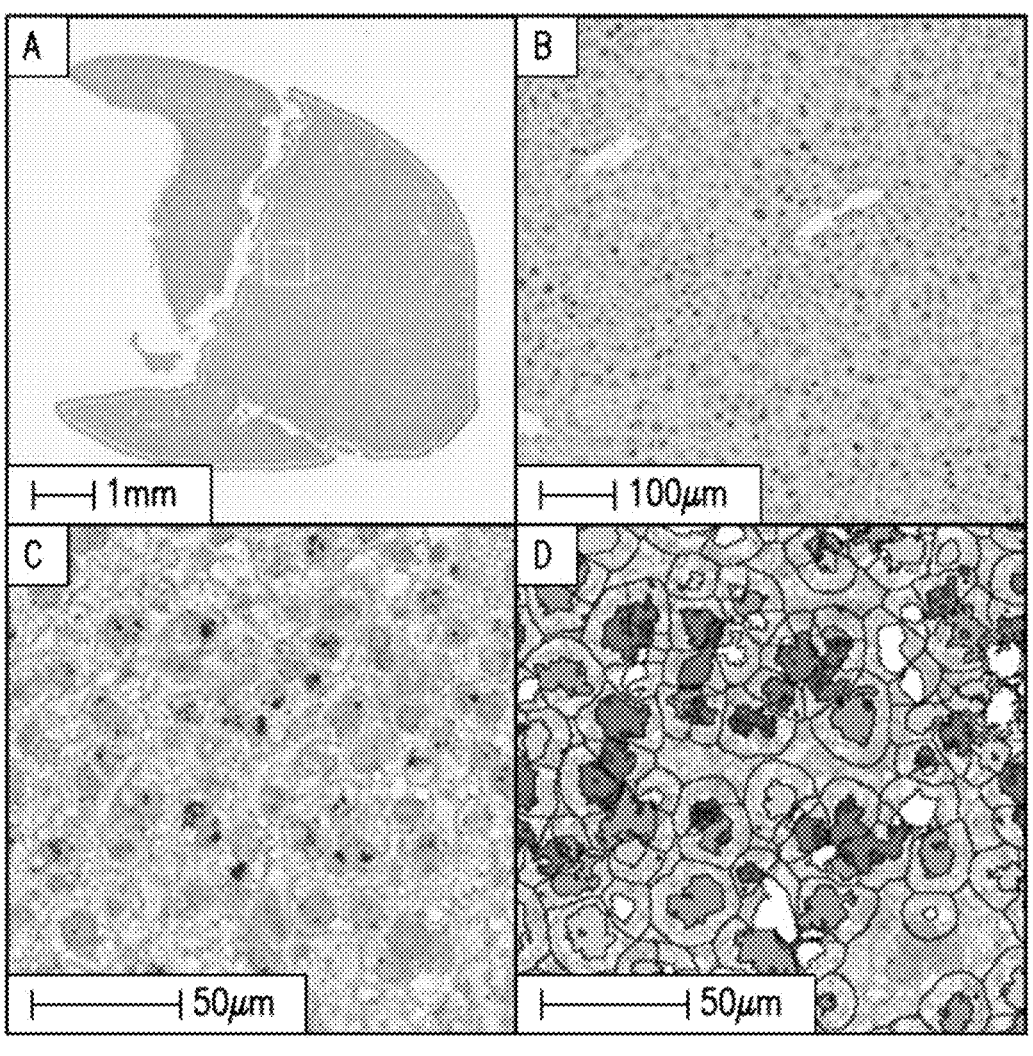
FIG. 10 are in situ DNA hybridization images stained for AAV vector genomes in a liver sample of a GLAKO mouse that was treated with variant #4 constructs at a dose of 5.0E+13 vg/kg. Non-coding sequences were targeted. In this sample, 57.5% of the liver cells stained positive for AAV vector genomes at 90 days after treatment.
Figure 11:
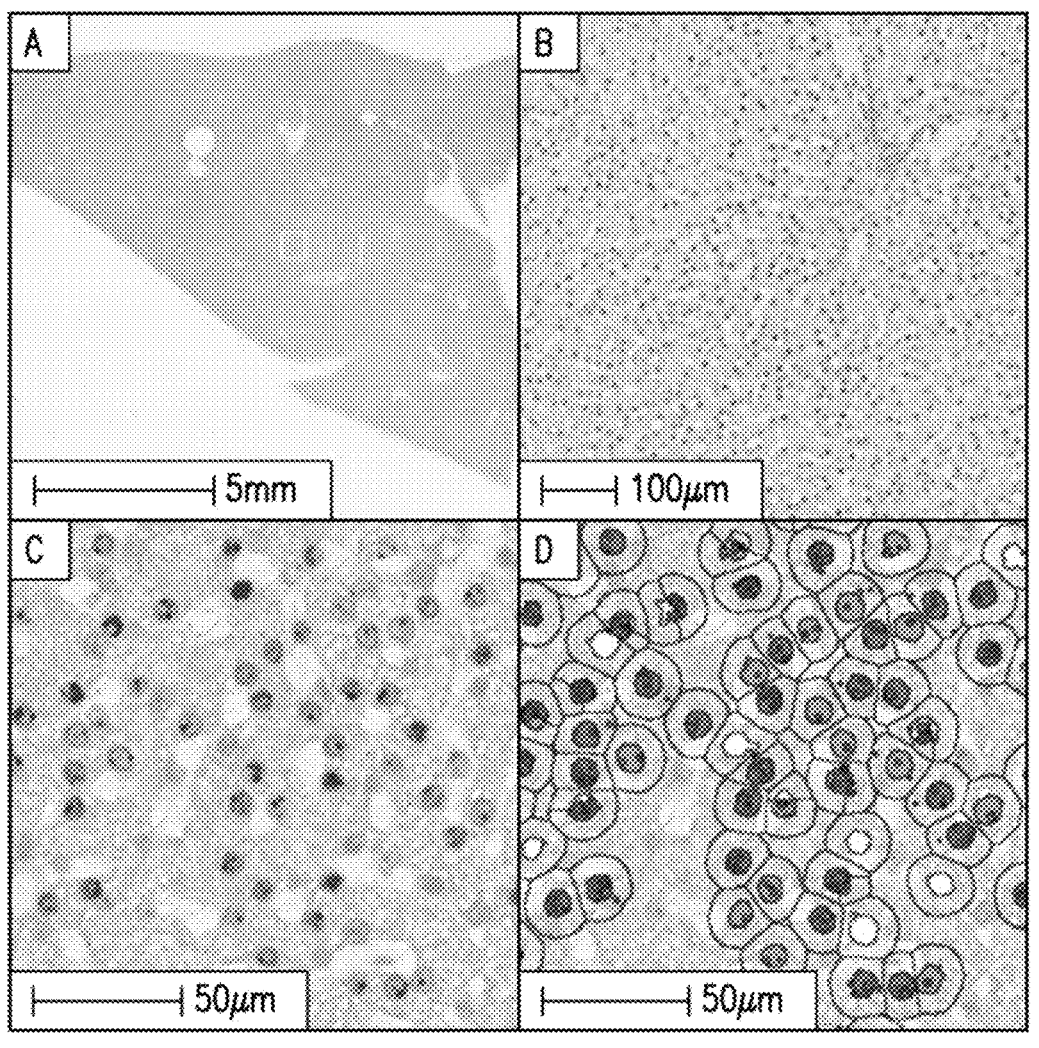
FIG. 11 are in situ DNA hybridization images stained for AAV vector genomes in a liver sample of a wild type non-human primate (NPH) that was treated with variant #4 constructs at a dose of 6.0E+13 vg/kg. Non-coding sequences were targeted. In this sample, 57.5% of the liver cells stained positive for AAV vector genomes at 60 days after treatment.

Representative ISH images of liver from of a GLAKO mouse administered 5.0+13 vg/kg variant #4 expression vector at various magnifications are presented in FIG. 10. Representative images of ISH staining in liver of a NHP administered 6.0+13 vg/kg variant #4 expression vector at various magnifications are presented in FIG. 11. Specific DNA staining signal is identified as dark gray, punctate dots in the cell nucleus. Samples were counterstained with Gill's Hematoxylin light gray. As shown, 57.5% of the mouse hepatocyte cells were positive for the expression vector, with 2.34 dots/cell, and an H-score of 126.82 in the representative sample in FIG. 10. Impressively, 72.9% of the NHP hepatocyte cells were positive for the expression construct, with 3.20 dots/cell, and an H-score of 175.39 in the representative sample in FIG. 11.

Overall, a dose-response relationship in mouse liver cells was observed for all parameters assessed including % positive cells, mean number of dots/cell and H-score. For determination of H-score, cells were divided into 5 bins based on the number of dots per cell, and then calculated by totaling the percentage of cells in each bin, according to a weighted formula.

Figures 12A, 12B, 12C, 12D:
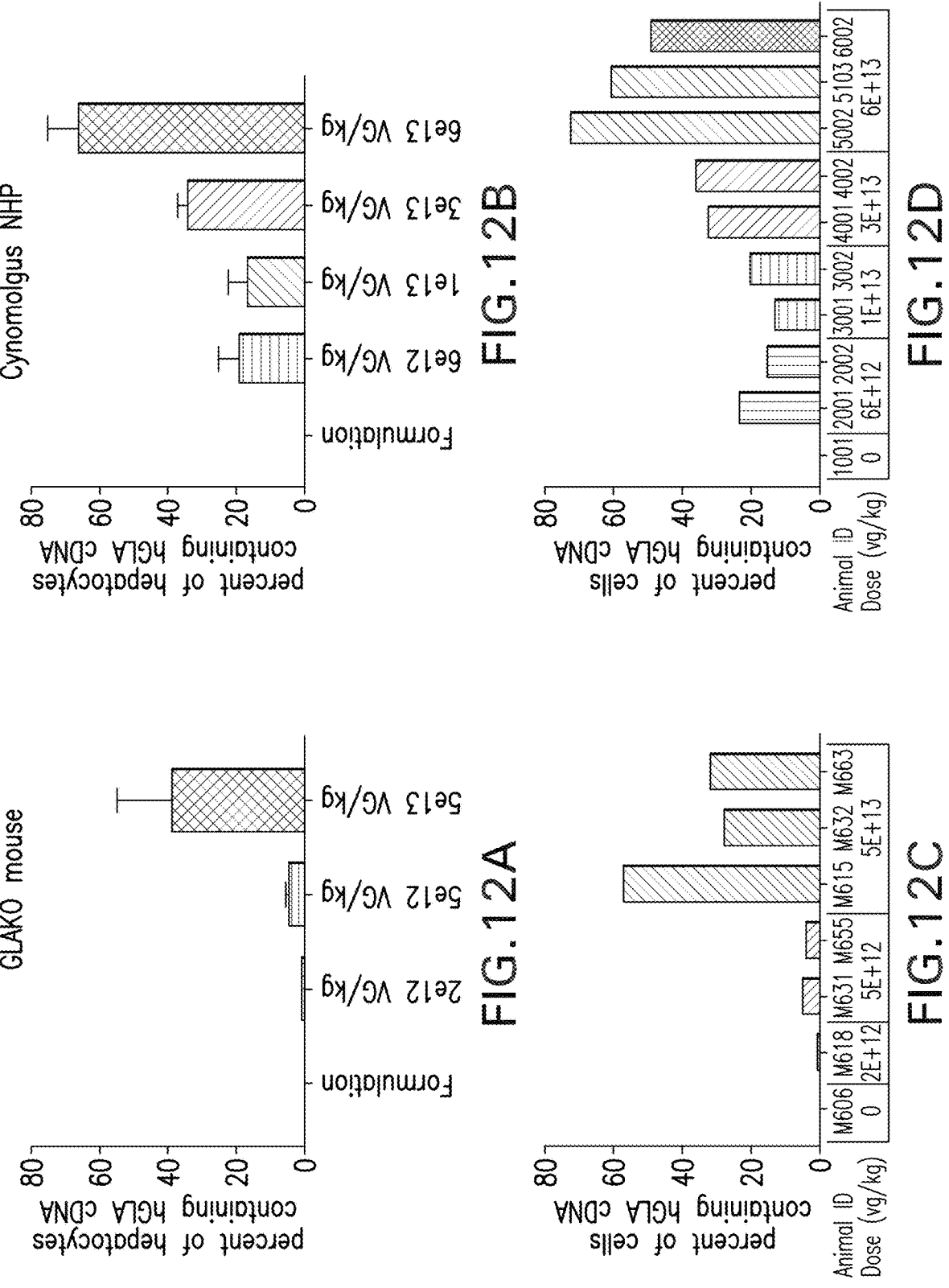
FIG. 12A is a graph showing the percent of hepatocytes containing hGLA cDNA in GLAKO mice treated with variant #4 constructs at doses of 2E+12 vg/kg, 5E+12 vg/kg, 5E+13 vg/kg, or Formulation buffer as a control.
FIG. 12B is a graph showing the percent of hepatocytes containing hGLA cDNA in cynomolgus NHPs treated with variant #4 constructs at doses of 6E+12 vg/kg, 1E+13 vg/kg, 3E+13 vg/kg, 6E+13 vg/kg or Formulation buffer as a control.
FIG. 12C is a graph showing the percent of liver cells containing hGLA cDNA in individual GLAKO mice treated with variant #4 constructs at doses of 2E+12 vg/kg, 5E+12 vg/kg, 5E+13 vg/kg, or Formulation buffer ("0") as a control.
FIG. 12D is a graph showing the percent of hepatocytes containing hGLA cDNA in individual cynomolgus NHPs treated with variant #4 constructs at doses of 6E+12 vg/kg, 1E+13 vg/kg, 3E+13 vg/kg, 6E+13 vg/kg or Formulation buffer ("0") as a control.
Figure 13A:
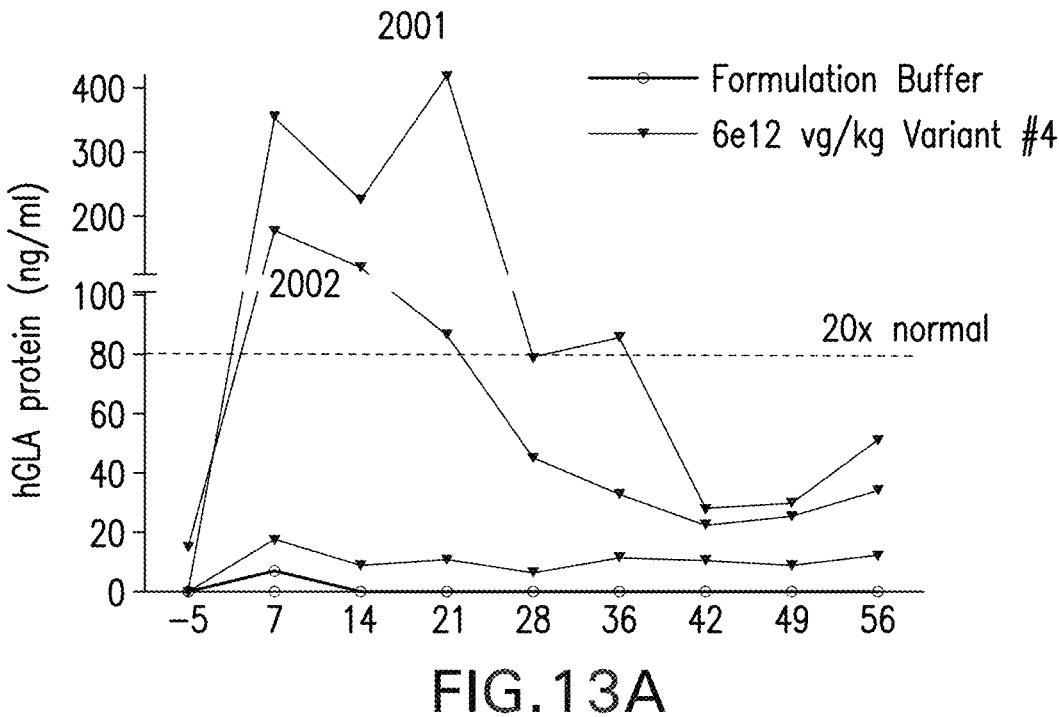
FIG. 13A and FIG. 13B are graphs showing NHP plasma hGLA activity vs protein concentration for individual animals treated with variant #4 constructs at a dose of 6.0E+12 vg/kg or Formulation Buffer.
Figure 13B:
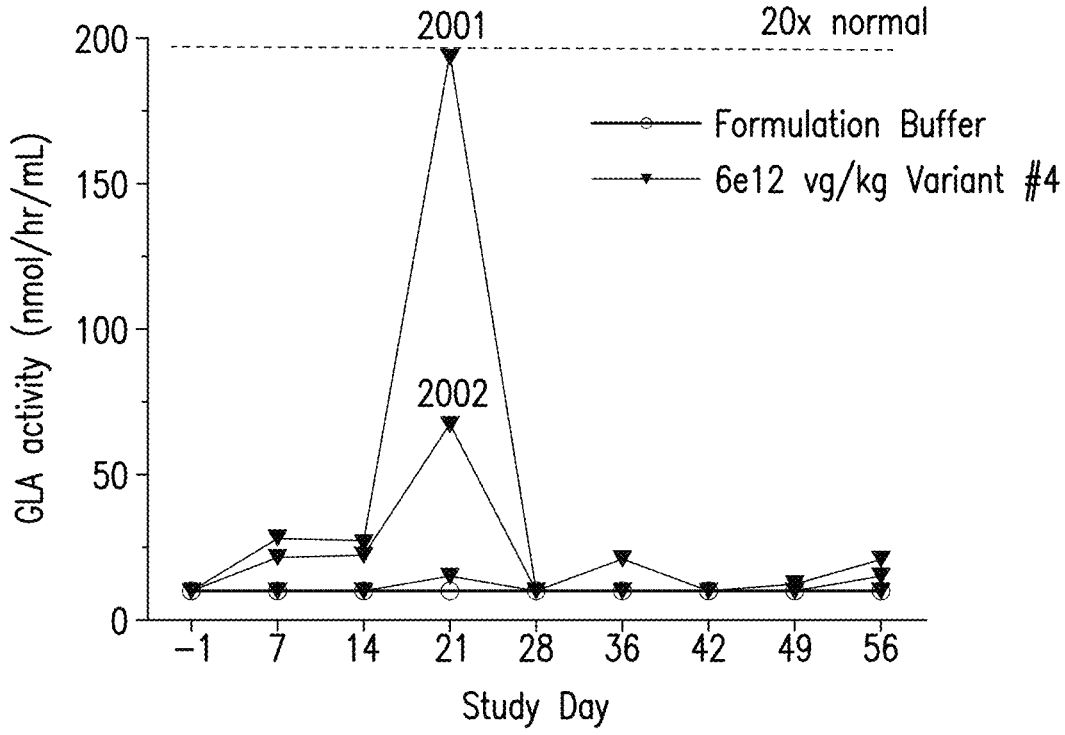
Figure 13C:
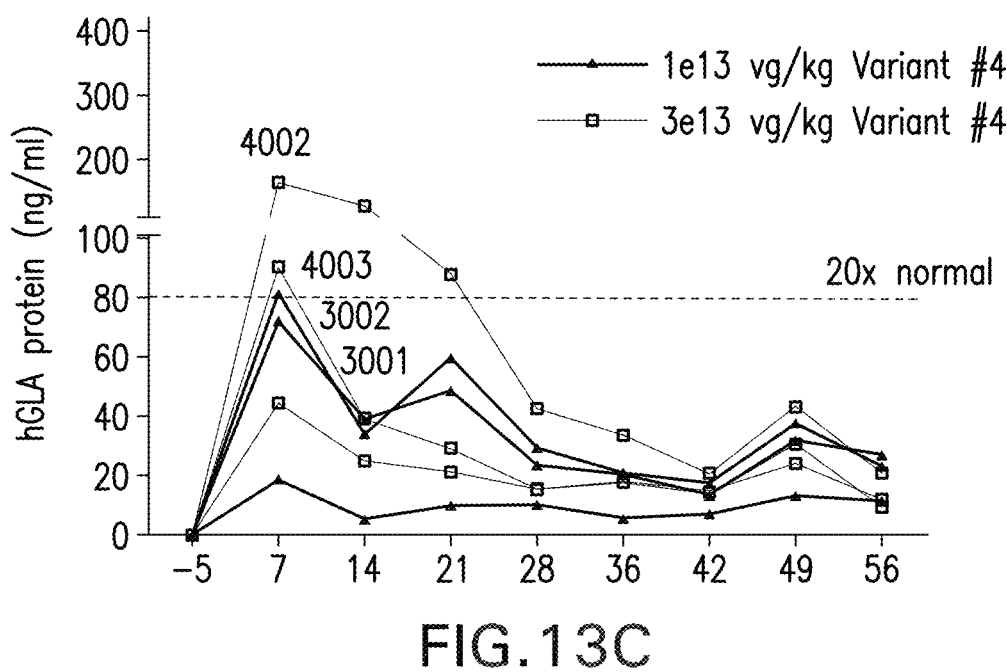
FIG. 13C and FIG. 13D are graphs showing NHP plasma hGLA activity vs protein concentration for individual animals treated with variant #4 constructs at doses of 1.0E+13 vg/kg or 3.0E+13 vg/kg.
Figure 13D:
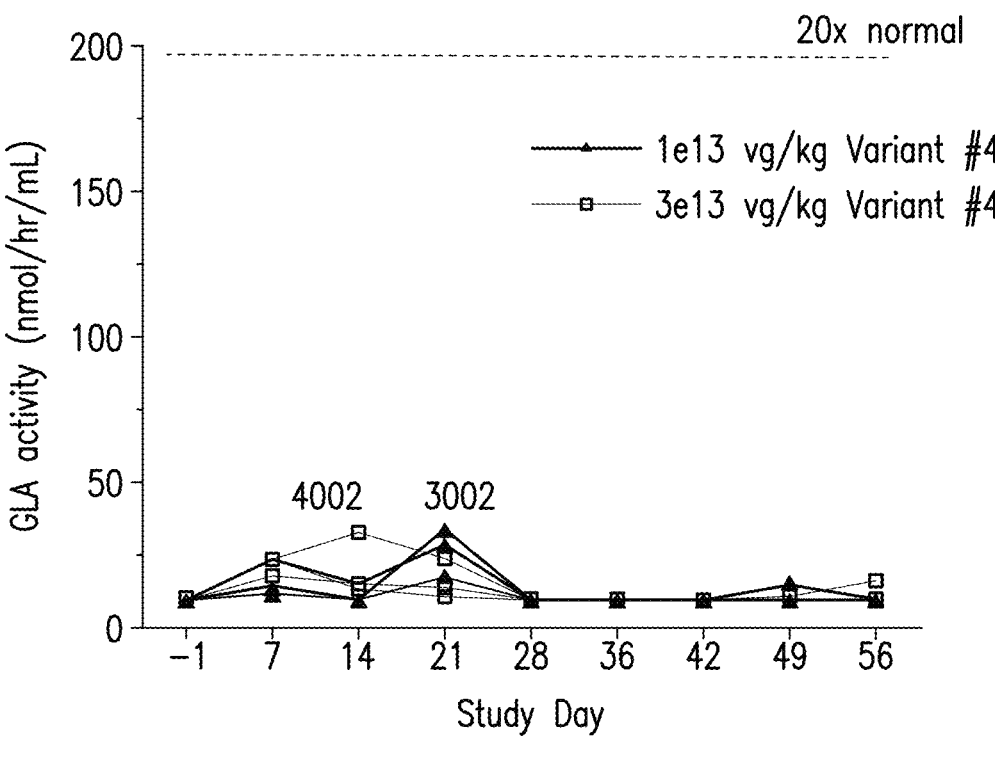
Figure 13E:
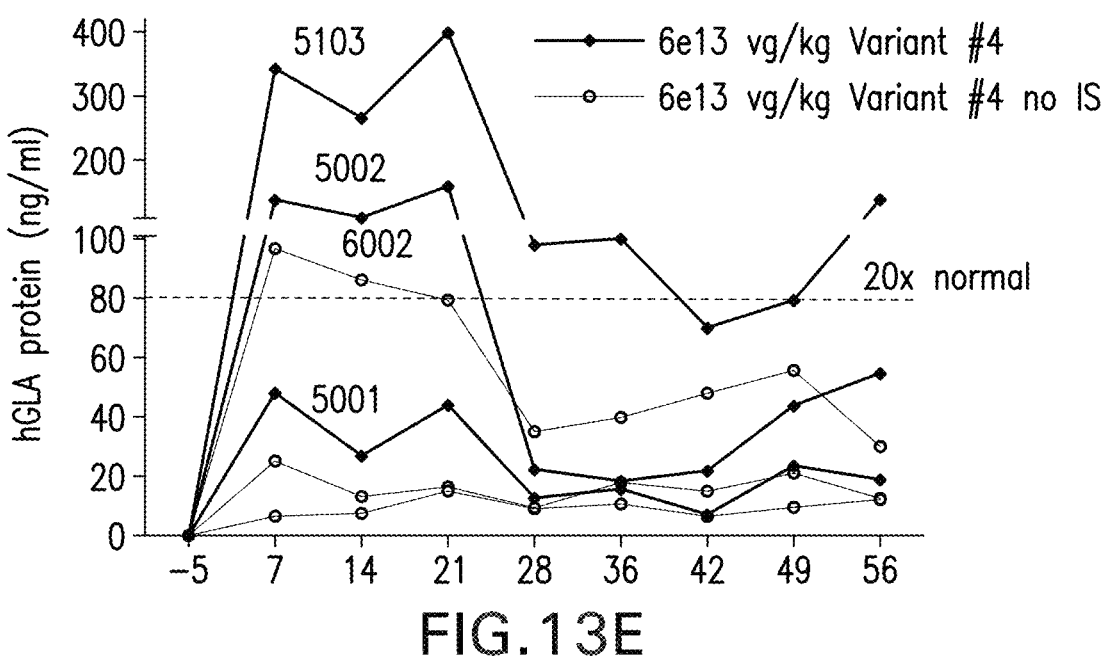
FIG. 13E and FIG. 13F are graphs showing NHP plasma hGLA activity vs protein concentration for individual animals treated with variant #4 constructs at doses of 6.0E+13 vg/kg or 6.0E+13 vg/kg without immunosuppressants.
Figure 13F:
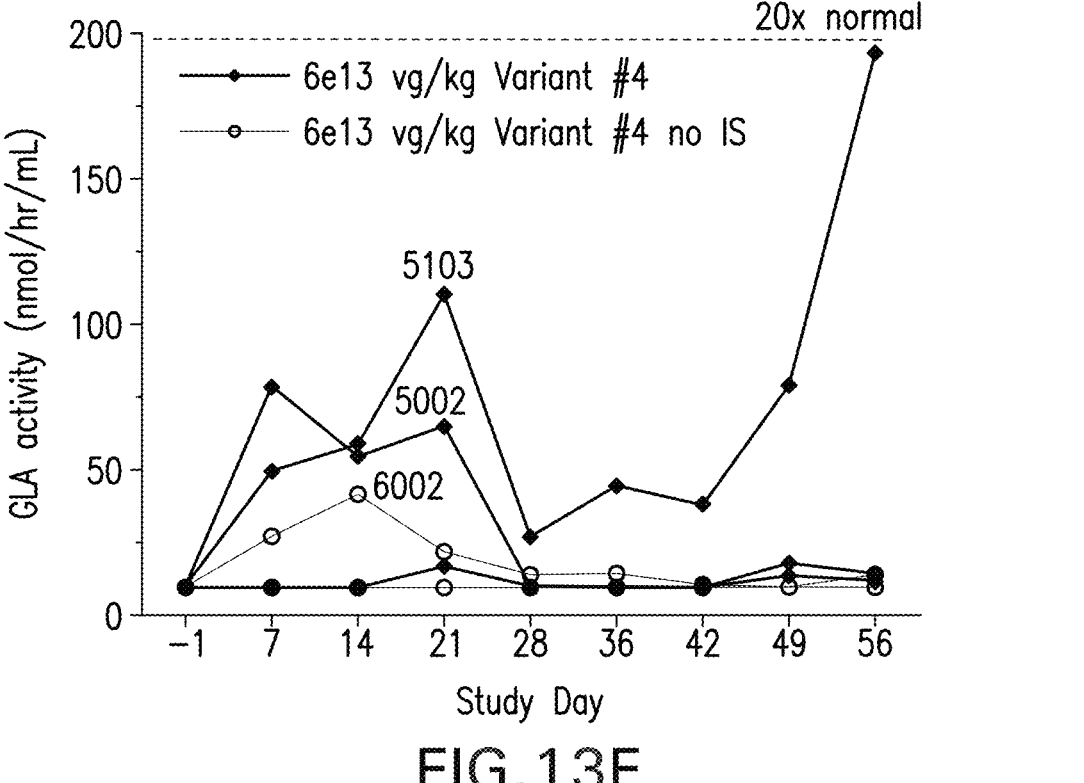

The percent of GLAKO mouse hepatocytes containing hGLA cDNA in GLAKO mice treated with variant #4 constructs at doses of 2E+12 vg/kg, 5E+12 vg/kg, 5E+13 vg/kg, or Formulation buffer as a control is shown in FIG. 12A. The percent of hepatocytes containing hGLA cDNA in individual subjects is presented in FIG. 12C. Similarly, FIG. 12B is a graph illustrating the percent of hepatocytes containing hGLA cDNA in cynomolgus NHPs treated with variant #4 constructs at doses of 6E+12 vg/kg, 1E+13 vg/kg, 3E+13 vg/kg, 6E+13 vg/kg or Formulation buffer as a control. FIG. 12D shows the percent of hepatocytes containing hGLA cDNA for individual NHP subjects.

In situ hybridization studies measuring levels of hGLA DNA construct in the liver showed a dose-response relationship in mouse and NHP hepatocytes and confirmed transfer of DNA to the nuclei. The high dose (5.0E+13 vg/kg) in the mouse yielded a range of 28% to 58% positive staining cells, and the high dose (6.0E+13 vg/kg; with immunosuppression) in the NHP study yielded a range of 61% to 73% positive staining cells. Another NHP (without immunosuppression) yielded 49% positive staining cells.

Example 5

α-Gal A Protein and Enzyme Activity in Cynomolgus NHPs after One-Time Intra Venous Administration of Variant #4 Expression Construct Variant #4 expression construct was evaluated in NHPs for pharmacology and toxicology. A single IV dose of variant #4 expression construct was administered at 0 (n=2), 6.0E+12, 1.0E+13, 3.0E+13 or 6.0E+13 vg/kg to male cynomolgus monkeys (n=3/group). To mitigate possible immune response to the expression vector and/or human α-Gal A, animals received rituximab (10 mg/kg; IV) prior to expression construct administration and methylprednisolone (10 mg/kg; intramuscular) daily throughout the study. An additional group received variant #4 expression construct at the highest dose (6.0E+13 vg/kg) but no immunosuppression administration. The variant #4 expression construct used was manufactured in a GMP clinical manufacturing process using baculovirus/Sf9 cell platform.

Blood was collected pre-dosing (5 timepoints), and on Days 7, 14, 21, 28, 35, 42, 49, and 56 and processed to plasma. These plasma samples were assessed for human α-Gal A protein levels and α-Gal A activity. At necropsy on Day 56, 4 segments of the liver (2 segments each of the left and right lateral lobes) and 2 segments of the spleen were collected for assessing α-Gal A activity. Results are shown in FIG. 13A through FIG. 13F.

Circulating α-Gal A protein levels and plasma α-Gal A activity were generally detected by Day 7, with protein levels and activity peaking between Days 7 and 21, and no clear dose response. Animals administered variant #4 expression construct without immunosuppression generally had lower levels of α-Gal A protein and activity than animals administered variant #4 expression construct with immunosuppression. This lack of strong dose response and clearance of α-Gal A activity and protein levels is consistent with an emerging immune response against human α-Gal A (a human protein administered to an animal) as confirmed by the presence of anti-human α-Gal A antibodies. Despite the reduced levels of human α-Gal A, some animals sustained high levels of human α-Gal A (activity and protein). In one high dose animal (6.0E+13 IS), levels of 193 nmol/hr/mL were measured on Day 56 while levels in vehicle treated animals were undetectable (<10 nmol/hr/mL). The transient nature of this response in some animals was likely related to an expected immune response to the human α-Gal A enzyme (human protein administered to an animal).

In addition, samples for vector shedding analysis were evaluated by a qPCR method in the NHP study. Low levels of hGLA vector were measured in the saliva, urine and feces of some variant #4-treated animals up to Day 4 (urine) or Day 14 (saliva, feces). At Day 60, no hGLA vector levels were detected in these biological fluids.

Example 6 hGLA and Corresponding mRNA Levels in NHP Liver

Figure 14:
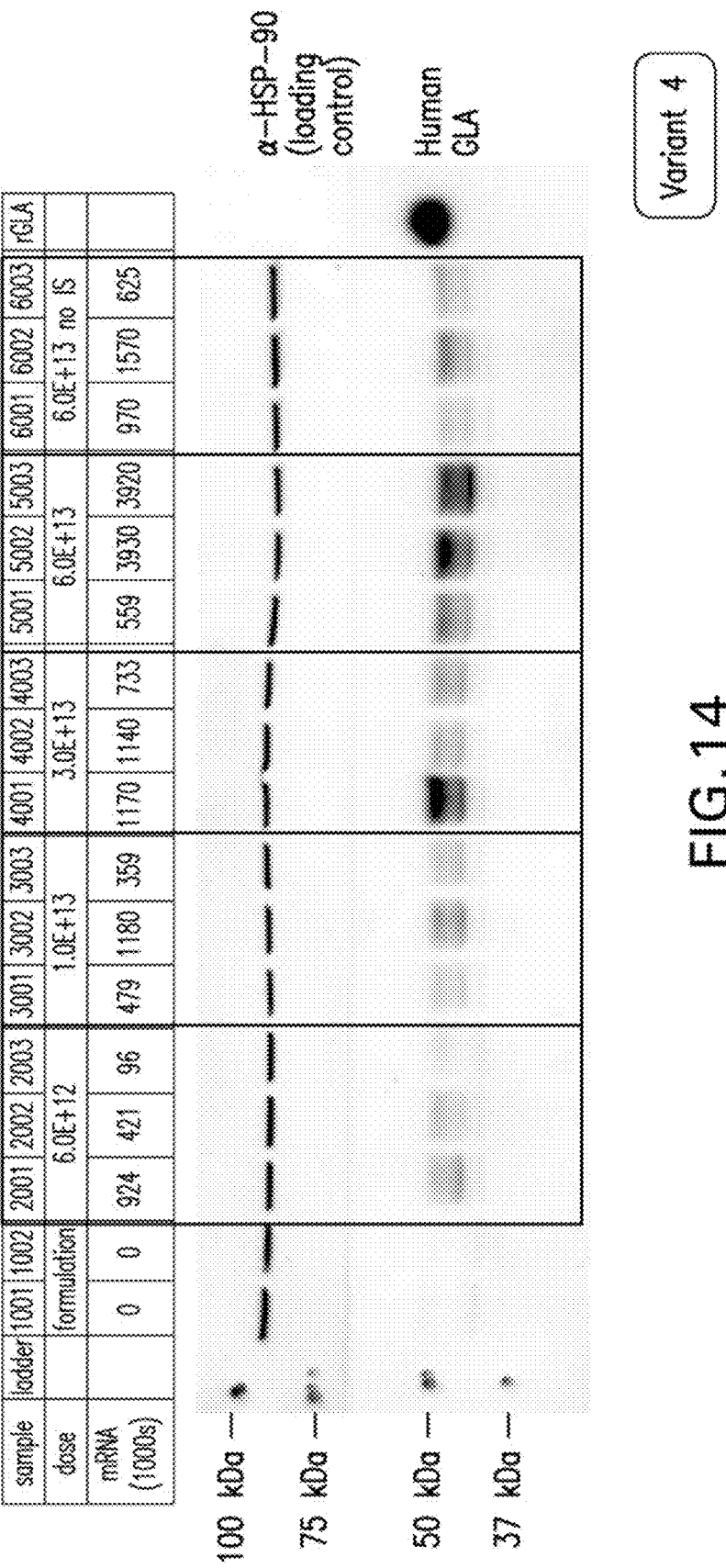
FIG. 14 is a Western blot analysis of hGLA and corresponding mRNA levels in NHP liver samples from individual animals at day 60 after treatment with variant #4 constructs at doses of 6.0E+12 vg/kg, 1.0E+13 vg/kg, 3.0E+13 vg/kg, 6.0E+13 vg/kg, 6.0E+13 vg/kg without immunosuppressants, or Formulation buffer. As shown, hGLA protein levels increase with construct dose and protein levels correlated with mRNA levels in most samples.

Western blot analysis of hGLA and corresponding mRNA levels in NHP liver samples from individual animals was performed at day 60 after treatment with variant #4 constructs at doses of 6.0E+12 vg/kg, 1.0E+13 vg/kg, 3.0E+13 vg/kg, 6.0E+13 vg/kg, 6.0E+13 vg/kg without immunosuppressants, or Formulation buffer. As shown in FIG. 14, hGLA protein levels increase with construct dose and protein levels correlated with mRNA levels in most samples.

Example 7

Assessment of the Safety, Tolerability and Pharmacodynamics of Variant #21 Expression Construct in Humans A study will be performed to assess the safety and tolerability of the variant #21 expression construct in humans. Additionally, the pharmacodynamics of α-Gal A and the presence of its substrates in plasma, urine and tissues over time will be measured. The impact of variant #21 expression constructs on ERT administration for subjects on ERT, renal function, immune response, and viral vector DNA shedding can also be evaluated over time.

Overall, variant #21 expression construct and variant #4 expression construct were well tolerated in a Fabry disease mouse model (GLAKO), wild-type (C56BL/6) mice and cynomolgus NHPs. In GLAKO mice, there were no adverse findings related to a single IV administration of variant #4 expression construct up to 5.0E+13 vg/kg, the highest dose level tested. In C57BL/6 mice, preliminary analysis showed that variant #21 expression construct was well tolerated up to the highest dose tested, 1.5E+14 vg/kg. In the NHP, variant #21 expression construct-related findings were limited to animals that did not receive an immunosuppression treatment (6.0E+13 vg/kg). These findings consisted of increases in lymphoid cellularity in lymphoid tissues and spleen and were likely consistent with an immune response related to hGLA and/or rAAV2/6 administration. In these studies, the no-observed-adverse-effect level (NOAEL) was 6.0E+13 vg/kg, with or without the immunosuppressive regimen, the highest dose level tested.

The study uses a recombinant (e.g., rAAV2/6) vector construct encoding the cDNA for human α-Gal A. The vector construct encodes a liver specific promoter, and rAAV2/6 exhibits liver tropism thus providing the potential for long-term and stable hepatic production of α-Gal A in Fabry disease subjects after a single dose administration. Various AAV serotypes may be used, including AAV2, 5, 6 and 8. The rAAV2/6 serotype was selected for use in this and the examples described above based on previous NHP data showing that AAV2/6 was primarily hepatotropic, with similar biodistribution to AAV2/8, and that AAV2/6 and AAV2/8 vectors yielded similar levels of circulating FIX transgene expression. Preliminary clinical safety data has been collected from 13 subjects dosed with investigational products in 3 of study trials and suggest that infusions with this AAV2/6 serotype are well tolerated (data not shown).

Studies in a Fabry disease mouse model administered IV with rAAV2/6 encoding hGLA cDNA show generation of therapeutic levels (over 300-fold wild type) of α-Gal A. The one-time treatment with the expression vector minimizes the incidence of infusion-related reactions. Production of therapeutic levels of α-Gal A in humans could enable reduction and potentially clearance of Fabry disease substrates Gb3 and lyso-Gb3 and may reduce the risk of antibody development to the enzyme produced because of constant production of the enzyme, rather than peak and trough seen with ERT. The variant #21 expression construct was designed to provide stable, long-term production of α-Gal A at therapeutic levels in subjects with Fabry disease. The constant production of α-Gal A in humans may enable reduction and clearance of Fabry disease substrates Gb3 and lyso-Gb3.

Study Evaluations

Evaluations may include incidents of treatment-emergent adverse events (TEAEs), routine hematology, chemistry, and liver function, vital signs, ECG and ECHO, serial alpha fetoprotein (AFP) testing and MRI of liver (or equivalent imaging) to monitor for the formation of any liver mass. Additionally, the change from baseline can be measured at specific time points over 1 year in the following: α-Gal A activity in plasma; Gb3 levels in plasma; Lyso-Gb3 levels in plasma; frequency of FABRAZYME® (or equivalent ERT) infusion; estimated glomerular filtration rate (eGFR) calculated by creatinine levels in blood; left ventricular mass measured by cardiac magnetic resonance imaging (MRI), total protein and albumin to creatinine ratios in urine; α-Gal A and Gb3 levels measured in tissue; substrate levels measured in tissues and urine; biomarkers of renal function in urine; neuropathic pain measured by the Brief Pain Inventory (BPI), frequency of pain medication use; gastrointestinal (GI) symptoms measured by the GI symptoms rating scale; Mainz Severity Score Index (MSSI); quality of life (QOL) patient-reported outcome measured by the SF-36 questionnaire; immune response to rAAV2/6 and $\alpha$-Gal A; and rAAV vector clearance can be measured by level of vector genome in blood, plasma, saliva, urine, stool, and semen.

Subject Inclusion and Exclusion Criteria

The study subjects may comprise male subjects ≥18 years of age with classical Fabry disease. Male subjects with classical Fabry disease should be recruited to ensure that any residual enzyme level does not interfere with the measurement of enzyme levels produced by the cDNA transgene.

More particularly, the subject inclusion criteria may comprise: (1) subjects with documented diagnosis of classical Fabry disease as defined by <5% $\alpha$-Gal A activity in either plasma or leukocytes and one or more of the following symptomatic characteristics of classical Fabry disease: i) cornea verticillata, ii) acroparesthesia, iii) anhidrosis, iv) angiokeratoma (if there is documented clustered periumbilicial angiokeratoma, this symptom alone is sufficient as it is a pathognomonic sign of classical Fabry disease); (2) subject who is on ERT (14 days [±1 day] regimen); or subject on ERT whose -Gal A activity is >5%; or is ERT-naive; or is ERT-pseudo-naive and has not received ERT treatment in the past 6 months prior to consent; (3) for subjects receiving ERT, ERT should have been administered at a stable dose (defined as not having missed more than 3 doses of ERT during the 6 months prior to consent) and regimen (14 days±1 day for at least 3 months prior to enrollment); (4) subject with a mutation that is indicative of classical Fabry (i.e. listed in a database, such as www.dbfgp.org); (5) subject whose $\alpha$-Gal A activity at trough is below the lower limit of the normal range of the assay; (6) male subjects ≥about 18 years of age; (7) sexually mature subjects must agree to use a condom and refrain from sperm donation from the time of expression construct administration until a minimum of 3 consecutive semen samples are negative for AAV after administration of study treatment and a minimum of 90 days after study treatment administration; and (8) signed, written informed consent of the subject.

For subjects who do not have a documented diagnostic $\alpha$-Gal A activity level, a blood sample should be taken to measure $\alpha$-Gal A activity levels (in plasma and/or leukocytes). For those subjects who are on ERT, this blood draw must be taken at least 13 days after their last ERT infusion (trough). i. If the subject's level of $\alpha$-Gal A activity is >5% and the subject is on ERT, this level of enzyme activity may be due to residual $\alpha$-Gal A activity from the last ERT infusion. In this case, the diagnosis of classical Fabry disease may be confirmed if the following three criteria are fulfilled:

a. two or more of the following documented symptomatic characteristics of classical Fabry: cornea verticillata, acroparesthesia, anhidrosis, angiokeratoma. If there is documented clustered periumbilicial angiokeratoma, this symptom alone is sufficient as it is a pathognomonic sign of classical Fabry disease;

b. a mutation that is indicative of classical Fabry (i.e. listed in a database, such as www.dbfgp.org); and c. the $\alpha$-Gal A activity at trough is below the lower limit of the normal range of the assay.

Fabry disease gene sequencing may be performed at screening to confirm that subjects have a mutation in the GLA gene. The assay may be performed on blood or saliva samples. If available, gene sequencing results obtained prior to the study may be used.

Testing for HIV, HAV, HBV, HCV, and TB can be conducted at screening. Subjects with a diagnosis of HIV or evidence of active HAV, HBV, HCV, or TB infection may not be eligible to participate in this study.

The level of neutralizing antibodies to AAV6 can be measured at screening to assess the subject's pre-existing immune response to AAV6. Subjects with elevated pre-existing neutralizing antibodies to AAV6 may not be eligible to participate in this study. If dosing is not completed within 3 months of screening, the serum neutralization assay to AAV6 should be repeated.

If available, diagnostic $\alpha$-Gal A activity level results in plasma or leukocytes obtained prior to the study may be used. For subjects who do not have a documented diagnostic $\alpha$-Gal A activity level, a blood sample should be taken to measure $\alpha$-Gal A activity levels (in plasma and/or leukocytes). For those subjects who are on ERT, this blood draw should be taken at least 13 days after their last ERT infusion.

Chest X-rays (also known as PA radiograph of the chest) can be obtained to evaluate the general health and study eligibility of the subject. Unless medically indicated, a chest X-Ray taken within 6 months of enrollment in the study may be used to determine subject eligibility. Physical examinations should be conducted on each subject and should include at minimum: general appearance, head, eyes, ears, nose, and throat (HEENT); as well as cardiovascular, dermatologic, respiratory, GI, musculoskeletal, and neurologic systems.

The subject exclusion criteria may comprise subjects who: (1) are known to be unresponsive to ERT in the opinion of the Site Investigator and Medical Monitor (e.g., no documented substrate level decrease on ERT); (2) are undergoing current treatment with migalastat (Galafold™) or prior treatment within 3 months of informed consent, (3) have a positive neutralizing antibody response to AAV (e.g., AAV6), (4) have intercurrent illness expected to impair evaluation of safety or efficacy during the observation period of the study in the opinion of the Site Investigator or Medical Monitor; (5) have eGFR≤60 ml/min/1.73m2; (6) have a New York Heart Association Class III or higher; (7) have an active infection with hepatitis A virus (HAV), hepatitis B virus (HBV), hepatitis C virus (HCV) (negative HCV-DNA), or human immunodeficiency virus (HIV) as measured by quantitative polymerase chain reaction (qPCR) or active infection with tuberculosis (TB); (8) have a history of liver disease such as secondary steatosis, non-alcoholic steatohepatitis (NASH) and cirrhosis, cholangitis, biliary disease within 6 months of informed consent; except for Gilbert's syndrome; abnormal circulating AFP; (9) for subjects receiving ERT, have recent or continued hypersensitivity response to ERT treatment within 6 months prior to consent, as manifested by significant infusion reaction to ERT in the opinion of the Site Investigator and Medical Monitor; (10); markers of hepatic inflammation or overt or occult causes of liver dysfunction as confirmed by one or more of the following: (i) albumin ≤3.5 g/dL; (ii) total bilirubin>upper limit of normal (ULN) and direct bilirubin ≥0.5 mg/dL; (iii) alkaline phosphatase (ALP)>2.0×ULN; (iv) alanine aminotransferase (ALT)>1.5×ULN; (11) have a current or history of systemic (IV or oral) immunomodulatory agent or steroid use in the past 6 months (topical treatment is allowed, e.g. asthma or eczema) (occasional use of systemic steroid may be allowed after discussion with the Medical Monitor); (12) have a contraindication to use of corticosteroids for immunosuppression; (13) have a history of malignancy except for non-melanoma skin cancer; (14) have a history of alcohol or substance abuse; (15) have participated in prior investigational interventional drug or medical device study within the last 3 months prior to consent (with the exception of implantable loop recorders as in the RaILRoAD trial); (16) have received prior treatment with a gene therapy product; (17) Known hypersensitivity to components of ST-920 formulation; (18) Any other reason that, in the opinion of the Site Investigator or Medical Monitor, would render the subject unsuitable for participation in the study Concomitant Medications All medications can be permitted, except for those that are potentially hepatotoxic. Hepatotoxic agents such as diclofenac, amiodarone, chlorpromazine, fluconazole, isoniazid, rifampin, valproic acid, high doses of acetaminophen (4-8 gm/day), etc. as well as hepatotoxic herbal supplements such as senecio/crotalaria, germander in teas, chaparral, Jin bu huan, Ma-huang (Chinese herbs), etc. should not be taken during the study period. For subjects receiving ERT, ERT should have been administered at a stable dose (defined as not having missed more than 3 doses of ERT during the past 6 months prior to consent) and regimen (14 days±1 day for at least 3 months prior to enrollment. Subjects should continue to receive ERT at a stable dose and regimen (14 days±1 day) during the study as per standard of care unless they undergo ERT withdrawal.

Dose Cohorts

The starting dose will be 5.0E+12 vg/kg, and any dose escalation to the next dose level will be upon review of data from the previous cohort and/or other clinical trials that use in vivo rAAV2/6-based therapy, and based on the recommendation of the Safety Monitoring Committee (SMC), which can comprise external subject matter experts, the study medical monitors, and site investigators as appropriate. As used herein, the SMC members will have appropriate medical and scientific expertise and will provide safety oversight of the study. In addition, depending on the observed enzyme activity levels and safety profile of the subjects dosed, the SMC may recommend a dose escalation to an intermediate dose level of 3.0E+13 vg/kg, a 3-fold increase from the dose in Cohort 2 instead of a 5-fold increase to the 5.0E+13 vg/kg dose in Cohort 3. A dose of about 1.0E+14 vg/kg may also be considered. The three dose cohorts are shown in Table 4.

TABLE 4

Dose cohorts

| Cohort # | Total rAAV* Dose (vector genomes [ve]/kg) |
|---|---|
| 1 | 5.0E+12 |
| 2 | 1.0E+13 |
| 3 | 5.0E+13 |

*rAAV = recombinant adeno-associated virus

Subjects ≥18 years of age who satisfy all inclusion/exclusion criteria will be enrolled. At least two subjects will be assigned into each of the 3 dose cohorts with a potential expansion of any cohort with an additional 4 adult subjects, for a total of up to 18 subjects, after SMC review. The expression vector can be administered via intravenous infusion. Within each cohort, treatment will be staggered so that each subsequent subject cannot be infused until at least about 2 weeks after the preceding subject has been dosed. Dose escalation to the next dose level may not occur until at least about 4 weeks after the last subject in the preceding cohort has been dosed, and safety data from the entire prior cohort has been reviewed by the SMC.

Subjects who received ERT prior to study enrollment should continue to receive ERT during the study and remain on their current dose and regimen (14 days±1 day) per standard of care unless they undergo ERT withdrawal. For subjects on ERT, baseline testing of enzyme and substrate levels will be coordinated such that samples can be taken on 2 separate occasions in the morning at trough, defined as 14 days (+/−1 day) after the previous ERT infusion. An additional time point will have been taken previously during the screening period, therefore, having 3 time points to assess the residual levels of α-Gal A at trough prior to the gene therapy administration. These 3 samples should be taken at trough, and preferably at the same time during the day (e.g. in the morning) to minimize non-specific factors potentially impacting on the levels of the enzymes.

To minimize the potential immune response to the rAAV capsid protein, to avoid losing transgene expression in the case of liver damage and to preserve hepatic function, prednisone or equivalent corticosteroid can be administered prophylactically starting about 2 days prior to expression vector infusion and can be tapered over a period of up to about 20 weeks.

The expression vector can be injected using a syringe pump or IV infusion pump (see Study Pharmacy Manual). Total volumes will be dependent on subject's cohort assignment and body weight (kg) at baseline. The expression vector can be administered through an IV catheter at a controlled speed while monitoring the subject's vital signs (temperature, heart rate, respiratory rate, and blood pressure). while the subject is in the hospital or acute care facility, where the subject may remain for observation for at least 24 hours after completion of the expression vector infusion. The subject can be discharged when all vital signs are stable and any adverse events (AEs) have resolved or the subject is considered stabilized as per the Investigator judgment.

Following infusion with the expression vector, study visits may be conducted on Day 8; Weeks 2, 4, 6, 8, 12, 16, 20, 24, 28, 32, 36, 40, 44, 48, and 52. Week 28, 32, 40, 44, and 48 study visits have assessments that do not require evaluation at the clinical site, and therefore may be conducted remotely. Assessments for AEs and concomitant medications may be conducted remotely over the phone.

Liver tests (AST, ALT, GGT, total and direct bilirubin, ALP, LDH, albumin, and total protein levels) can be conducted to monitor for AAV-mediated immunogenicity twice weekly during about the first 20 weeks after expression vector infusion while the subject is on prednisone or equivalent corticosteroid and may be conducted remotely. Blood samples for liver tests can be drawn 2-4 days apart when possible, except for the first week when they can be drawn on the Day 2 and Day 8 visits. Liver tests can subsequently be conducted weekly for four weeks following discontinuation of immunosuppression (Weeks 21-24), and then monthly thereafter to coincide with study visits (Weeks 28-52).

If, despite pre-treatment with prednisone or equivalent corticosteroid, there is evidence of ALT elevation, the dose of prednisone or equivalent corticosteroid will be continued (prednisone 1 mg/kg [max 60 mg] or equivalent; oral or intravenous and/or increased on a case-by-case basis, and liver enzymes may be assessed twice a week until normalization of liver enzymes, and then per protocol thereafter.

For the first 2 subject in each cohort, treatment can be staggered so that each subsequent subject will not be infused until the preceding subject has been observed for at least 2 weeks. Dose escalation to the next dose level may not occur until at least 4 weeks after 2 subjects in the preceding cohort has been dosed and the safety data from the 2 subjects in the prior cohort has been reviewed by the SMC.

Dosing and dose escalation may be paused if any of the stopping rules are met.

Treatment with the expression vector may abrogate the need for ERT, by using a rAAV vector encoding cDNA for human α-Gal A, resulting in long-term, liver-specific expression of α-Gal A in Fabry disease subjects. Subjects who undergo ERT withdrawal will be closely monitored for any AEs, vital signs, any changes in safety laboratory evaluations and levels of α-Gal A and substrates compared to baseline. The ERT withdrawal should be considered after a period of four weeks, in order to allow enough time for transduction of the target liver cells. The subjects who undergo ERT withdrawal will be closely monitored for any clinical symptoms including fatigue, and neuropathic pain, any AEs, vital signs, any changes in safety laboratory evaluations, including liver function tests and levels of α-Gal A and substrates (Gb3 and Lyso-Gb3) compared to baseline. ERT withdrawal may be at the discretion of the Site Investigator after consultation with the Sponsor, and should be considered for subjects who are willing and meet the following criteria:

(1) are ≥4 weeks post-administration of ST-920;
(2) are medically stable and can tolerate temporary discontinuation of ERT in the judgment of the Site Investigator;
(3) agree to increased safety monitoring and additional lab testing until ERT Withdrawal Follow-Up visit;
(4) ERT does not need to be restarted after the ERT Withdrawal Follow-Up visit. However, ERT may be re-initiated at any time based on clinical circumstances or at the judgment of the Site Investigator.

ERT withdrawal may be repeated if previously unsuccessful, provided this is done at least 12 weeks after the previous attempt if the subject is willing, and may be at the discretion of the Site Investigator and after consultation with the Sponsor.

The duration of study participation may be up to 76 weeks for each subject divided into up to 8 weeks for screening, up to 12 weeks for baseline, and 52 weeks follow-up after dosing. Accrual is planned for 9 to 12 months. Subjects should be encouraged to participate in an additional separate long-term follow-up study for up to 4 years.

The study enrollment should be paused if any of the following criteria are met and the SMC may convene to make recommendations as to the proper course of action: (1) any one Grade 3 or higher adverse event with at least a reasonable possibility of a causal relationship to the expression vector formulation; (2) serious adverse event (SAE) with at least a reasonable possibility of a causal relationship to the expression vector formulation; (3) death of a human subject; (4) development of a malignancy.

Treatment-emergent AEs can be summarized overall and by dose cohort. For each subject, the maximum reported severity of each AE can be used in the summaries by severity grade. In addition, all SAEs and AEs related to study treatment can be summarized. For other safety evaluations, data can be summarized for each time point. Change from baseline values may be calculated for continuous parameters and summarized by time point. Shift-tables may also be constructed for selected parameters.

α-Gal A activity in plasma should be measured to assess whether α-Gal A is being produced and is active. α-Gal A level measurements may be conducted on plasma, serum, whole blood, dried blood spot, leukocytes, or other blood components. For those subjects on ERT, samples should be obtained at trough, defined as 14 days (±1 day) after the previous ERT administration. Additional samples may also be obtained throughout the study to further our understanding of the pharmacokinetics of the enzyme and ensure that samples obtained prior to ERT are at trough.

Gb3 is a type of glycosphingolipid that accumulate within blood vessels, tissues and organs in Fabry disease due to a deficiency in α-Gal A. Gb3 levels in plasma, urine, and other tissues may be measured throughout this study to evaluate the impact of treatment administration and α-Gal A levels. For those subjects on ERT, samples should be obtained at trough, defined as 14 days (±1 day) after the previous ERT administration.

Lyso-Gb3 is a soluble form of the substrate Gb3. Lyso-Gb3 levels in plasma, urine, and other tissues may be measured throughout this study to evaluate the impact of treatment administration and α-Gal A levels. For those subjects on ERT, samples should be obtained at trough, defined as 14 days (±1 day) after the previous ERT administration.

At each sampling time point, the actual value and the change from baseline for α-Gal A and Gb3 and lyso-Gb3 levels can be summarized using descriptive statistics and plotted over time by dose cohort. For subjects who undergo ERT withdrawal, changes from pre- to post-ERT withdrawal in the frequency and dose of ERT infusions can be evaluated and summarized using annualized total dose and number of infusions. Duration of ERT withdrawal may also be analyzed. AAV clearance measured by vector genomes in the different samples (plasma, saliva, urine, stool, and semen) can be plotted over time by dose cohort.

As shown in FIG. 1A, the rAAV vector comprises the variant #21 hGLA expression cassette (3321 bp) that includes liver-specific regulatory elements that drive expression of a hGLA transgene. The hGLA transgene is under the control of an enhancer and hepatic control region from the human apolipoprotein E (ApoE) gene and the human α-1-antitrypsin (hAAT) promoter. The ApoE enhancer and hAAT promoter are specifically and highly active in the liver, the intended target tissue, but inactive in non-liver cell and tissue types, thus preventing hGLA expression and activity in non-target tissues. A modified chimeric intron (HBB-IghGLA transgene comprises a codon-optimized hGLA α-Gal A enzyme.

Variant #21 contains a mutated form of the woodchuck hepatitis virus (WHV) posttranscriptional regulatory element (WPREmut6). WPREmut6 is a 592-bp DNA sequence containing the promoter region of WHV X protein followed by a truncated form of the X protein itself with point mutations in the putative promoter region and start codon of the X protein open reading frame to prevent X protein expression (mut6). The poly A sequence is a derivative of the bovine growth hormone polyadenylation signal. The addition of the WPREmut6 element led to increased α-Gal A protein production. Indeed, greater potency was noted with variant #21 expression construct compared to variant #4 expression construct (that lacks the WPREmut6 element).

The variant #21 expression construct can be formulated at approximately 1.0E+13 vg/mL in phosphate buffered saline (PBS) containing CaCl2, MgCl2, NaCl, Sucrose and Kolliphor® P 188 (Poloxamer 188), filled at volumes of 2 mL or 5 mL or 10 mL, etc. into vials, and stored at ≤−65° C. The vials have an aluminum seal with a flip-top.

The expression construct rAAV vector may be packaged with capsid serotype AAV2/6 using a Sf9 insect cell/recombinant baculovirus (Sf9/rBV) expression system. Alternately, the expression construct rAAV vector may be packaged with capsid serotype AAV2/6 using a mammalian expression system, e.g., HEK293.

The studies in the Fabry disease mouse models, wild-type mice and cynomolgus NHPs demonstrate the feasibility of safely producing durable and potentially efficacious levels of α-Gal A after treatment with variant #21 expression vector.

No adverse effects were noted in the mice at dose levels up to 1.5E+14 vg/kg and in the NHPs at dose levels up to 6.0E+13 vg/kg, the highest dose levels given, respectively.

Therefore, the clinical starting dose of 5.0E+12 vg/kg is supported by a 30-fold safety dose multiple in mice and 12-fold safety dose multiple in NHPs.

Measurable levels of α-Gal A are expected in human subjects at a dose of 5.0E+12 vg/kg based on the marked pharmacodynamic response noted in the Fabry disease mice given 2.0E+12 vg/kg.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. An adeno-associated virus (AAV) expression construct comprising an apolipoprotein E (APOE) enhancer comprising the nucleotide sequence as set forth in SEQ ID NO: 2 operably linked to an alpha 1-antitrypsin (hAAT) promoter comprising the nucleotide sequence as set forth in SEQ ID NO: 3, a human hemoglobin beta (HBB)-IGG intron comprising the nucleotide sequence as set forth in SEQ ID NO: 4, an α-galactosidase A (α-Gal A)transgene comprising the nucleotide sequence as set forth in SEQ ID NO: 5, a mutated Woodchuck Hepatitis Virus Posttranscriptional Regulatory Element sequence comprising the nucleotide sequence as set forth in SEQ ID NO: 6, and a bovine growth hormone poly A signal sequence comprising the nucleotide sequence as set forth in SEQ ID NO: 7.

2. A pharmaceutical composition comprising (i) an AAV viral particle which comprises the AAV expression construct of claim 1 and (ii) a pharmaceutically acceptable carrier.

3. The pharmaceutical composition of claim 2, wherein the pharmaceutically acceptable carrier comprises phosphate buffered saline g comprising MgCl$_2$.

4. A genetically modified isolated cell comprising the expression construct of claim 1.

5. The genetically modified cell of claim 4, wherein the cell is a stem cell, precursor cell, a liver cell, or a muscle cell.

6. The genetically modified cell of claim 4, wherein the cell is an insect cell.

7. The AAV expression construct of claim 1, wherein the AAV expression construct is packaged into a capsid of serotype AAV2/6.

8. The AAV expression construct of claim 1, wherein the AAV expression construct further comprises a sequence encoding a signal peptide, wherein the signal peptide comprises an α-Gal A signal peptide, an albumin signal peptide, a Factor IX (FIX) signal peptide, or an iduronate 2-sulfate (IDS) signal peptide.

9. The AAV expression construct of claim 8, wherein the signal peptide comprises the α-Gal A signal peptide.

10. The pharmaceutical composition of claim 3, wherein the phosphate buffered saline further comprises NaCl.

11. The pharmaceutical composition of claim 10, wherein the phosphate buffered saline further comprises sucrose.

12. The pharmaceutical composition of claim 11, wherein the phosphate buffered saline further comprises Poloxamer 188 (P 188).

13. An AAV viral particle comprising the AAV expression construct of claim 1.

14. The AAV viral particle of claim 13, which comprises serotype AAV2/6.

15. A pharmaceutical composition comprising the AAV viral particle of claim 14 and a pharmaceutically acceptable carrier.

16. The genetically modified cell of claim 6, wherein the insect cell is a Sf9 cell.

17. An adeno-associated virus (AAV) expression construct comprising the nucleotide sequence as set forth in SEQ ID NO: 9.

18. An AAV viral particle comprising the AAV expression construct of claim 17, wherein the AAV viral particle comprises serotype AAV2/6.

19. A pharmaceutical composition comprising the AAV expression construct of claim 17 and a pharmaceutically acceptable carrier.

20. A pharmaceutical composition comprising the AAV viral particle of claim 18 and a pharmaceutically acceptable carrier.

* * * * *